(12) United States Patent
Gopalsamy et al.

(10) Patent No.: US 7,217,730 B2
(45) Date of Patent: May 15, 2007

(54) METHOD FOR THE USE OF PYRANOINDOLE DERIVATIVES TO TREAT INFECTION WITH HEPATITIS C VIRUS

(75) Inventors: Ariamala Gopalsamy, Mahwah, NJ (US); John W. Ellingboe, Ridgewood, NJ (US); Tarek S. Mansour, New City, NY (US); Stephen M. Condon, Glenmoore, PA (US); Matthew G. Laporte, Honey Brook, PA (US); Christopher J. Burns, Malvern, PA (US); Kaapjoo Park, Suffern, NY (US); Marc S. Collett, Collegeville, PA (US)

(73) Assignees: Wyeth, Madison, NJ (US); ViroPharma Incorporated, Exton, PA (US)

( * ) Notice: Subject to any disclaimer, the term of this patent is extended or adjusted under 35 U.S.C. 154(b) by 568 days.

(21) Appl. No.: 10/441,984

(22) Filed: May 20, 2003

(65) Prior Publication Data

US 2004/0082643 A1    Apr. 29, 2004

Related U.S. Application Data

(60) Provisional application No. 60/458,706, filed on Mar. 28, 2003, provisional application No. 60/382,154, filed on May 21, 2002.

(51) Int. Cl.
*A61K 31/40* (2006.01)
*A61K 31/70* (2006.01)

(52) U.S. Cl. .................. 514/411; 514/42; 514/43; 514/894

(58) Field of Classification Search ........ 514/411, 514/42, 43, 894
See application file for complete search history.

(56) References Cited

U.S. PATENT DOCUMENTS

| | | | |
|---|---|---|---|
| 3,843,681 A | 10/1974 | Demerson et al. | 260/326.14 R |
| 3,880,853 A | 4/1975 | Demerson et al. | 260/247.5 FP |
| 3,939,178 A | 2/1976 | Demerson et al. | 260/326.28 |
| 3,974,179 A | 8/1976 | Demerson et al. | 260/326.28 |
| 4,012,417 A | 3/1977 | Demerson et al. | 260/326.5 SA |
| 4,036,842 A | 7/1977 | Dobson et al. | 260/293.58 |
| 4,070,371 A | 1/1978 | Demerson et al. | 260/326.29 |
| 4,076,831 A | 2/1978 | Demerson et al. | 424/274 |
| 4,118,394 A | 10/1978 | Demerson et al. | 260/326.28 |
| 4,179,503 A | 12/1979 | Asselin et al. | 424/248.51 |
| 4,501,899 A | 2/1985 | Abraham et al. | 548/432 |
| 4,503,901 A | 3/1985 | Vinogradov et al. | 164/212 |
| 4,515,961 A | 5/1985 | Demerson et al. | 548/432 |
| 4,520,203 A | 5/1985 | Abraham et al. | 548/432 |
| 4,544,757 A | 10/1985 | Demerson et al. | 548/432 |
| 4,585,877 A | 4/1986 | Demerson et al. | 548/432 |
| 4,670,462 A | 6/1987 | Katz et al. | 514/411 |
| 4,686,213 A | 8/1987 | Ferdinandi et al. | 514/161 |
| 4,695,623 A | 9/1987 | Stabinsky | 530/351 |
| 4,785,015 A | 11/1988 | McKittrick et al. | 514/411 |
| 4,810,699 A | 3/1989 | Sabatucci et al. | 514/161 |
| 4,822,781 A | 4/1989 | Katz et al. | 514/161 |
| 4,822,893 A | 4/1989 | Failli | 548/432 |
| 4,897,471 A | 1/1990 | Stabinsky | 536/27 |
| 4,960,902 A | 10/1990 | Failli | 548/432 |
| 5,071,853 A | 12/1991 | Bigge et al. | 514/290 |
| 5,128,363 A | 7/1992 | Failli | 514/411 |
| 5,223,517 A | 6/1993 | Müller | 514/339 |
| 5,599,946 A | 2/1997 | Vincenzo et al. | 548/432 |
| 5,633,388 A | 5/1997 | Diana et al. | 548/305.7 |
| 5,776,967 A | 7/1998 | Kreft et al. | 514/411 |
| 5,824,699 A | 10/1998 | Kreft et al. | 514/411 |
| 5,830,905 A | 11/1998 | Diana et al. | 514/322 |
| 5,830,911 A | 11/1998 | Failli et al. | 514/411 |
| 6,066,741 A | 5/2000 | Vigano et al. | 548/432 |

(Continued)

FOREIGN PATENT DOCUMENTS

WO    WO 95/13090    5/1995

(Continued)

OTHER PUBLICATIONS

Latrine et al. "Hepatite Aigue Associee A La Prise D' Etoclolac", Therapie, vol. 47 (1), 1992 pp. 82-83. (English language translation enclosed).

(Continued)

*Primary Examiner*—Shengjun Wang
(74) *Attorney, Agent, or Firm*—Fitzpatrick, Cella, Harper & Scinto

(57) ABSTRACT

The invention is directed to methods of treating, preventing, or inhibiting a Hepatitis C viral infection in a mammal comprising contacting the mammal with an effective amount of a compound of the formula:

Wherein substitutions at $R_1$, $R_2$, $R_3$—$R_{12}$, and Y are set forth in the specification.

62 Claims, No Drawings

U.S. PATENT DOCUMENTS

| | | | |
|---|---|---|---|
| 6,110,955 A | 8/2000 | Nudelman et al. | 514/411 |
| 6,172,046 B1 * | 1/2001 | Albrecht | 514/43 |
| 6,177,440 B1 | 1/2001 | Bach et al. | 514/292 |
| 6,297,260 B1 | 10/2001 | Bandarage et al. | 514/327 |
| 6,331,638 B1 | 12/2001 | Raghavan et al. | 548/432 |
| 6,365,605 B1 | 4/2002 | Lavielle et al. | 514/338 |
| 6,383,768 B1 | 5/2002 | De Francesco et al. | 435/15 |
| 6,410,583 B1 | 6/2002 | Labelle et al. | 514/411 |
| 2003/0203926 A1 * | 10/2003 | Kois et al. | 514/275 |

FOREIGN PATENT DOCUMENTS

| | | |
|---|---|---|
| WO | WO 98/40066 | 9/1998 |
| WO | WO 98/40078 | 9/1998 |
| WO | WO 01/28555 | 4/2001 |
| WO | WO 02/04425 | 1/2002 |
| WO | WO 02/46170 | 6/2002 |
| WO | WO 02/46171 | 6/2002 |

OTHER PUBLICATIONS

Trechot et al., "Incidence of hepatitis Induced by Non-Steridal Anti-inflammatory Drugs (NSAID)", Annals of the Pheumatic Disease, vol. 55 (12) 1996 pp. 936.

Mallat, "Drug-induced Hepitatis: Diagnosis and Treatment", Gastroenterologic Clinique Et Biologigue, vol. 23 (8-9), 1999, pp. 906-914. (English language translation enclosed).

*Hepatology*, 1997, vol. 26 (1), pp. 2S-10S.

Purcell, *Hepatology* 1997, vol. 26 (1), pp. 11S-14S.

Bartenschlager, *Antiviral Chemistry and Chemotherapy*, 1997, vol. 8 (4), pp. 281-301.

Bartenschlager et al., *J. General Virology*, 2001, vol. 81, part 7, pp. 1631-1648.

Ferrari et al., *J. Virology*, 1999, vol. 73 (2), pp. 1649-1654.

Takamizawa et al., *J. Virology*, 1991, vol. 65 (3), pp. 1105-1113.

Courtin, *Helv. Chim. Acta*, 1983, vol. 66 (1), pp. 68-75.

McKittrick et al., *J. Heterocyclic Chem.* 1990, vol. 27 (7), pp. 2151-2163.

Blight et al., *Science*, 2000, vol. 290 (5498), pp. 1972-1974.

Lohmann et al., *Science*, 1999, vol. 285 (5424), pp. 110-113.

Pietschmann et al., *J. Virol*, 2001, vol. 75 (3), pp. 1252-1264.

Lohmann et al., *J. Virol.*, 2001, vol. 75 (3), pp. 1437-1449.

Humber et al., J. Med. Chem., 1986, vol. 29, pp. 871-874.

* cited by examiner

METHOD FOR THE USE OF PYRANOINDOLE DERIVATIVES TO TREAT INFECTION WITH HEPATITIS C VIRUS

This application claims the benefit of U.S. Provisional Application No. 60/382,154, filed on May 21, 2002, and U.S. Provisional Application No. 60/458,706, filed Mar. 28, 2003. These applications are hereby incorporated by reference.

BACKGROUND OF THE INVENTION

1. Field of the Invention

This invention is directed to pyranoindole derivatives, pharmaceutical compositions containing them, and to their use in the treatment of Hepatitis C viral infections, either alone or in conjunction with one or more biologically active agents, either concurrently or sequentially.

2. Related Background Art

Hepatitis C is a common viral infection that can lead to chronic Hepatitis, cirrhosis, liver failure, and hepatocellular carcinoma. Infection with the Hepatitis C virus (HCV) leads to chronic Hepatitis in at least 85% of cases, is the leading reason for liver transplantation, and is responsible for at least 10,000 deaths annually in the United States (Hepatology, 1997, 26 (Suppl. 1), 2S–10S).

The Hepatitis C virus is a member of the Flaviviridae family, and the genome of HCV is a single-stranded linear RNA of positive sense (Hepatology, 1997, 26 (Suppl. 1), 11S–14S). HCV displays extensive genetic heterogeneity; at least 6 genotypes and more than 50 subtypes have been identified.

There is no effective vaccine to prevent HCV infection. The only therapy currently available is treatment with interferon-α (INF-α or combination therapy of INF-α with the nucleoside analog ribavirin (Antiviral Chemistry and Chemotherapy, 1997, 8, 281–301). However, only about 40% of treated patients develop a sustained response, so there is a need for more effective anti-HCV therapeutic agents.

The HCV genome contains a number of non-structural proteins: NS2, NS3, NS4A, NS4B, NS5A, and NS5B (J. General Virology, 2000, 81, 1631–1648). NS5B is an RNA-dependent RNA polymerase which is essential for viral replication, and therefore, the inhibition of NS5B is a suitable target for the development of therapeutic agents.

In the following U.S. patents, pyranoindole derivatives are disclosed and the compounds are stated to have antidepressant and antiulcer activity: U.S. Pat. No. 3,880,853 (Apr. 29, 1975), U.S. Pat. No. 4,118,394 (Oct. 3, 1978). In U.S. Pat. No. 4,179,503 (Dec. 18, 1979) pyranoindoles are disclosed and stated to have diuretic activity. In the following U.S. patents, pyranoindole derivatives are disclosed and the compounds are stated to have antiinflammatory, analgesic, antibacterial, and antifungal activity: U.S. Pat. No. 3,843,681 (Oct. 22, 1974), U.S. Pat. No. 3,939,178 (Feb. 17, 1976), U.S. Pat. No. 3,974,179 (Aug. 10, 1976), U.S. Pat. No. 4,070,371 (Jan. 24, 1979), U.S. Pat. No. 4,076,831 (Feb. 28, 1978). In the following U.S. patents, pyranoindole derivatives are disclosed and the compounds are stated to have antiinflammatory and analgesic activity: U.S. Pat. No. 4,670,462 (Jun. 2, 1987), U.S. Pat. No. 4,686,213 (Aug. 11, 1987), U.S. Pat. No. 4,785,015 (Nov. 15, 1988), U.S. Pat. No. 4,810,699 (Mar. 7, 1989), U.S. Pat. No. 4,822,781 (Apr. 18, 1989), U.S. Pat. No. 4,960,902 (Oct. 2, 1990). In U.S. Pat. No. 5,776,967 (Jul. 7, 1998) and U.S. Pat. No. 5,830,911 (Nov. 3, 1998), pyranoindole derivatives are disclosed and the compounds are said to inhibit cyclooxegenase-2 and be useful for treating arthritic disorders, colorectal cancer, and Alzheimer's disease.

Also, in the following U.S. patents, processes for preparing pyranoindole derivatives are disclosed: U.S. Pat. No. 4,012,417 (Mar. 15, 1977), U.S. Pat. No. 4,036,842 (Jul. 19, 1977), U.S. Pat. No. 4,585,877 (Apr. 29, 1986), U.S. Pat. No. 4,822,893 (Apr. 18, 1989). Processes for the resolution of racemic pyranoindole derivatives are disclosed in the following US Patents: U.S. Pat. No.: 4,501,899 (Feb. 26, 1985), U.S. Pat. No. 4,515,961 (May 7, 1985), U.S. Pat. No. 4,520,203 (May 28, 1985), U.S. Pat. No. 4,544,757 (Oct. 1, 1985).

Other aspects of the instant invention are described in applicant's U.S. provisional patent application No. 60/382, 148, filed concurrently with the instant application, and which is hereby incorporated by reference in its entirety.

BRIEF SUMMARY OF THE INVENTION

This invention relates to pyranoindole derivatives, processes for their preparation and pharmaceutical compositions containing them, and to their use in the treatment of Hepatitis C viral infection. This invention further relates to methods of treating or preventing a Hepatitis C viral infection in a mammal, said methods comprising providing the mammal with an effective amount of at least one pharmaceutical composition, wherein the pharmaceutical composition includes a compound of the invention which is a pyranoindole derivative and further comprising providing the mammal with at least one biologically active agent, either concurrently or sequentially with the pharmaceutical composition. This invention also relates to methods of inhibiting replication of a Hepatitis C virus, said methods comprising contacting the virus with an effective amount of at least one pharmaceutical composition, wherein the pharmaceutical composition includes a compound of the invention which is a pyranoindole derivative and further comprising providing the mammal with at least one biologically active agent, either concurrently or sequentially with the pharmaceutical composition.

In accordance with this invention there is provided a group of compounds represented by formula (I):

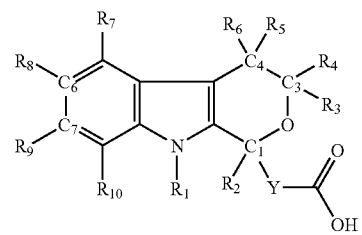

wherein:
R$_1$ is H, a straight chain alkyl of 1 to 8 carbon atoms, a branched alkyl of 3 to 12 carbon atoms, a cycloalkyl of 3 to 12 carbon atoms, an alkenyl of 2 to 7 carbon atoms, an alkynyl of 2 to 7 carbon atoms, or an arylalkyl or an alkylaryl of 7 to 12 carbon atoms;

R$_2$ is H, a straight chain alkyl of 1 to 12 carbon atoms, a branched alkyl of 3 to 12 carbon atoms, a cycloalkyl of 3 to 12 carbon atoms, an alkenyl of 2 to 7 carbon atoms, an alkynyl of 2 to 7 carbon atoms, an alkoxyalkyl of 2 to 12 carbon atoms, an arylalkyl or alkylaryl of 7 to 12 carbon atoms, a cyanoalkyl of 1 to 8 carbon atoms, an alkylthioalkyl of 2 to 16 carbon atoms, a cycloalkylalkyl of 4 to 24 carbon atoms, a substituted or unsubstituted aryl, or a heteroaryl;

$R_3$–$R_6$ are independently H, a straight chain alkyl of 1 to 8 carbon atoms, a branched alkyl of 3 to 12 carbon atoms, a cycloalkyl of 3 to 12 carbon atoms, an alkenyl of 2 to 7 carbon atoms, a substituted or unsubstituted aryl, furanylmethyl, arylalkyl or alkylaryl of 7 to 12 carbon atoms, alkynyl of 2 to 7 carbon atoms, or $R_5$ and $R_6$ together with the ring carbon atom to which they are attached form a carbonyl group;

$R_7$–$R_{10}$ are independently H, a straight chain alkyl of 1 to 8 carbon atoms, a branched alkyl of 3 to 12 carbons atoms, a cycloalkyl of 3 to 12 carbon atoms, an alkenyl of 2 to 7 carbon atoms, a substituted or unsubstituted aryl, a substituted or unsubstituted heteroaryl, furanylmethyl, arylalkyl or alkylaryl of 7 to 12 carbon atoms, alkynyl of 2 to 7 carbon atoms, phenylalkynyl, alkoxy of 1 to 8 carbon atoms, arylalkoxy of 7 to 12 carbon atoms, fluoroalkoxy of 1 to 12 carbon atoms, alkylthio of 1 to 8 carbon atoms, trifluoromethoxy, trifluoroethoxy, trifluoromethylthio, trifluoroethylthio, acyl of 1 to 7 carbon atoms, COOH, COO-alkyl, CONR$_{11}$R$_{12}$, F, Cl, Br, I, CN, CF$_3$, NO$_2$, alkylsulfinyl of 1 to 8 carbon atoms, alkylsulfonyl of 1 to 6 carbon atoms, pyrrolidinyl, or thiazolidinyl;

$R_{11}$–$R_{12}$ are independently H, straight chain alkyl of 1 to 8 carbon atoms, branched alkyl of 3 to 12 carbon atoms, cycloalkyl of 3 to 12 carbon atoms, a substituted or unsubstituted aryl or heteroaryl;

Y is a bond, CH$_2$, CH$_2$CH$_2$, aryl, or $R_2$ and Y together with the ring carbon atom to which they are attached may additionally form a spirocyclic cycloalkyl ring of 3 to 8 carbon atoms; or a crystalline form or a pharmaceutically acceptable salt thereof.

For purposes of this invention the term "alkyl" includes both straight and branched alkyl moieties, preferably of 1 to 8 carbon atoms. The term "alkenyl" refers to a radical aliphatic hydrocarbon containing one double bond and includes both straight and branched alkenyl moieties of 2 to 7 carbon atoms. Such alkenyl moieties may exist in the E or Z configurations; the compounds of this invention include both configurations. The term "alkynyl" includes both straight chain and branched moieties containing 2 to 7 carbon atoms having at least one triple bond. The term "cycloalkyl" refers to alicyclic hydrocarbon groups having 3 to 12 carbon atoms and includes but is not limited to: cyclopropyl, cyclobutyl, cyclopentyl, cyclohexyl, cycloheptyl, norbornyl, or adamantyl.

For purposes of this invention the term "aryl" is defined as an aromatic hydrocarbon moiety and may be substituted or unsubstituted. An aryl may be selected from but not limited to, the group: phenyl, α-naphthyl, β-naphthyl, biphenyl, anthryl, tetrahydronaphthyl, phenanthryl, fluorenyl, indanyl, biphenylenyl, acenaphthenyl, acenaphthylenyl, or phenanthrenyl groups. In one embodiment the substituted aryl may be optionally mono-, di-, tri- or tetra-substituted with substituents selected from, but not limited to, the group consisting of alkyl, acyl, alkoxycarbonyl, alkoxy, alkoxyalkyl, alkoxyalkoxy, cyano, halogen, hydroxy, nitro, trifluoromethyl, trifluoromethoxy, trifluoropropyl, amino, alkylamino, dialkylamino, dialkylaminoalkyl, hydroxyalkyl, alkoxyalkyl, alkylthio, —SO$_3$H, —SO$_2$NH$_2$, —SO$_2$NHalkyl, —SO$_2$N(alkyl)$_2$, —CO$_2$H, CO$_2$NH$_2$, CO$_2$NHalkyl, and —CO$_2$N(alkyl)$_2$. Preferred substituents for aryl and heteroaryl include: alkyl, halogen, amino, alkylamino, dialkylamino, trifluoromethyl, trifluoromethoxy, arylalkyl, and alkylaryl.

For purposes of this invention the term "heteroaryl" is defined as an aromatic heterocyclic ring system (monocyclic or bicyclic) where the heteroaryl moieties are five or six membered rings containing 1 to 4 heteroatoms selected from the group consisting of S, N, and O, and include but is not limited to: (1) furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1methyl-1,2,4-triazole, 1H-tetrazole, 1-methyltetrazole, benzoxazole, benzothiazole, benzofuran, benzisoxazole, benzimidazole, N-methylbenzimidazole, azabenzimidazole, indazole, quinazoline, quinoline, pyrrolidinyl; (2) a bicyclic aromatic heterocycle where a phenyl, pyridine, pyrimidine or pyridizine ring is: (i) fused to a 6-membered aromatic (unsaturated) heterocyclic ring having one nitrogen atom; (ii) fused to a 5 or 6-membered aromatic (unsaturated) heterocyclic ring having two nitrogen atoms; (iii) fused to a 5-membered aromatic (unsaturated) heterocyclic ring having one nitrogen atom together with either one oxygen or one sulfur atom; or (iv) fused to a 5-membered aromatic (unsaturated) heterocyclic ring having one heteroatom selected from O, N or S.

For the purposes of this invention the term "alkoxy" is defined as C1–C12-alkyl-O—; the term "aryloxy" is defined as aryl-O—; the term "heteroaryloxy" is defined as heteroaryl-O—; wherein alkyl, aryl, and heteroaryl are as defined above.

For purposes of this invention the term "arylalkyl" is defined as aryl-C1–C6-alkyl-; arylalkyl moieties include benzyl, 1-phenylethyl, 2-phenylethyl, 3-phenylpropyl, 2-phenylpropyl and the like.

For purposes of this invention the term "alkylaryl" is defined as C1–C6-alkyl-aryl-.

For purposes of this invention the term "alkylthio" is defined as C1–C6alkyl-S—.

For purposes of this invention "alkoxyalkyl," "cycloalkylalkyl," "alkylthioalkyl," "aryloxyalkyl," and "heteroaryloxyalkyl" denote an alkyl group as defined above that is further substituted with an alkoxy, cycloalkyl, alkylthio, aryloxy, or heteroaryloxy group as defined above.

For purposes of this invention "arylalkoxy," "alkoxyalkoxy," "fluoroalkoxy," "alkylthioalkoxy," and "heteroarylalkoxy" denote an alkoxy group as defined above that is further substituted with an aryl, alkoxy, fluoro, alkylthio, or heteroaryl group as defined above.

For purposes of this invention "arylthio" and "heteroarylthio," denote a thio group that is further substituted with an aryl or heteroaryl group as defined above.

For purposes of this invention "arylthioalkyl" and "heteroarylthioalkyl" denote an alkyl group as defined above that is further substituted with an arylthio or heteroarylthio group as defined above.

For purposes of this invention the term "arylalkylthio" is defined as aryl-C1–C8-alkyl-S—; "heteroarylalkylthio" is defined as heteroaryl-C1–C8-alkyl-S—, where aryl and heteroaryl are as defined above.

For purposes of this invention "aryloxyalkylthio" is defined as aryloxy-C1–C8-alkyl-S; "heteroaryloxyalkylthio" is defined as heteroaryloxy-C1–C8alkyl-S—; where aryloxy, heteroaryloxy, and alkyl are defined above.

For purposes of this invention "phenylalkynyl" is an alkynyl group further substituted with a phenyl group.

In the most preferred embodiment of this invention a substituted methyl comprises a methyl substituent further substituted with for example a furanyl group. In another embodiment of this invention a furanyl substituent is further substituted with a methyl group.

In a preferred embodiment of this invention trifluoromethoxy is CF3O—. In another embodiment of this invention trifluoromethylthio is CF3S—.

In one embodiment of this invention trifluoroethoxy includes but is not limited to CF3CH2O—. In another embodiment of this invention trifluoroethylthio includes but is not limited to CF3CH2S—.

The terms "monoalkylamino" and "dialkylamino" refer to moieties with one or two alkyl groups wherein the alkyl chain is 1 to 8 carbons and the groups may be the same or different. The terms monoalkylaminoalkyl and dialkylaminoalkyl refer to monoalkylamino and dialkylamino moieties with one or two alkyl groups (the same or different) bonded to the nitrogen atom which is attached to an alkyl group of 1 to 8 carbon atoms.

"Acyl" is a radical of the formula —(C═O)-alkyl or —(C═O)-perfluoroalkyl wherein the alkyl radical or perfluoroalkyl radical is 1 to 7 carbon atoms; preferred examples include but are not limited to, acetyl, propionyl, butyryl, trifluoroacetyl.

For purposes of this invention the term "alkylsulfinyl" is defined as a R'SO- radical, where R' is an alkyl radical of 1 to 8 carbon atoms. Alkylsulfonyl is a R'SO2-radical, where R' is an alkyl radical of 1 to 8 carbon atoms. Alkylsulfonamido, alkenylsulfonamido, alkynylsulfonamido are R'SO2NH-radicals, where R' is an alkyl radical of 1 to 8 carbon atoms, an alkenyl radical of 2 to 8 carbon atoms, or an alkynyl radical of 2 to 8 carbon atoms, respectively.

Saturated or partially saturated heteroaryl groups are defined in this invention as heterocyclic rings selected from but not limited to the moieties: azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothienyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dihydro-1,4-dioxanyl, tetrahydrofuranyl, tetrahydrothienyl, tetrahydroquinolinyl, and tetrahydroisoquinolinyl .

For purposes of this invention, the term "BB7" denotes an RNA-dependent RNA polymerase hepatitis C virus protein sequence which is derived from HCV replicon. A discussion of BB7 and related technology can be found in Blight, K. et al. (2000) Science 290:1972–1974. BB7 can be licensed from Apath, LLC (893 North Warson Road, Saint Louis Mo. 63141, USA). BB7 is also referred to as Con1 HCV sequence and discussions of Con1 can be found in the following references: Lohmann, V. et al. (1999) Science 285:110–113; Pietschmann, T. et al. (2001) J. Virol. 75:1252–1264; Lohmann, V. et al. (2001) J. Virol. 75:1437–1449.

The compounds of this invention may contain an asymmetric carbon atom and some of the compounds of this invention may contain one or more asymmetric centers and may thus give rise to stereoisomers, such as enantiomers and diastereomers. The stereoisomers of the instant invention are named according to the Cahn-Ingold-Prelog System. While shown without respect to stereochemistry in Formula (I), the present invention includes all the individual possible stereoisomers; as well as the racemic mixtures and other mixtures of R and S stereoisomers (scalemic mixtures which are mixtures of unequal amounts of enantiomers) and pharmaceutically acceptable salts thereof. It should be noted that stereoisomers of the invention having the same relative configuration at a chiral center may nevertheless have different R and S designations depending on the substitution at the indicated chiral center.

For compounds of this invention containing two chiral centers, four possible stereoisomers are possible; these four stereoisomers are classified as two racemic pairs of diastereomers. These compounds of the invention may be present as racemic diastereomers which would be designated following the convention described in the 1997 Chemical Abstracts Index Guide, Appendix IV (Columbus, Ohio) whereas the first cited chiral atom is designated R* and the next cited chiral atom is designated R* if it possesses the same chirality as the first cited stereocenter or S* if it possesses opposite chirality to the first cited stereocenter. Alternatively, these compounds of the invention may be present as non-racemic mixtures of two diastereomers owing to the existence of a predefined stereocenter. In these instances, the predefined stereocenter is assigned based on the Cahn-Ingold-Prelog System and the undefined stereocenter is designated R* to denote a mixture of both R and S stereoisomers at this center. Compounds of this invention which possess two chiral centers but which are present as single stereoisomers are described using the Cahn-Ingold-Prelog System.

To further clarify, the following examples of naming possibilities are provided below:

| Designation | Possible stereoisomers | See example |
| --- | --- | --- |
| 1R* 10S | 1R 10S and 1S 10S | 261 |
| 1R* 10S* | 1R 10S and 1S 10R | 289 |
| 1R* 10R* | 1R 10R and 1S 10S | 290 |

Based on the chiral center at the $C_1$ carbon position in formula (1), a preferred embodiment of the instant invention is the compound of formula (Ia) shown below:

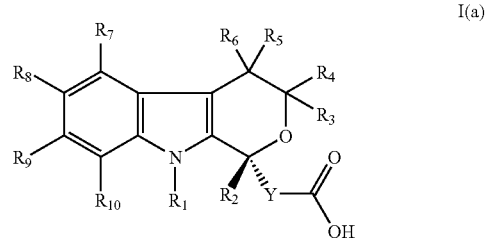

I(a)

The configuration at $C_1$ in Formula (Ia) for purposes of this invention is also referred to as "Isomer A", and the opposite configuration at $C_1$ is herein

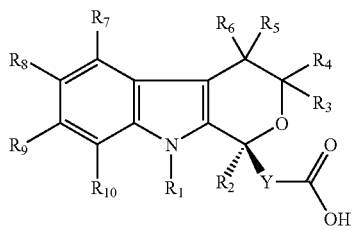

defined as "Isomer B" and has the formula (1b) shown below:

In one embodiment of this invention the compound of the invention is comprised of a ratio of Isomer A to Isomer B of greater than 1:1. In the most preferred embodiment the compound is comprised of 100% Isomer A. In further embodiments the compound is comprised of a ratio of Isomer A to Isomer B of at least about 9:1. In another embodiment the compound is comprised of a ratio of Isomer A to Isomer B of at least about 8:1. Additionally the compound is comprised of a ratio of Isomer A to Isomer B of at least about 7:1.

Another embodiment of this invention is where $R_2$ of formula (I) is a sec-butyl group. In a preferred embodiment, the chiral carbon of the sec-butyl group has an S to R configuration ratio of 1:1. In further embodiments, the chiral carbon of the sec-butyl group has an S to R configuration ratio selected from the group consisting of at least 7:1, at least 8:1, and at least 9:1. In a most preferred embodiment of the invention, the chiral carbon of the sec-butyl group has 100% S configuration.

Pharmaceutically acceptable salts of the compounds of formula (I) having acidic moieties at $R_3$, $R_4$, $R_5$, $R_6$, $R_7$, $R_8$, $R_9$, or $R_{10}$ may be formed from organic and inorganic bases. For example alkali metal salts: sodium, lithium, or potassium and N-tetraalkylammonium salts such as N-tetrabutylammonium salts. Similarly, when a compound of this invention contains a basic moiety at $R_3$, $R_4$, $R_5$, $R_6$, $R_7$, $R_8$, $R_9$, or $R_{10}$ salts can be formed from organic and inorganic acids. For example salts can be formed from acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids.

In one embodiment, the present invention provides for a method of inhibiting the Hepatitis C RNA-dependent RNA polymerase NS5B. The method comprises contacting a cell with an amount of a compound effective to decrease or prevent NS5B function. The cell may be a mammalian cell and more specifically a human cell. The cell may also be a bacterial cell such as for example *E coli*. The cell may include but is not limited to, a neuronal cell, an endothelial cell, a glial cell, a microglial cell, a smooth muscle cell, a somatic cell, a bone marrow cell, a liver cell, an intestinal cell, a germ cell, a myocyte, a mononuclear phagocyte, an endothelial cell, a tumor cell, a lymphocyte cell, a mesangial cell, a retinal epithelial cell, a retinal vascular cell, a ganglion cell or a stem cell. The cell may be a normal cell, an activated cell, a neoplastic cell, a diseased cell, or an infected cell.

In another embodiment, the present invention provides for a method of inhibiting the Hepatitis C RNA-dependent RNA polymerase NS5B, comprising contacting a cell with an amount of a pharmaceutical composition, that comprises a compound of this invention, in combination or association with a pharmaceutically acceptable carrier in an amount effective to decrease or prevent NS5B function. The cell may be a mammalian cell and more specifically a human cell. The cell may also be a bacterial cell such as for example *E coli*. The cell may include but is not limited to, a neuronal cell, an endothelial cell, a glial cell, a microglial cell, a smooth muscle cell, a somatic cell, a bone marrow cell, a liver cell, an intestinal cell, a germ cell, a myocyte, a mononuclear phagocyte, an endothelial cell, a tumor cell, a lymphocyte cell, a mesangial cell, a retinal epithelial cell, a retinal vascular cell, a ganglion cell or a stem cell. The cell may be a normal cell, an activated cell, a neoplastic cell, a diseased cell, or an infected cell.

In another embodiment, the present invention provides a method for the treatment or prevention of Hepatitis C infection in a mammal. The present invention accordingly provides to a mammal, a pharmaceutical composition that comprises a compound of this invention in combination or association with a pharmaceutically acceptable carrier. The compound of this invention may be administered alone or in combination with other therapeutically effective compounds or therapies for the treatment or prevention of Hepatitis C viral infection in a mammal.

The compounds and pharmaceutical compositions of the present invention are preferably provided orally or subcutaneously. The compounds may be provided by intralesional, intraperitoneal, intramuscular or intravenous injection; infusion; liposome-mediated delivery; topical, nasal, anal, vaginal, sublingual, uretheral, transdermal, intrathecal, ocular or otic delivery. In order to obtain consistency in providing the compound of this invention it is preferred that a compound of the invention is in the form of a unit dose. Suitable unit dose forms include tablets, capsules and powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compounds may be administered from 1 to 6 times a day, more usually from 1 to 4 times a day. The effective amount will be known to one of skill in the art; it will also be dependent upon the form of the compound. One of skill in the art could routinely perform empirical activity tests to determine the bioactivity of the compound in bioassays and thus determine what dosage to administer.

The compounds and pharmaceutical compositions of the invention may be formulated with conventional excipients, such as a filler, a disintegrating agent, a binder, a lubricant, a flavoring agent, a color additive, or a carrier. The carrier may be for example a diluent, an aerosol, a topical carrier, an aqueous solution, a nonaqueous solution or a solid carrier. The carrier may be a polymer or a toothpaste. A carrier in this invention encompasses any of the standard pharmaceutically accepted carriers, such as phosphate buffered saline solution, acetate buffered saline solution, water, emulsions such as an oil/water emulsion or a triglyceride emulsion, various types of wetting agents, tablets, coated tablets and capsules.

When provided orally or topically, such compounds would be provided to a subject by delivery in different carriers. Typically, such carriers contain excipients such as starch, milk, sugar, certain types of clay, gelatin, stearic acid, talc, vegetable fats or oils, gums, or glycols. The specific carrier would need to be selected based upon the desired method of delivery, for example, phosphate buffered saline (PBS) could be used for intravenous or systemic delivery and vegetable fats, creams, salves, ointments or gels may be used for topical delivery.

The compounds and pharmaceutical compositions of the present invention may be delivered together with suitable diluents, preservatives, solubilizers, emulsifiers, adjuvants and/or carriers useful in treatment or prevention of Hepatitis C viral infection. Such compositions are liquids or lyophilized or otherwise dried formulations and include diluents of various buffer content (for example, Tris-HCl, acetate, phosphate), pH and ionic strength, additives such as albumins or gelatin to prevent absorption to surfaces, detergents (for example, TWEEN 20, TWEEN 80, PLURONIC F68, bile acid salts), solubilizing agents (for example, glycerol, polyethylene glycerol), anti-oxidants (for example ascorbic acid, sodium metabisulfate), preservatives (for example, thimerosal, benzyl alcohol, parabens), bulking substances or tonicity modifiers (for example, lactose, mannitol), covalent attachment of polymers such as polyethylene glycol, complexation with metal ions, or incorporation of the compound into or onto particulate preparations of hydrogels or liposomes, micro-emulsions, micelles, unilamellar or multilamellar vesicles, erythrocyte ghosts, or spheroplasts. Such compositions will influence the physical state, solubility, stability, rate of in vivo release, and rate of in vivo clearance of the compound or composition. The choice of compositions will depend on the physical and chemical properties of the compound capable of treating or preventing a Hepatitis C viral infection.

The compound and pharmaceutical compositions of the present invention may be delivered locally via a capsule that allows a sustained release of the compound over a period of time. Controlled or sustained release compositions include formulation in lipophilic depots (for example, fatty acids, waxes, oils).

The present invention further provides controlled-release therapeutic dosage forms for the pharmaceutical composition in which the composition is incorporated into a delivery system. The dosage form controls release of the pharmaceutical composition in such a manner that an effective concentration of the composition in the blood can be maintained over an extended period of time, but also the release of the composition should be such that the concentration in the blood remains relatively constant over the extended period of time to improve therapeutic results and/or minimize side effects. Additionally, a controlled release system would affect minimal peak to trough fluctuations in blood plasma levels of the pharmaceutical composition.

The present invention further provides a compound of the invention for use as an active therapeutic substance for preventing Hepatitis C infection. Compounds of formula (I) are of particular use for the treatment of infection with Hepatitis C virus.

The present invention further provides a method of treating Hepatitis C infection in humans, which comprises administering to the infected individual an effective amount of a compound or a pharmaceutical composition of the invention.

The present invention provides a method of treating or preventing a Hepatitis C viral infection in a mammal comprising providing the mammal with an effective amount of at least one pharmaceutical composition, wherein the at least one pharmaceutical composition includes a compound of a formula:

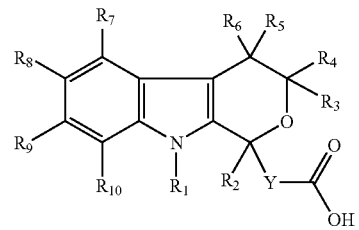

wherein:
  $R_1$ is H, a straight chain alkyl of 1 to 8 carbon atoms, a branched alkyl of 3 to 12 carbon atoms, a cycloalkyl of 3 to 12 carbon atoms, an alkenyl of 2 to 7 carbon atoms, an alkynyl of 2 to 7 carbon atoms, or an arylalkyl or an alkylaryl of 7 to 12 carbon atoms;
  $R_2$ is H, a straight chain alkyl of 1 to 12 carbon atoms, a branched alkyl of 3 to 12 carbon atoms, a cycloalkyl of 3 to 12 carbon atoms, an alkenyl of 2 to 7 carbon atoms, an alkynyl of 2 to 7 carbon atoms, an alkoxyalkyl of 2 to 12 carbon atoms, an arylalkyl or alkylaryl of 7 to 12 carbon atoms, a cyanoalkyl of 1 to 8 carbon atoms, an alkylthioalkyl of 2 to 16 carbon atoms, a cycloalkylalkyl of 4 to 24 carbon atoms, a substituted or unsubstituted aryl, or a heteroaryl;
  $R_3$–$R_6$ are independently H, a straight chain alkyl of 1 to 8 carbon atoms, a branched alkyl of 3 to 12 carbon atoms, a cycloalkyl of 3 to 12 carbon atoms, an alkenyl of 2 to 7 carbon atoms, a substituted or unsubstituted aryl, furanylmethyl, arylalkyl or alkylaryl of 7 to 12 carbon atoms, alkynyl of 2 to 7 carbon atoms, or $R_5$ and $R_6$ together with the ring carbon atom to which they are attached form a carbonyl group;
  $R_7$–$R_{10}$ are independently H, a straight chain alkyl of 1 to 8 carbon atoms, a branched alkyl of 3 to 12 carbons atoms, a cycloalkyl of 3 to 12 carbon atoms, an alkenyl of 2 to 7 carbon atoms, a substituted or unsubstituted aryl, a substituted or unsubstituted heteroaryl, furanylmethyl, arylalkyl or alkylaryl of 7 to 12 carbon atoms, alkynyl of 2 to 7 carbon atoms, phenylalkynyl, alkoxy of 1 to 8 carbon atoms, arylalkoxy of 7 to 12 carbon atoms, fluoroalkoxy of 1 to 12 carbon atoms, alkylthio of 1 to 8 carbon atoms, trifluoromethoxy, trifluoroethoxy, trifluoromethylthio, trifluoroethylthio, acyl of 1 to 7 carbon atoms, COOH, COO-alkyl, $CONR_{11}R_{12}$, F, Cl, Br, I, CN, $CF_3$, $NO_2$, alkylsulfinyl of 1 to 8 carbon atoms, alkylsulfonyl of 1 to 6 carbon atoms, pyrrolidinyl, or thiazolidinyl;
  $R_{11}$–$R_{12}$ are independently H, straight chain alkyl of 1 to 8 carbon atoms, branched alkyl of 3 to 12 carbon atoms, cycloalkyl of 3 to 12 carbon atoms, a substituted or unsubstituted aryl or heteroaryl;
  Y is a bond, $CH_2$, $CH_2CH_2$, aryl, or $R_2$ and Y together with the ring carbon atom to which they are attached form a spirocyclic cycloalkyl ring of 3 to 8 carbon atoms and a pharmaceutically acceptable carrier.

The method of the present invention further comprises providing the mammal with an effective amount of at least one biologically active agent.

In an embodiment of the method of the present invention, the at least one biologically active agent is provided prior to the at least one pharmaceutical composition, concurrently with the at least one pharmaceutical composition or after the at least one pharmaceutical composition. In a further embodiment of the method of the present invention, the compound is a crystalline form or a pharmaceutically acceptable salt thereof.

In a further embodiment of the method of the present invention, the at least one biologically active agent is selected from the group consisting of interferon, a pegylated interferon, ribavirin, protease inhibitors, polymerase inhibitors, small interfering RNA compounds, anti-sense compounds, nucleotide analogs, nucleoside analogs, immunoglobulins, immunomodulators, hepatoprotectants, anti-inflammatory agents, antibiotics, antivirals, and anti-infective compounds. In a further embodiment the at least one biologically active agent is a pegylated interferon. In a yet further embodiment the pegylated interferon is a pegylated interferon-alpha and the compound is

[(R)-5-cyano-8-methyl-1-propyl-1,3,4,9-tetrahydropyrano[3,4-b]indol-1-yl]acetic acid. In a yet further embodiment the pegylated interferon is a pegylated interferon-alpha and the compound is [(R)-5-cyano-6-fluoro-8-methyl-1-propyl-1,3,4,9-tetrahydropyrano[3,4-b]indol-1-yl]acetic acid.

The present invention also provides a method of treating or preventing a Hepatitis C viral infection in a mammal comprising providing the mammal with an effective amount of at least one pharmaceutical composition, wherein the at least one pharmaceutical composition includes a compound of a formula:

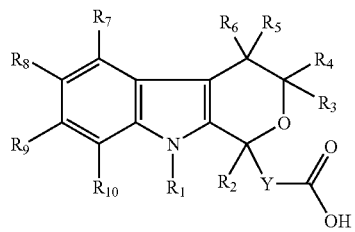

wherein:
$R_1$ is H, a straight chain alkyl of 1 to 6 carbon atoms, a branched alkyl of 3 to 10 carbon atoms, a cycloalkyl of 3 to 10 carbon atoms, an alkenyl of 2 to 7 carbon atoms, an alkynyl of 2 to 7 carbon atoms, or an arylalkyl of 7 to 12 carbon atoms;

$R_2$ is H, a straight chain alkyl of 1 to 12 carbon atoms, a branched alkyl of 3 to 10 carbon atoms, a cycloalkyl of 3 to 10 carbon atoms, an alkenyl of 2 to 7 carbon atoms, an alkynyl of 2 to 7 carbon atoms, an alkoxyalkyl of 2 to 12 carbon atoms, an arylalkyl of 7 to 12 carbon atoms, an unsubstituted aryl or an aryl substituted with one to four groups, or heteroaryl;

$R_3$–$R_6$ are independently H, a straight chain alkyl of 1 to 6 carbon atoms, a branched alkyl of 3 to 10 carbons atoms, a cycloalkyl of 3 to 10 carbon atoms, an alkenyl of 2 to 7 carbon atoms, an unsubstituted aryl or an aryl substituted with one to four groups, furanylmethyl, an arylalkyl of 7 to 12 carbon atoms, an alkynyl of 2 to 7 carbon atoms, or $R_5$ and $R_6$ together with the ring carbon atom to which they are attached form a carbonyl group;

$R_7$–$R_{10}$ are independently H, a straight chain alkyl of 1 to 6 carbon atoms, a branched alkyl of 3 to 10 carbons atoms, a cycloalkyl of 3 to 10 carbon atoms, an alkenyl of 2 to 7 carbon atoms, an unsubstituted aryl or an aryl substituted with one to four groups, an unsubstituted heteroaryl or a heteroaryl substituted with one to three groups, furanylmethyl, an arylalkyl of 7 to 12 carbon atoms, an alkenyl of 2 to 7 carbon atoms, phenylalkynyl, an alkoxy of 1 to 6 carbon atoms, an arylalkoxy of 7 to 12 carbon atoms, a fluoroalkoxy of 1 to 12 carbon atoms, an alkylthio of 1 to 6 carbon atoms, trifluoromethoxy, trifluoroethoxy, trifluoromethylthio, trifluoroethylthio, an acyl of 1 to 7 carbon atoms, a carboxy group, $CONR_{11}R_{12}$, F, Cl, Br, I, CN, $CF_3$, $NO_2$, an alkylsulfinyl of 1 to 6 carbon atoms, an alkylsulfonyl of 1 to 6 carbon atoms;

$R_{11}$–$R_{12}$ are independently H, a straight chain alkyl of 1 to 6 carbon atoms, a branched alkyl of 3 to 10 carbon atoms, a cycloalkyl of 3 to 10 carbon atoms, an aryl substituted with one to four groups, an unsubstituted heteroaryl or a heteroaryl substituted with one to three groups;

Y is $CH_2$, $CH_2CH_2$, or aryl; and a pharmaceutically acceptable carrier.

The method of the present invention further comprises providing the mammal with an effective amount of at least one biologically active agent.

In an embodiment of the method of the present invention, the at least one biologically active agent is provided prior to the at least one pharmaceutical composition, concurrently with the at least one pharmaceutical composition or after the at least one pharmaceutical composition. In a further embodiment of the method of the present invention, the compound is a crystalline form or a pharmaceutically acceptable salt thereof.

In a further embodiment of the method of the present invention, the at least one biologically active agent is selected from the group consisting of interferon, a pegylated interferon, ribavirin, protease inhibitors, polymerase inhibitors, small interfering RNA compounds, anti-sense compounds, nucleotide analogs, nucleoside analogs, immunoglobulins, immunomodulators, hepatoprotectants, anti-inflammatory agents, antibiotics, antivirals, and anti-infective compounds. In a further embodiment, the at least one biologically active agent is a pegylated interferon. In a yet further embodiment the pegylated interferon is a pegylated interferon-alpha and the compound is

[(R)-5-cyano-8-methyl-1-propyl-1,3,4,9-tetrahydropyrano[3,4-b]indol-1-yl]acetic acid. In a yet further embodiment the pegylated interferon is a pegylated interferon-alpha and the compound is [(R)-5-cyano-6-fluoro-8-methyl-1-propyl-1,3,4,9tetrahydropyrano[3,4-b]indol-1-yl]acetic acid.

The present invention further provides a method of treating or preventing a Hepatitis C viral infection in a mammal comprising providing the mammal with an effective amount of at least one pharmaceutical composition, wherein the at least one pharmaceutical composition includes a compound of a formula:

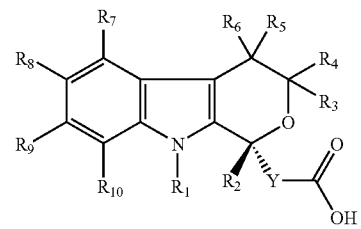

wherein:

$R_1$ is H;
$R_2$ is H, or a straight chain alkyl of 1 to 4 carbon atoms;
$R_3$–$R_6$ are H;

$R_7$–$R_{10}$ are independently H, a straight chain alkyl of 1 to 3 carbon, F, Cl, or CN;

Y is $CH_2$; and a pharmaceutically acceptable carrier.

The method of the present invention further comprises providing the mammal with an effective amount of at least one biologically active agent.

In an embodiment of the method of the present invention, the at least one biologically active agent is provided prior to the at least one pharmaceutical composition, concurrently with the at least one pharmaceutical composition or after the at least one pharmaceutical composition. In a further embodiment of the method of the present invention, the compound is a crystalline form or a pharmaceutically acceptable salt thereof.

In a further embodiment the at least one biologically active agent is selected from the group consisting of interferon, a pegylated interferon, ribavirin, protease inhibitors, polymerase inhibitors, small interfering RNA compounds, anti-sense compounds, nucleotide analogs, nucleoside analogs, immunoglobulins, immunomodulators, hepatoprotectants, anti-inflammatory agents, antibiotics, antivirals, and anti-infective compounds. In a further embodiment the at least one biologically active agent is a pegylated interferon. In a yet further embodiment the pegylated interferon is a pegylated interferon-alpha and the compound is

[(R)-5-cyano-8-methyl-1-propyl-1,3,4,9-tetrahydropyrano[3,4-b]indol-1-yl]acetic acid. In a yet further embodiment the pegylated interferon is a pegylated interferon-alpha and the compound is [(R)-5-cyano-6-fluoro-8methyl-1-propyl-1,3,4,9-tetrahydropyrano[3,4-b]indol-1-yl]acetic acid.

The present invention also provides a method of inhibiting replication of a Hepatitis C virus comprising contacting the Hepatitis C virus with an effective amount of at least one pharmaceutical composition, wherein the at least one pharmaceutical composition includes a compound of a formula:

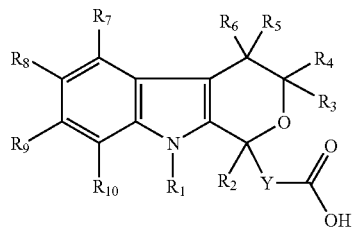

wherein:
  $R_1$ is H, a straight chain alkyl of 1 to 8 carbon atoms, a branched alkyl of 3 to 12 carbon atoms, a cycloalkyl of 3 to 12 carbon atoms, an alkenyl of 2 to 7 carbon atoms, an alkynyl of 2 to 7 carbon atoms, or an arylalkyl or an alkylaryl of 7 to 12 carbon atoms;
  $R_2$ is H, a straight chain alkyl of 1 to 12 carbon atoms, a branched alkyl of 3 to 12 carbon atoms, a cycloalkyl of 3 to 12 carbon atoms, an alkenyl of 2 to 7 carbon atoms, an alkynyl of 2 to 7 carbon atoms, an alkoxyalkyl of 2 to 12 carbon atoms, an arylalkyl or alkylaryl of 7 to 12 carbon atoms, a cyanoalkyl of 1 to 8 carbon atoms, an alkylthioalkyl of 2 to 16 carbon atoms, a cycloalkylalkyl of 4 to 24 carbon atoms, a substituted or unsubstituted aryl, or a heteroaryl;
  $R_3$–$R_6$ are independently H, a straight chain alkyl of 1 to 8 carbon atoms, a branched alkyl of 3 to 12 carbon atoms, a cycloalkyl of 3 to 12 carbon atoms, an alkenyl of 2 to 7 carbon atoms, a substituted or unsubstituted aryl, furanylmethyl, arylalkyl or alkylaryl of 7 to 12 carbon atoms, alkynyl of 2 to 7 carbon atoms, or $R_5$ and $R_6$ together with the ring carbon atom to which they are attached form a carbonyl group;
  $R_7$–$R_{10}$ are independently H, a straight chain alkyl of 1 to 8 carbon atoms, a branched alkyl of 3 to 12 carbons atoms, a cycloalkyl of 3 to 12 carbon atoms, an alkenyl of 2 to 7 carbon atoms, a substituted or unsubstituted aryl, a substituted or unsubstituted heteroaryl, furanylmethyl, arylalkyl or alkylaryl of 7 to 12 carbon atoms, alkynyl of 2 to 7 carbon atoms, phenylalkynyl, alkoxy of 1 to 8 carbon atoms, arylalkoxy of 7 to 12 carbon atoms, fluoroalkoxy of 1 to 12 carbon atoms, alkylthio of 1 to 8 carbon atoms, trifluoromethoxy, trifluoroethoxy, trifluoromethylthio, trifluoroethylthio, acyl of 1 to 7 carbon atoms, COOH, COO-alkyl, $CONR_{11}R_{12}$, F, Cl, Br, I, CN, $CF_3$, $NO_2$, alkylsulfinyl of 1 to 8 carbon atoms, alkylsulfonyl of 1 to 6 carbon atoms, pyrrolidinyl, or thiazolidinyl;
  $R_{11}$–$R_{12}$ are independently H, straight chain alkyl of 1 to 8 carbon atoms, branched alkyl of 3 to 12 carbon atoms, cycloalkyl of 3 to 12 carbon atoms, a substituted or unsubstituted aryl or heteroaryl;
  Y is a bond, $CH_2$, $CH_2CH_2$, aryl, or $R_2$ and Y together with the ring carbon atom to which they are attached may additionally form a spirocyclic cycloalkyl ring of 3 to 8 carbon atoms; and a pharmaceutically acceptable carrier.

The method of the present invention further comprises providing the mammal with an effective amount of at least one biologically active agent.

In an embodiment of the method of the present invention, the at least one biologically active agent is provided prior to the at least one pharmaceutical composition, concurrently with the at least one pharmaceutical composition or after the at least one pharmaceutical composition. In a further embodiment of the method of the present invention, the compound is a crystalline form or a pharmaceutically acceptable salt thereof.

In a further embodiment the at least one biologically active agent is selected from the group consisting of interferon, a pegylated interferon, ribavirin, protease inhibitors, polymerase inhibitors, small interfering RNA compounds, anti-sense compounds, nucleotide analogs, nucleoside analogs, immunoglobulins, immunomodulators, hepatoprotectants, anti-inflammatory agents, antibiotics, antivirals, and anti-infective compounds. In a further embodiment the at least one biologically active agent is a pegylated interferon. In a yet further embodiment the pegylated interferon is a pegylated interferon-alpha and the compound is

[(R)-5-cyano-8-methyl-1-propyl-1,3,4,9-tetrahydropyrano[3,4-b]indol-1-yl]acetic acid. In a yet further embodiment the pegylated interferon is a pegylated interferon-alpha and the compound is [(R)-5-cyano-6-fluoro-8methyl-1-propyl-1,3,4,9-tetrahydropyrano[3,4-b]indol-1-yl]acetic acid.

The present invention further provides a method of inhibiting replication of a Hepatitis C virus comprising contacting the Hepatitis C virus with an effective amount of at least one pharmaceutical composition, wherein the at least one pharmaceutical composition includes a compound of a formula:

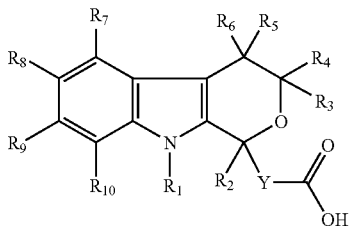

wherein:
- R₁ is H, a straight chain alkyl of 1 to 6 carbon atoms, a branched alkyl of 3 to 10 carbon atoms, a cycloalkyl of 3 to 10 carbon atoms, an alkenyl of 2 to 7 carbon atoms, an alkynyl of 2 to 7 carbon atoms, or an arylalkyl of 7 to 12 carbon atoms;
- R₂ is H, a straight chain alkyl of 1 to 12 carbon atoms, a branched alkyl of 3 to 10 carbon atoms, a cycloalkyl of 3 to 10 carbon atoms, an alkenyl of 2 to 7 carbon atoms, an alkynyl of 2 to 7 carbon atoms, an alkoxyalkyl of 2 to 12 carbon atoms, an arylalkyl of 7 to 12 carbon atoms, an unsubstituted aryl or an aryl substituted with one to four groups, or heteroaryl;
- R₃–R₆ are independently H, a straight chain alkyl of 1 to 6 carbon atoms, a branched alkyl of 3 to 10 carbons atoms, a cycloalkyl of 3 to 10 carbon atoms, an alkenyl of 2 to 7 carbon atoms, an unsubstituted aryl or an aryl substituted with one to four groups, furanylmethyl, an arylalkyl of 7 to 12 carbon atoms, an alkynyl of 2 to 7 carbon atoms, or R₅ and R₆ together with the ring carbon atom to which they are attached form a carbonyl group;
- R₇–R₁₀ are independently H, a straight chain alkyl of 1 to 6 carbon atoms, a branched alkyl of 3 to 10 carbons atoms, a cycloalkyl of 3 to 10 carbon atoms, an alkenyl of 2 to 7 carbon atoms, an unsubstituted aryl or an aryl substituted with one to four groups, an unsubstituted heteroaryl or a heteroaryl substituted with one to three groups, furanylmethyl, an arylalkyl of 7 to 12 carbon atoms, an alkynyl of 2 to 7 carbon atoms, phenylalkynyl, an alkoxy of 1 to 6 carbon atoms, an arylalkoxy of 7 to 12 carbon atoms, a fluoroalkoxy of 1 to 12 carbon atoms, an alkylthio of 1 to 6 carbon atoms, trifluoromethoxy, trifluoroethoxy, trifluoromethylthio, trifluoroethylthio, an acyl of 1 to 7 carbon atoms, a carboxy group, CONR₁₁R₁₂, F, Cl, Br, I, CN, CF₃, NO₂, an alkylsulfinyl of 1 to 6 carbon atoms, an alkylsulfonyl of 1 to 6 carbon atoms;
- R₁₁–R₁₂ are independently H, a straight chain alkyl of 1 to 6 carbon atoms, a branched alkyl of 3 to 10 carbon atoms, a cycloalkyl of 3 to 10 carbon atoms, an aryl substituted with one to four groups, an unsubstituted heteroaryl or a heteroaryl substituted with one to three groups;
- Y is CH₂, CH₂CH₂, or aryl; and
- a pharmaceutically acceptable carrier.

The method of the present invention further comprises providing the mammal with an effective amount of at least one biologically active agent.

In an embodiment of the method of the present invention, the at least one biologically active agent is provided prior to the at least one pharmaceutical composition, concurrently with the at least one pharmaceutical composition or after the at least one pharmaceutical composition. In a further embodiment of the method of the present invention, the compound is a crystalline form or a pharmaceutically acceptable salt thereof.

In a further embodiment of the method of the present invention, the at least one biologically active agent is selected from the group consisting of interferon, a pegylated interferon, ribavirin, protease inhibitors, polymerase inhibitors, small interfering RNA compounds, anti-sense compounds, nucleotide analogs, nucleoside analogs, immunoglobulins, immunomodulators, hepatoprotectants, anti-inflammatory agents, antibiotics, antivirals, and anti-infective compounds. In a further embodiment, the at least one biologically active agent is a pegylated interferon. In a yet further embodiment, the pegylated interferon is a pegylated interferon-alpha and the compound is
- [(R)-5-cyano-8-methyl-1-propyl-1,3,4,9-tetrahydropyrano[3,4-b]indol-1-yl]acetic acid. In a yet further embodiment the pegylated interferon is a pegylated interferon-alpha and the compound is [(R)-5-cyano-6-fluoro-8-methyl-1-propyl-1,3,4,9-tetrahydropyrano[3,4-b]indol-1-yl]acetic acid.

The compounds of the present invention or precursors thereof and their isomers and pharmaceutically acceptable salts thereof are also useful in treating and preventing viral infections, in particular hepatitis C infection, and diseases in living hosts when used in combination with each other (i.e. pharmaceutical compositions comprising the compounds are administered concurrently with each or sequentially, in either order). The combination of compounds provided herein may further be provided to a subject in respective pharmaceutical compositions, concurrently with or sequentially to other biologically active agents, including but not limited to the group consisting of interferon, a pegylated interferon, ribavirin, protease inhibitors, polymerase inhibitors, small interfering RNA compounds, anti-sense compounds, nucleotide analogs, nucleoside analogs, immunoglobulins, immunomodulators, hepatoprotectants, anti-inflammatory agents, antibiotics, antivirals, and anti-infective compounds. The present invention further provides combination therapy with one or more pyranoindole derivatives, i.e., at least two pharmaceutical compositions, each comprising a different compound of the present invention, are provided to a subject in need thereof either concurrently with each other or sequentially, and such therapy may further comprise providing concurrently or sequentially other medicinal agents or potentiators, such as acyclovir, famicyclovir, valgancyclovir and related compounds, ribavirin and related compounds, amantadine and related compounds, various interferons such as, for example, interferon-alpha, interferon-beta, interferon-gamma and the like, as well as alternative forms of interferons such as pegylated interferons. Additionally, combinations of, for example ribavirin and interferon, may be administered as an additional combination for a multiple combination therapy with at least one of the compounds of the present invention.

The combination therapy with any of the above-described biologically active agents may also be sequential, that is the treatment with a first pharmaceutical composition comprising a compound of the invention followed by treatment with a second pharmaceutical composition comprising a second compound of the invention, wherein the second compound is different than the first compound; alternatively, treatment may be with both two or more pharmaceutical compositions, wherein each pharmaceutical composition comprises a different compound of the invention, at the same time. The sequential therapy can be within a reasonable time after the completion of the first therapy with the pharmaceutical composition. Treatment with the respective pharmaceutical compositions, each comprising a different compound of the present invention, at the same time may be provided in the same daily dose or in separate doses. Combination therapy may also be provided wherein a pharmaceutical composition comprising at least one compound of the present invention is administered in a composition further comprising at least one biologically active agent, i.e. in a single dose. The dosages for both concurrent and sequential combination therapy (for combined pharmaceutical compositions comprising at least two compounds of the invention or compositions comprising at least one compound of the invention and at least one biologically active agent), will depend on absorption, distribution, metabolism and excretion rates of the components of the pharmaceutical composition as well as other factors known to one of skill in the art. Dosage values of the pharmaceutical composition will also vary with the severity of the condition to be alleviated. It is to be further understood that for any particular subject, specific dosage regimens and schedules may be adjusted over time according to the individual's need and the professional judgment of the person administering or supervising the administration of the pharmaceutical compositions.

In a further embodiment, the compounds of the invention may be used for the treatment of HCV in humans in combination therapy mode with other inhibitors of the HCV polymerase.

In yet a further embodiment, the compounds of the present invention may be used for the treatment of HCV in humans in combination therapy mode with other inhibitors of the HCV life cycle such as, for example, inhibitors of HCV cell attachment or virus entry, HCV translation, HCV RNA transcription or replication, HCV maturation, assembly or virus release, or inhibitors of HCV enzyme activities such as the HCV nucleotidyl transferase, helicase, protease or polymerase.

It is intended that combination therapies of the pharmaceutical compositions include any chemically compatible combination of a compound of this inventive group with other compounds of the inventive group or other compounds outside of the inventive group, as long as the combination does not eliminate the antiviral activity of the compound of this inventive group or the anti-viral activity of the pharmaceutical composition itself.

The term "interferon-alpha" as used herein means the family of highly homologous species-specific proteins that inhibit viral replication and cellular proliferation and modulate immune response. Typical suitable interferon-alphas include, but are not limited to, recombinant interferon alpha-2b such as INTRON-A INTERFERON available from Schering Corporation, Kenilworth, N.J., recombinant interferon alpha-2a such as Roferon interferon available from Hofman-La Roche, Nutley, N.J., a recombinant interferon alpha-2C, such as BEROFOR ALPHA 2 INTERFERON available from Boehringer Ingelheim Pharmaceutical, Inc., Ridgefield, Conn., interferon alpha-n1, a purified blend of natural alpha interferons such as SUMIFERON available from Sumitomo, Japan or as Wellferon interferon alpha-n1 (INS) available from Glaxo-Wellcome Ltd., London, Great Britain, or a consensus alpha interferon such as those described in U.S. Pat. Nos. 4,897,471 and 4,695,623 (the contents of which are hereby incorporated by reference in their entireties, specifically examples 7, 8 or 9 thereof) and the specific product available from Amgen, Inc., Newbury Park, Calif., or interferon alpha-n3 a mixture of natural interferons made by Interferon Sciences and available from the Purdue Frederick Co., Norwalk, Conn., under the ALFERON trademark. The use of interferon alpha-2a or alpha 2b is preferred. Since interferon alpha 2b, among all interferons, has the broadest approval throughout the world for treating chronic hepatitis C infection, it is most preferred. The manufacture of interferon alpha 2b is described in U.S. Pat. No. 4,503,901.

The term "pegylated interferon" as used herein means polyethylene glycol modified conjugates of interferon, preferably interferon alpha-2a and alpha-2b. The preferred polyethylene-glycol-interferon alpha-2b conjugate is PEG.sub.12000-interferon alpha 2b. The phrase "PEG.sub.12000-IFN alpha" as used herein means conjugates such as are prepared according to the methods of International Application No. WO 95/13090 and containing urethane linkages between the interferon alpha-2a or alpha-2b amino groups and polyethylene glycol having an average molecular weight of 12000.

The following experimental details are set forth to aid in an understanding of the invention, and are not intended, and should not be construed, to limit in any way the invention set forth in the claims that follow thereafter.

DETAILED DESCRIPTION OF THE INVENTION

The compounds of the present invention can be readily prepared according to the following reaction schemes or modification thereof. In the following reaction schemes $R_1$, $R_2$, $R_3$, $R_4$, $R_5$, $R_6$, $R_7$, $R_8$, $R_9$, or $R_{10}$, $R_{11}$, $R_{12}$ and Y are selected from the groups defined above.

Preferred compounds of the present invention can be synthesized as described in the schemes below (Scheme 1 to 10). Starting material in Scheme 3 is readily available from a commercial source (Lancaster Synthesis Inc., Lancaster, U.K., product no. 15472).

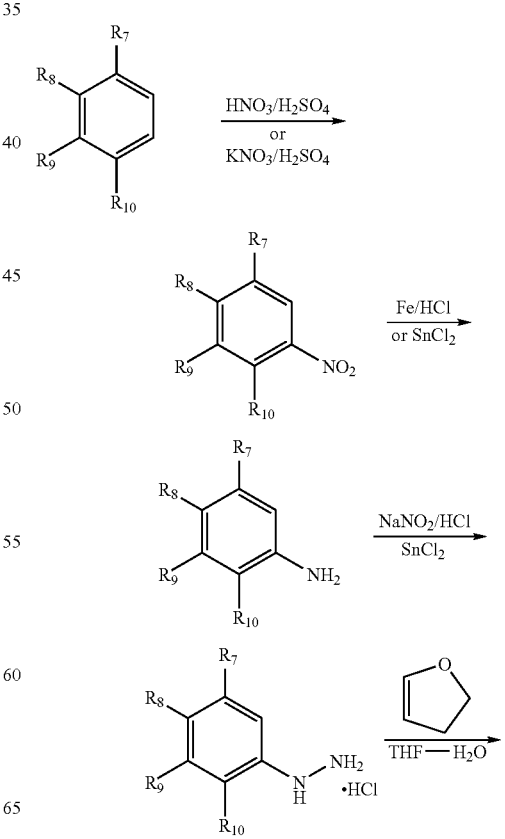

Scheme 1

-continued
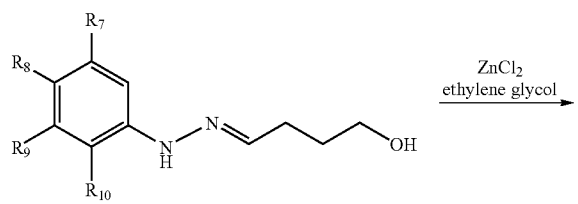
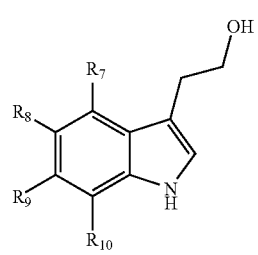
Scheme 2
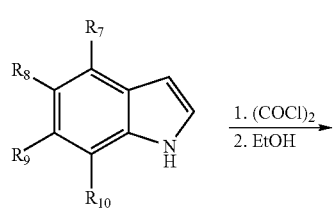
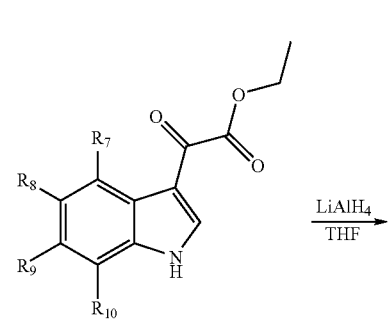
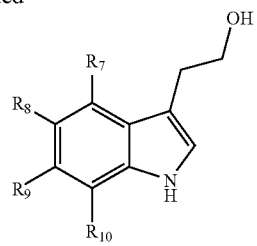
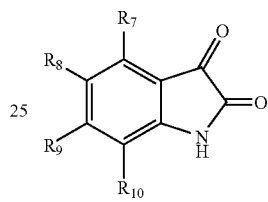
Scheme 3
Scheme 4
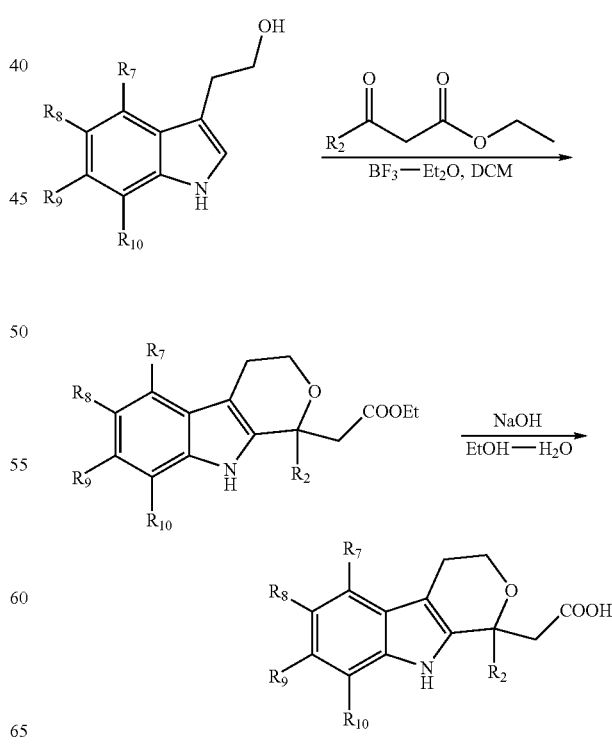

Scheme 5
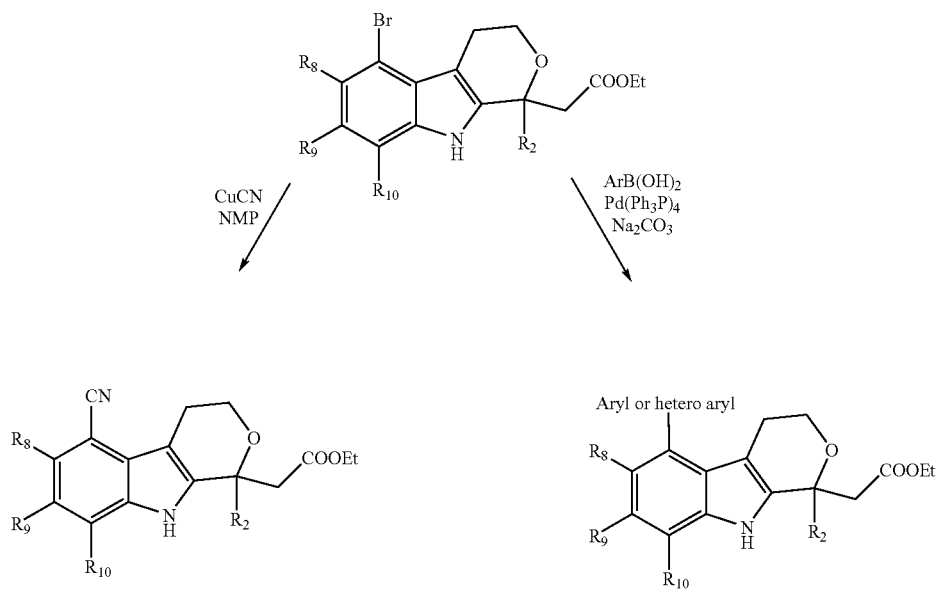
Scheme 6
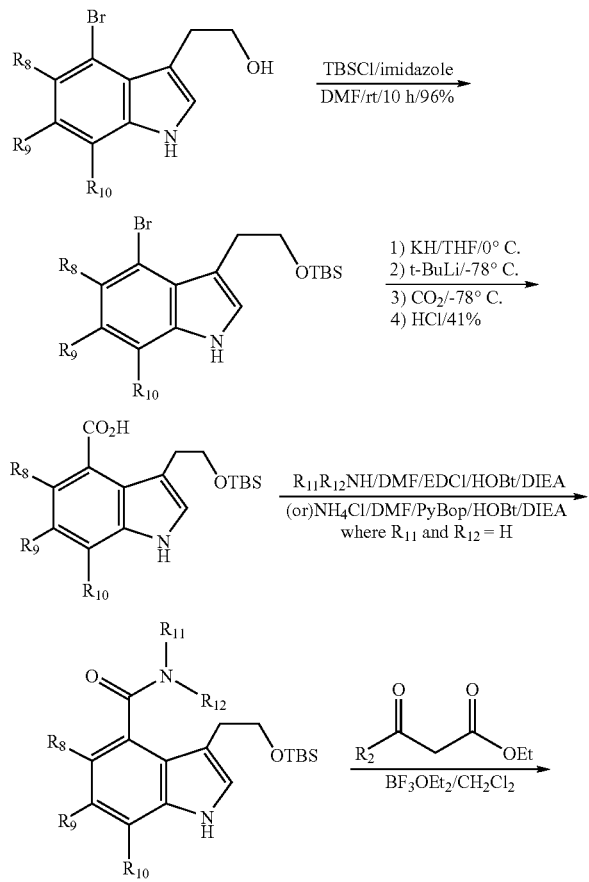

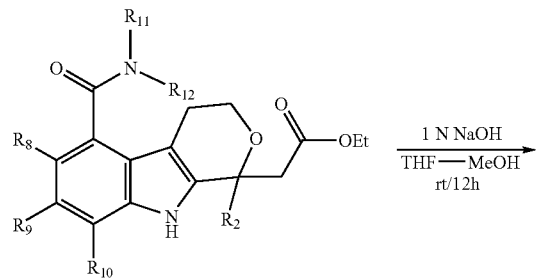
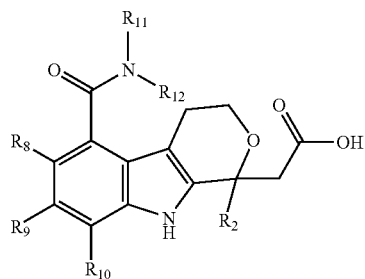
Scheme 7
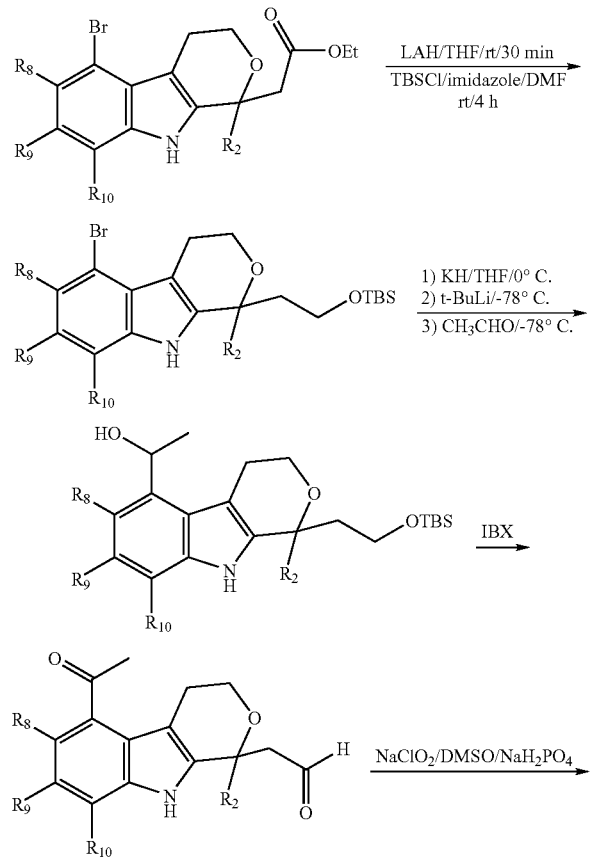

-continued
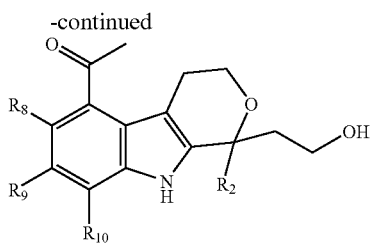
Scheme 8
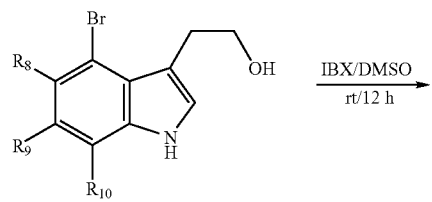
Scheme 9
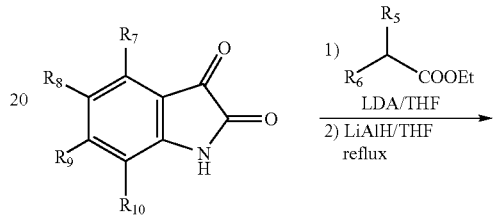
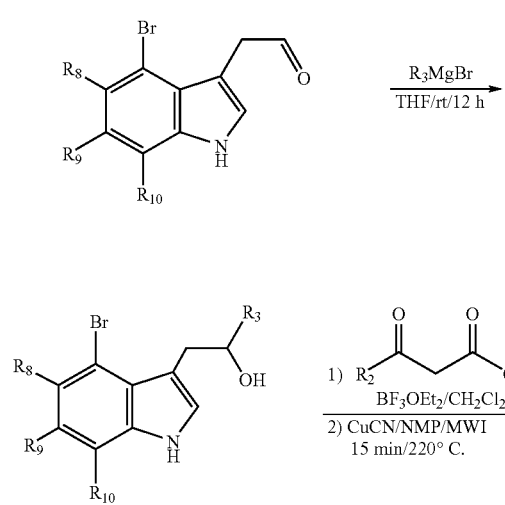
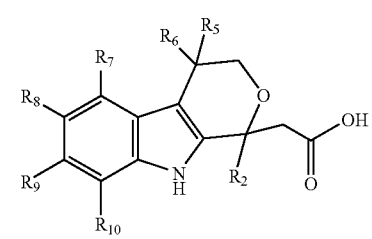
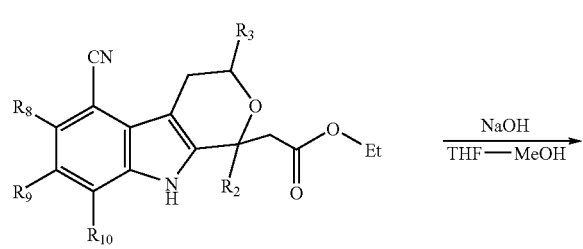
Scheme 10
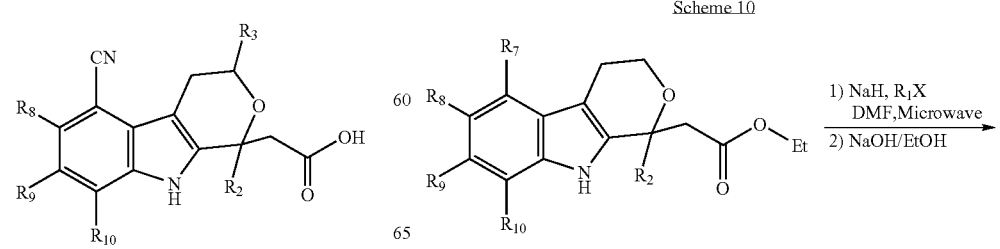

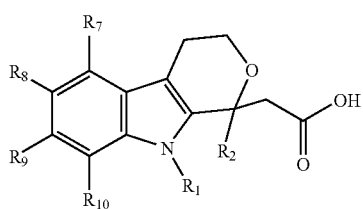
Scheme 11
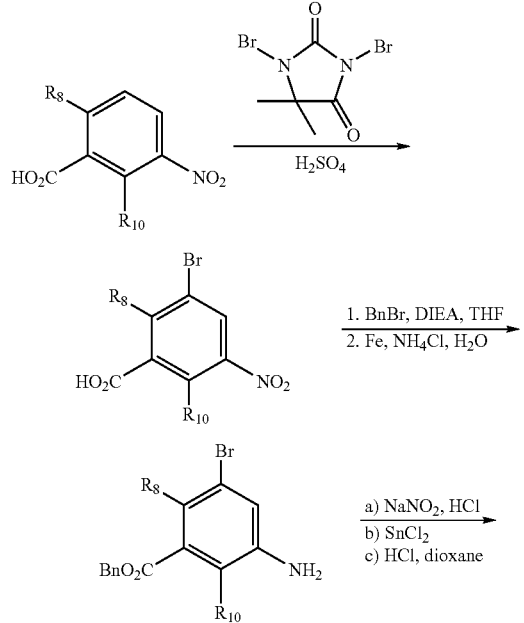
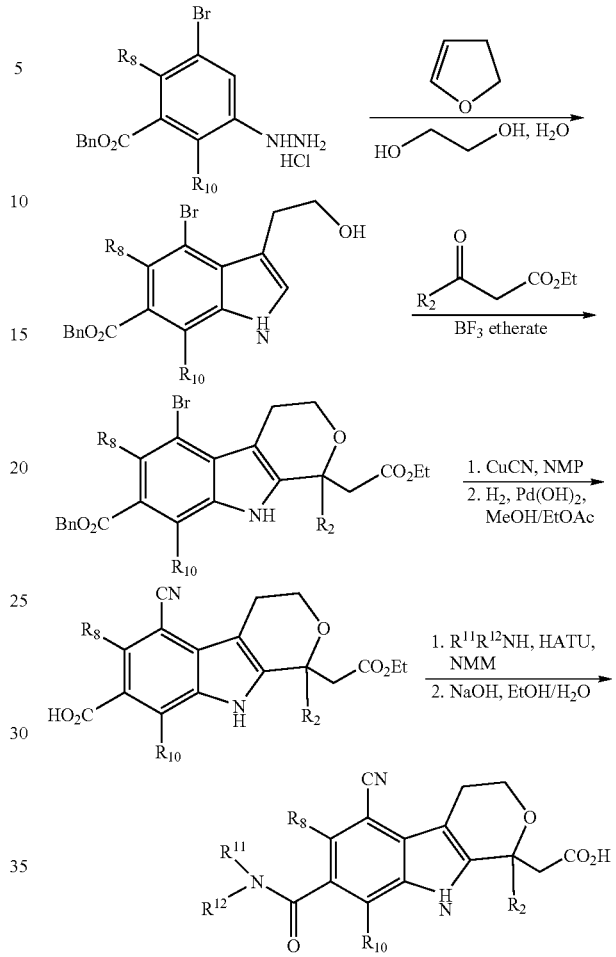
Scheme 12
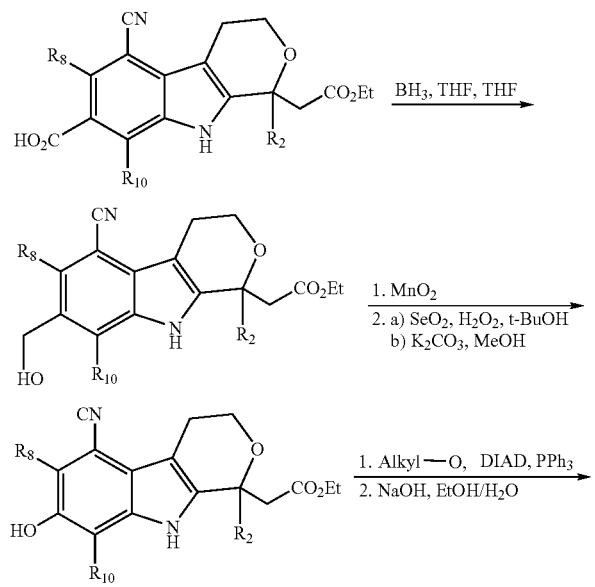

-continued

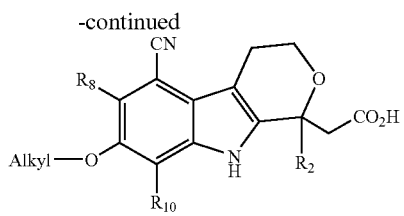

The ability of the compounds of the present invention to inhibit Hepatitis C Polymerase was established by the following experimental procedure:

NS5B from the BK strain (genotype 1b) is expressed in *E. coli* as a protein in which the 21 C-terminal amino acids are replaced with a short linker and a hexahistidine tag (GSHHHHHH). The purified protein is mixed with radioactive nucleotides and allowed to replicate a heteropolymeric RNA substrate, primed by an endogenous short hairpin, resulting in an approximately 760 nt product. The radioactive product is captured on a filter and quantitated after removal of the unincorporated nucleotides.

Reagents:
10 mM uridine 5'-triphosphate (UTP) (Promega # p116B)
10 mM adenine 5'-triphosphate (ATP) (Promega # p113B)
10 mM cytidine 5'-triphosphate (CTP) (Promega # p114B)
10 mM guanine 5'-triphosphate (GTP) (Promega # p115B)
Bovine Serum Albumin (BSA) 10 mg/ml NEB (100× at 10 mg/ml) #007-BSA
RNasein (Promega #N251X) 40 U/µl
A-[33P]-GTP (NEN-easytides NEG/606H 3000 Ci/mmol, 370 MBq/ml, 10 mCi/ml)
Falcon polypropylene 96 well plates (Becton Dickinson # 351190)
Millipore Multiscreen assay system-96 well-filtration plate #MADE NOB 50
Optiphase Supermix (Wallac) formulated by Fisher
Millipore Multiscreen liner for use in microbeta 1450-106 casette [(Wallac) Perkin Elmer #1450-433]
1 M(N-[2-hydroxyethyl]piperazine-N'-[2-ethanesulfonic acid]) (HEPES), pH 7.3
Amersham Pharmacia Biotec (US16924-500 ml)
1 M $MgCl_2$ (SIGMA #M1028)
Dithiothreitol (DTT) (solid) (SIGMA #D9779)
RNase free water (GIBCO-BRL #10977-023)
Dimethyl sulfoxide (Aldrich #27685-5)
Basilen Blue (Sigma, B5520)
0.5M ethylenediaminetetraacetic acid (EDTA), pH 8 (GIBCO-BRL #15575-020)
Dibasic sodium phosphate (7-hydrate) ($Na_2HPO_4 \cdot 7H_2O$; Baker#3824-07)
Phosphoric acid (Baker, #0262.02)

Further reagent preparation:
0.5 M Na Phosphate buffer. Per liter, weigh 134 gr $Na_2HPO_4 \cdot 7H_2O$, add water to 900 ml. Adjust pH to 7.0 with phosphoric acid. Top off with water to 1 L.
Dilute nucleotides 1:1000 to 10 µM (GTP and CTP) or 1:100 to 100 µM (ATP and UTP) into RNase free water.

Procedure:
(1) Compounds 10 µl at 10 µg/ml in 15% dimethylsulfoxide (DMSO)
When starting from 100 µg/ml compound stock in 1% DMSO:
Dispense 5 µl 30% DMSO per well
Dispense 5 µl compound (100 µg/ml) per well.
When starting from 50 µg/ml compound stock in 15% DMSO:
Add 10 µl compound per well.
(2) Enzyme Mix:

| Stock | Final Conc (in 50 µl assay volume) | Per 20 µl mix (1 reaction) | Per 600 reactions |
|---|---|---|---|
| DEPC $H_2O$ | | 17.06 µl | 10236 µl |
| 1 M HEPES, pH 7.5 | 20 Mm | 0.5 µl | 300 µl |
| 1 M $MgCl_2$ | 5 mM | 0.25 µl | 150 µl |
| 100 mM DTT | 1 mM | 0.5 µl | 300 µl |
| 100 µM UTP | 0.5 µM | 0.25 µl | 150 µl |
| 100 µM ATP | 1 µM | 0.5 µl | 300 µl |
| 10 µM CTP | 0.08 µM | 0.4 µl | 240 µl |
| 10 µM GTP | 0.025 µM | 0.125 µl | 75 µl |
| BSA, 10 mg/ml | 0.05 mg/ml | 0.25 µl | 150 µl |
| HCV RdRp NS5B d21BK (500 µg/ml or ~7.5µM) | 24 nM | 0.16 µl | 96 µl |
| Total: | | 20 µl | 12 ml |

Add 20 µl enzyme mix into each well of the assay plate. Incubate compound and enzyme at room temperature for 15 minutes (3) Template mix—prepare ahead
Spin down a tube of RNA (5 µg/tube stored in 75% ethanol and 0.3 M sodium acetate) in a microcentrifuge for 20 minutes at 4° C. One tube is enough for 1–1.5 plates. Remove as much ethanol from the tube as possible by inverting the tube. Be gentle, pellet RNA may not adhere to the tube. Vacuum dry the RNA. Resuspend the RNA by adding 1 ml of DEPC water, close the cap of the tube tightly. To dissolve RNA, incubate RNA solution on ice for ~60 minutes and gently vortex. Spin briefly to ensure all RNA solution is down to the bottom of the tube before opening cap. Gently transfer RNA solution into a 5 ml or larger tube. Add another 3 ml of DEPC water (total 4 ml of volume).
Add the following volumes of reagents

| Stock | Final concentration | Per 20 µl mix (1 reaction) | Per 600 reactions |
|---|---|---|---|
| RNAse-free water | | 2.98 µl | 1788 µl |
| HEPES, 1M | 20 mM | 0.5 µl | 300 µl |
| RNase Inhibitor | 0.4 µ/µl | 0.5 µl | 300 µl |

-continued

| Stock | Final concentration | Per 20 μl mix (1 reaction) | Per 600 reactions |
|---|---|---|---|
| (40 U/μl) | | | |
| 33P-GTP 3000 Ci/mmol, 10 μCi/μl (3.3 μM) | 0.025 μM | 0.0125 μl | 7.5 μl |
| POF RNA template | 3 nM | 16 μl | 9600 μl |

Add 20 μl template mix per reaction (i.e. 20 ng of pOF per reaction or ~3 nM)

(4) Incubate reaction at room temperature (22–25° C.) for 2 hours.
(5) Stop reaction by adding 50 μl of 170 mM EDTA. Final concentration of EDTA is 85 mM.
(6) Prewet filters of Millipore multiscreen assay plate by adding 200 μl of 0.5 M sodium phosphate buffer, pH 7.0 into each well. Let stand at room temperature for 2–3 minutes.
(7) Place the multiscreen filter plate onto a Millipore Manifold and turn on vacuum to allow buffer to flow through. Turn off vacuum. Transfer 80 μl of the reaction product into each well of the filter plate. Let stand for 2–3 minutes. Turn on vacuum to filter reaction product.
(8) Turn off vacuum. Add 200 μl of 0.5 M sodium phosphate buffer, pH 7.0 into each well to wash filter. Turn on vacuum.
Repeat step (8) three more times.
(9) Remove polypropylene bottom. Spot dry filter at the bottom with paper towel. Air dry filter plate on a bench for 1 hour. Add 40 μl Super Mix scintillant. Seal top of the plate with a tape. Place plate into a Packard carrier or micro-beta carrier.
(10) Count plate using a Packard Topcount or micro-beta counter. Count (for example using Program 10) for $^{33}$P in Top count or $^{33}$P program in micro-beta.

Percent inhibition is calculated after background subtraction as a percent reduction of activity relative to the positive control (average value of the plate excluding the negative controls). For the primary screen hits were chosen as showing >75% inhibition.

See, Ferrari et al. 1999. J. Virology 73:1649–1654: "Characterization of soluble Hepatitis C virus RNA-dependent RNA polymerase expressed in *E. coli* and Takamizawa et al 1991" and J. Virology 65:1105–1113: "Structure and characterization of the Hepatitis C virus genome isolated from human carriers," both references are hereby incorporated by reference.

The compounds of the present invention inhibited Hepatitis C polymerase as summarized in Table 1 A and B:

TABLE 1A

| Example | HCV pol BK IC$_{50}$ (μM) | HCV pol % inh at 20 μM |
|---|---|---|
| 1 | 0.5 | — |
| 2 | 0.33 | — |
| 3 | 2.4 | — |
| 4 | 1.0 | — |
| 5 | 0.44 | — |
| 6 | 5.7 | — |
| 7 | 0.2 | — |
| 8 | 0.06 | — |
| 9 | 1.1 | — |
| 10 | 0.08 | — |
| 11 | 0.08 | — |
| 12 | 0.6 | — |
| 13 | >20 | 23 |
| 14 | 11 | 75 |
| 15 | >20 | 7 |
| 16 | >20 | <5 |
| 17 | >20 | <5 |
| 18 | >20 | <5 |
| 19 | >20 | 6 |
| 20 | >20 | 21 |
| 21 | >20 | 58 |
| 22 | 5 | 70 |
| 23 | >20 | 12 |
| 24 | >20 | <5 |
| 25 | >20 | 33 |
| 26 | >20 | <5 |
| 27 | >20 | 3 |
| 28 | >20 | <5 |
| 29 | >20 | <5 |
| 30 | >20 | <5 |
| 31 | >20 | 12 |
| 32 | >20 | <5 |
| 33 | >20 | <5 |
| 34 | >20 | 5 |
| 35 | >20 | 35 |
| 36 | >20 | 4 |
| 37 | >20 | 28 |
| 38 | >20 | 11 |
| 39 | >20 | 7 |
| 40 | >20 | 27 |
| 41 | >20 | 13 |
| 42 | >20 | 31 |
| 43 | >20 | 83 |
| 44 | >20 | 41 |
| 45 | >20 | 14 |
| 46 | >20 | 15 |
| 47 | >20 | 15 |
| 48 | >20 | 18 |
| 49 | >20 | <5 |
| 50 | >20 | 34 |
| 51 | 7 | 84 |
| 52 | >20 | 11 |
| 53 | 13 | 62 |
| 54 | >20 | 6 |
| 55 | >20 | <5 |
| 56 | >20 | 3 |
| 57 | 3 | 56 |
| 58 | 6.9 | 78 |
| 59 | >20 | 23 |
| 60 | >20 | 15 |
| 61 | >20 | 18 |
| 62 | >20 | 32 |
| 63 | >20 | 30 |
| 64 | >20 | 18 |
| 65 | >20 | 27 |
| 66 | >20 | 28 |
| 67 | 0.76 | 78 |
| 68 | 10.3 | 61 |
| 69 | 5.5 | — |
| 70 | >5 | 22 |
| 71 | >5 | 45 |
| 72 | >20 | 45 |
| 73 | >20 | 22 |
| 74 | 17.9 | 69 |
| 75 | >20 | 17 |
| 76 | >20 | 29 |
| 77 | >20 | 16 |
| 78 | >20 | 26 |
| 79 | >20 | 40 |
| 80 | >20 | 35 |
| 81 | >20 | 27 |
| 82 | 9.2 | 73 |
| 83 | >20 | 41 |
| 84 | 19.7 | 46 |
| 85 | >20 | 18 |

TABLE 1A-continued

| Example | HCV pol BK IC$_{50}$ (μM) | HCV pol % inh at 20 μM |
|---|---|---|
| 86 | >20 | 20 |
| 87 | >20 | 42 |
| 88 | >20 | 30 |
| 89 | >20 | 36 |
| 90 | >20 | 2 |
| 91 | >20 | <5 |
| 92 | >20 | 35 |
| 93 | >20 | 64 |
| 94 | >20 | 33 |
| 95 | 14.4 | 68 |
| 96 | >20 | 37 |
| 97 | >20 | 21 |
| 98 | >20 | 44 |
| 99 | >20 | 32 |
| 100 | >20 | 54 |
| 101 | 1.5 | 89 |
| 102 | 21.7 | 51 |
| 103 | 14.4 | 60 |
| 104 | >20 | <5 |
| 105 | >5 | 57 |
| 106 | 2.3 | 71 |
| 107 | 19.1 | 50 |
| 108 | 11.2 | 66 |
| 109 | 0.18 | 87 |
| 110 | 6.4 | 63 |
| 111 | 4.1 | 66 |
| 112 | >20 | 34 |
| 113 | 0.26 | 35 |
| 114 | >20 | 57 |
| 115 | >20 | 40 |
| 116 | >20 | 34 |
| 117 | 9.6 | 39 |
| 118 | >20 | 10 |
| 119 | >20 | 31 |
| 120 | >20 | 33 |
| 121 | >20 | <5 |
| 122 | >20 | 5 |
| 123 | >20 | 51 |
| 124 | 6.7 | 61 |
| 125 | >20 | 73 |
| 126 | >20 | 35 |
| 127 | >20 | 24 |
| 128 | >20 | 70 |
| 129 | >20 | 45 |
| 130 | 5.5 | 77 |
| 131 | 0.32 | 93 |
| 132 | 9.5 | 78 |
| 133 | 0.7 | 88 |
| 134 | >20 | 28 |
| 135 | >20 | 55 |
| 136 | 4.3 | 81 |
| 137 | >20 | 5 |
| 138 | >20 | 38 |
| 139 | 8.3 | 40 |
| 140 | >20 | 28 |
| 141 | 1.4 | 79 |
| 142 | 19.8 | 39 |
| 143 | 16.5 | 56 |
| 144 | 6.0 | 73 |
| 145 | >20 | 20 |
| 146 | >20 | 45 |
| 147 | 10 | 34 |
| 148 | >20 | 47 |
| 149 | 16 | <11 |
| 150 | 9 | <37 |
| 151 | >20 | 34 |
| 152 | 1.0 | 87 |
| 153 | 0.3 | 93 |
| 154 | 22.4 | 22 |
| 155 | 0.47 | 84 |
| 156 | 0.08 | 88 |
| 157 | 0.6 | 89 |
| 158 | 0.28 | 91 |
| 159 | >20 | 36 |
| 160 | >20 | 15 |
| 161 | 0.3 | 74 |
| 162 | 2.4 | 73 |
| 163 | >10 | 28 |
| 164 | 2 | 77 |
| 165 | 0.6 | 89 |
| 166 | 3.7 | 55 |
| 167 | 3 | 80 |
| 168 | >10 | 4 |
| 169 | 0.22 | 82 |
| 170 | 1 | 53 |
| 171 | >10 | 3 |
| 172 | 1.7 | 74 |
| 173 | >5 | 19 |
| 174 | >5 | 70 |
| 175 | 0.5 | 84 |
| 176 | >5 | 49 |
| 177 | 4 | 70 |
| 178 | >5 | <32 |
| 179 | >5 | 15 |
| 180 | 0.81 | 92 |
| 181 | >5 | 14 |
| 182 | >5 | 55 |
| 183 | 0.59 | 88 |
| 184 | >5 | 39 |
| 185 | 4 | 69 |
| 186 | >5 | 2 |
| 187 | >5 | 61 |
| 188 | >5 | 76 |
| 189 | 4.2 | 74 |
| 190 | 0.2 | 94 |
| 191 | 0.4 | 93 |
| 192 | >5 | 74 |
| 193 | 4.5 | 69 |
| 194 | >5 | 50 |
| 195 | 0.27 | 90 |
| 196 | 1.2 | 77 |
| 197 | >5 | 55 |
| 198 | >5 | 82 |
| 199 | >5 | 52 |
| 200 | 2.1 | 83 |
| 201 | 0.15 | 82 |
| 202 | 2.9 | 82 |
| 203 | 0.19 | 94 |
| 204 | 1.2 | 87 |
| 205 | >20 | 34 |
| 206 | 1.1 | 84 |
| 207 | 0.58 | 76 |
| 208 | 0.23 | 88 |
| 209 | 17.9 | 63 |
| 210 | 0.43 | 87 |
| 211 | 0.13 | 89 |
| 212 | 0.4 | 81 |
| 213 | 0.28 | 87 |
| 214 | 0.74 | 82 |
| 215 | 0.32 | 86 |
| 216 | 0.26 | 86 |
| 217 | 0.63 | 88 |
| 218 | 0.29 | 92 |
| 219 | >5 | 30 |
| 220 | >5 | 43 |
| 221 | 0.43 | 81 |
| 222 | >5 | 45 |
| 223 | >5 | 37 |
| 224 | >20 | — |
| 225 | >20 | — |
| 226 | >20 | — |
| 227 | >20 | — |
| 228 | 8.9 | — |
| 229 | 7.0 | — |
| 230 | 3.1 | — |
| 231 | 7.2 | — |
| 232 | 7.6 | — |
| 233 | >20 | — |
| 234 | 13 | — |

TABLE 1B

| Example | BK IC$_{50}$ (μM) | BB7 IC$_{50}$ (μM) |
|---|---|---|
| 235 | 5.2 | 5.4 |
| 236 | 10 | 9.6 |
| 237 | >27 | >24 |
| 238 | 19 | >30 |
| 239 | 4.6 | 5.4 |
| 240 | 8.9 | 18 |
| 241 | 27 | >30 |
| 242 | 27 | 18 |
| 243 | 6.3 | 10 |
| 244 | 0.3 | 1.8 |
| 245 | 0.4 | 0.74 |
| 246 | >30 | >30 |
| 247 | >24 | 18 |
| 248 | >30 | >30 |
| 249 | 7 | 12 |
| 250 | 3.7 | 3.9 |
| 251 | 1.7 | 3.5 |
| 252 | 7.3 | 19 |
| 253 | 0.35 | 0.7 |
| 254 | 3.3 | 5.8 |
| 255 | >30 | 15 |
| 256 | 0.15 | 0.34 |
| 257 | 1.9 | 2.9 |
| 258 | 9.4 | 14 |
| 259 | 0.5 | 1.6 |
| 260 | 0.4 | 1.2 |
| 261 | 0.4 | 0.9 |
| 262 | 2.7 | 8.3 |
| 263 | 1.3 | 3.2 |
| 264 | >30 | 27 |
| 265 | 20 | 22 |
| 266 | 14 | 17 |
| 267 | 0.66 | 2.3 |
| 268 | 4.6 | 6.1 |
| 269 | 9.4 | 9.4 |
| 270 | 20 | 17 |
| 271 | 2.7 | 3.5 |
| 272 | 0.5 | 1.5 |
| 273 | 1.4 | 6.5 |
| 274 | 9.3 | >26 |
| 275 | 1.2 | 3.5 |
| 276 | 1.3 | 1.7 |
| 277 | 2.6 | 6.2 |
| 278 | 15 | 23 |
| 279 | 2 | 2.4 |
| 280 | 0.8 | 2 |
| 281 | >30 | >30 |
| 282 | 13 | 22 |
| 283 | 15 | >27 |
| 284 | 1 | 2.3 |
| 285 | 0.4 | 1.1 |
| 286 | >30 | >30 |
| 287 | 5.1 | 6.5 |
| 288 | 22 | 18 |
| 289 | 0.12 | 0.23 |
| 290 | 3.2 | 4.9 |
| 291 | 0.23 | 0.5 |
| 292 | 0.13 | 0.26 |
| 293 | >30 | >30 |
| 294 | >30 | >30 |
| 295 | 3.6 | 3.1 |
| 296 | 7.2 | 6.3 |
| 297 | 1.8 | 2.8 |
| 298 | 0.3 | 0.5 |
| 299 | 0.5 | 0.9 |
| 300 | 0.14 | 0.25 |
| 301 | 5.4 | 11.3 |
| 302 | 4 | 18 |
| 303 | >30 | >30 |
| 304 | >30 | >30 |
| 305 | >30 | >30 |
| 306 | >30 | >30 |
| 307 | 5.8 | 9.6 |
| 308 | >30 | >30 |
| 309 | 26 | 27 |
| 310 | >25 | >25 |
| 311 | >30 | >30 |
| 312 | 16 | >30 |
| 313 | 1.8 | 1.5 |
| 314 | 1.4 | 3.1 |
| 315 | 0.4 | 2.1 |
| 316 | >30 | >30 |
| 317 | 0.6 | 0.9 |
| 318 | 0.14 | 0.25 |
| 319 | 0.06 | 0.08 |
| 320 | 2.9 | 6.0 |
| 321 | 0.3 | 0.6 |
| 322 | 0.04 | 0.16 |
| 323 | 4.9 | 11 |
| 324 | 0.2 | 0.35 |
| 325 | 0.08 | 0.19 |
| 326 | 6.5 | 9.4 |
| 327 | 0.8 | 1.7 |
| 328 | 4.3 | 3.9 |
| 329 | 0.6 | 1.5 |
| 330 | 1.6 | 8.4 |
| 331 | 0.5 | 2.5 |
| 332 | 6.4 | 14 |
| 333 | 1.3 | 7.6 |
| 334 | 3 | 5 |
| 335 | >30 | >30 |
| 336 | 4.7 | 8.7 |
| 337 | 19 | >30 |
| 338 | 3.3 | 3.9 |
| 339 | 0.49 | 2.8 |
| 340 | >30 | >28 |
| 341 | 1.7 | 3.6 |
| 342 | 1.7 | 10 |
| 343 | >30 | >30 |
| 344 | 0.7 | — |
| 345 | 3.4 | 6.2 |
| 346 | 6.1 | 8 |
| 347 | >29 | >30 |
| 348 | >30 | >30 |
| 349 | 4.4 | >24 |
| 350 | >30 | >30 |
| 351 | >30 | >30 |
| 352 | 0.9 | 2.8 |
| 353 | 2 | .81 |
| 354 | 3 | 2 |
| 355 | 5.1 | 2.9 |
| 356 | 1.8 | 1.4 |
| 357 | 1.3 | .97 |
| 358 | 16 | 20 |
| 359 | .07 | .07 |
| 360 | .09 | .04 |
| 361 | 1.8 | .77 |
| 362 | .11 | .07 |
| 363 | .36 | .13 |
| 364 | .48 | .22 |
| 365 | .1 | .06 |
| 366 | 1.7 | .55 |
| 367 | .08 | .09 |
| 368 | .11 | .13 |
| 369 | 0.004 | 0.01 |
| 370 | 0.04 | 0.03 |

The ability of the compounds of the present invention to inhibit Hepatitis C virus replicon constitutively expressed in a human liver cell line was established by the following experimental procedure:

Clone A cells (licensed from Apath, LLC) are derived from Huh-7 cells (human hepatoma cell line) and constitutively express the HCV replication proteins with concomitant amplification the HCV replicon (1b) genome. Cells are maintained and passaged in DMEM/ 10% FCS/1 mg/ml G418 (Geneticin from Gibco #11811-023; other media components as described below in "elisa media"). Care should be taken to maintain cell monolayers at a subconfluent state by 1:3 or 1:4 passages every 3–4 days. The replicon is extremely sensitive to the cellular metabolism/proliferation state and replicon copy number will rapidly decline in confluent monolayers (resting cells). Under ideal conditions each cell has, on average, 1000 copies of the HCV replicon genome.

Reagents:

Elisa media:

Dulbecco's Modified Eagle Media (DMEM) (Gibco #12430-047)

2% Fetal Calf Serum (FCS) (HyClone #SH30070.03)

1× pen/strep (Gibco #15140-122)

1× Non-essential amino acids (NEAA) (Gibco #11140-050)

no G418

Glutaraldehyde (Fisher #02957-4)

TWEEN-20, 10% (Roche #1332465)

TRITON X-100 (Sigma #T-8787)

Superblock in Phosphate Buffered Saline (PBS) (Pierce #37515)

NS5a monoclonal antibody (Virostat #1873)

Goat antimouse-HRP monoclonal antibody (BioRad #172-1011)

3,3',5,5' tetramethylbenzidine (TMB) substrate (Sigma #T-0440)

Compound Dilution/Cell Plating:

Drug Plate Preparation (Mother Plate)

10 µl of compounds (in DMSO) are added to column 3 of the mother plate. 5 µl of DMSO are added to the remaining columns. Mother plates are set aside until ready for serial dilution to be performed.

Control Drugs

Drug and Cell Addition:

The process for each plate involves:

Prepare cell plates (daughter plates) by adding 52 µl of Elisa media to each well.

In Mother plates, serially transfer 50 µl/well from column 3 through column 12.

Transfer 8 µl from mother plate to daughter plates (all 96 wells).

Place daughter plates in incubator until cells are prepared.

Harvest Clone A cells and plate directly into daughter plates at $0.7 \times 10^5$ cells/ml, 100 µl/well.

All plates are incubated at 37° C. in 5% $CO_2$ for 3 days.

Elisa Assay:

Remove media from 96-well plates (cells should be ca 80% confluent) by flicking into sink.

Add 130 µl/well 1×PBS+0.05% glutaraldehyde.

Incubate 37° C. for 1 hour.

Remove by flicking into sink.

Wash 3× with 300 µl/well PBS, shaking 5 min each wash. Remove by flicking into sink.

Add 130 µl/well PBS+0.05% TWEEN-20+0.1% TRITON X-100.

Incubate 37° C. for 10 minutes.

Remove by flicking into sink.

Add 300 µl/well Superblock in PBS.

Incubate 37° C. for 1 hour.

Remove by flicking into sink.

Wash 3× with 300 µl/well PBS, shaking 5 minutes each wash. Remove by flicking into sink.

During last wash, make a 1:100 dilution of NS5a Monoclonal-antibody (Mab) in Superblock+0.02% TWEEN-20.

After last wash, add 50 µl/well diluted Mab.

Incubate 37° C. for 1 hour.

Remove by flicking into sink.

Wash 3× with 300 µl/well PBS+0.02% TWEEN-20, shaking 5 minutes each wash.

Remove by flicking into sink.

During last wash, make a 1:500 dilution of goat anti-mouse-HRP Mab in Superblock+0.02% TWEEN-20.

After last wash, add 50 µl/well diluted Mab.

Incubate 37° C. for 1 hour.

Remove by flicking into sink.

Wash 5× with 300 µl/well PBS+0.02% TWEEN-20, shaking 5 minutes each wash. Remove by flicking into sink.

Wash 3× with 300 µl/well PBS, shaking 5 minutes each wash. Remove by flicking into sink.

After last wash, add 130 µl/well room temperature TMB substrate.

Incubate until blue color develops.

Add 130 µl/well 1N HCl to stop reaction (color turns from blue to yellow).

Read plates with optical density (O.D.) 450 filter.

ANALYSIS OF RESULTS: $IC_{50}$ (µM); $IC_{50}$ (µg/ml); % Inhibition

REFERENCE COMPOUNDS: Interferon-$a_2$; 4–30 U/ml IC50

The following non-limiting specific examples are included to illustrate the synthetic procedures used for preparing compounds of the formula (I). In these examples, all chemicals and intermediates are either commercially available or can be prepared by standard procedures found in the literature or are known to those skilled in the art of organic synthesis.

EXAMPLE 1

(5-Cyano-8-methyl-1-propyl-1,3,4,9-tetrahydro-pyrano[3,4-b]indol-1-yl)acetic acid 5-Bromo-2-methylaniline The mixture of Fe powder (9.31 g, 167 mmol) and $NH_4Cl$ (2.48 g, 46.3 mmol) in water (50 mL) was refluxed for 30 minutes. To this hot mixture was added 4-bromo-2-nitrotoluene (10 g, 46.3 mmol) slowly and then the reaction mixture was refluxed for 48 hours. The mixture was cooled to room temperature and extracted with EtOAc (3×100 mL). The organic solution was washed with $H_2O$ (3×200 mL) and brine (200 mL), dried ($Na_2SO_4$), and concentrated. The residue was purified by flash chromatography (silica, 15% EtOAc in hexanes) to give 7.9 g (92%) of title compound as a pale yellow oil. $^1H$ nuclear magnetic resonance (NMR) ($CDCl_3$): 300 MHz δ 6.88 (m, 1H), 6.81 (m, 2H), 3.63 (bs, 2H), 2.09 (s, 3H).

5-Bromo-2-methylphenylhydrazine Hydrochloride

To a suspension of 5-bromo-2-methylaniline (4.80 g, 25.8 mmol) in concentrated HCl (16 mL) was added dropwise a solution of sodium nitrite (1.96 g, 28.4 mmol) in water (10 mL) over 30 minutes at 0° C. To the mixture was added dropwise a solution of $SnCl_2.2H_2O$ (17.46 g, 77.4 mmol) in concentrated HCl (15 mL) over 50 minutes. After stirring for 1 hour at 0° C., the reaction mixture was basified with 50% NaOH (30 mL). The mixture was further diluted with water (20 mL) and treated with another 50% NaOH (10 mL) and then crushed ice (100 g). The reaction mixture was extracted with ether (3×100 mL) and the combined organic phases were washed with brine, dried over $Na_2SO_4$, and filtered. The filtrate was acidified by adding an anhydrous solution of HCl in ether (1 N in ether, 31 mL, 31 mmol). The precipitate was collected and dried under reduced pressure to give 4.57 g (75%) of title compound as a white amorphous solid. 1H NMR (DMSO): 300 MHz δ 10.31 (bs, 3H), 8.11 (bs, 1H), 7.12 (s, 1H), 7.06 (m, 2H), 2.14 (s, 3H).

4-Bromo-7-methyl Tryptophol

To a solution of 5-bromo-2-methylphenylhydrazine hydrochloride (4.57 g, 19.2 mmol) in 30% aqueous tetrahydrofuran (THF) (100 mL) at 0° C. was added dropwise a solution of 2,3-dihydrofuran (1.60 mL, 21.2 mmol) in THF (10 mL). After stirring for 2 hours at 0° C. and 12 hours at room temperature, the reaction mixture was diluted with ether (100 mL). The organic solution was washed with saturated $NaHCO_3$ (2×100 mL) and brine (100 mL), dried ($Na_2SO_4$) and concentrated. The residue was dissolved in ethylene glycol (30 mL), treated with $ZnCl_2$ (5.76 g, 42.2 mmol), and heated at 170° C. for 4 hours. The reaction mixture was cooled down to room temperature and 6 N HCl (100 mL) was added. The mixture was extracted with ether (3×100 mL) and washed with water (200 mL) and brine (200 mL). The organic solution was dried over $Na_2SO_4$ and concentrated. The residue was purified by flash chromatography (silica, 40% EtOAc in hexanes) to give 1.22 g (25%) of title compound as a light brown oil. 1H NMR ($CDCl_3$): 300 MHz δ 8.23 (bs, 1H), 7.18 (d, J=7.65 Hz, 1H), 7.08 (d, J=2.16 Hz, 1H), 6.81 (d, J=7.65 Hz, 1H), 3.95 (t, J=6.42 Hz, 2H), 3.27 (t, J=6.42 Hz, 2H), 2.40 (s, 3H), 1.69 (bs, 1H)

5-Bromo-8-methyl-1-propyl-1,3,4,9-tetrahydropyrano[3,4-b]indole-1-acetic Acid Ethyl Ester To a solution of 4-bromo-7-methyl tryptophol (1.12 g, 4.41 mmol) and ethyl butyrylacetate (0.71 mL, 4.41 mmol) in $CH_2Cl_2$ (20 mL) was added $BF_3.OEt_2$ (0.56 mL, 4.41 mmol) dropwise at room temperature. The solution was stirred for 2 hours and then washed with saturated aqueous $NaHCO_3$ (15 mL) and brine (15 mL). The organic phase was dried ($Na_2SO_4$) and filtered through a pad of silica gel. The filter cake was washed with additional $CH_2Cl_2$ and the combined organic layer was evaporated to provide 1.62 g (93%) of title compound as a white solid. 1H NMR ($CDCl_3$): 300 MHz δ 9.33 (bs, 1H), 7.11 (d, J=7.65 Hz, 1H), 6.76 (d, J=7.65 Hz, 1H), 4.19 (m, 2H), 4.03 (m, 1H), 3.90 (m, 1H), 3.15 (m, 2H), 3.03 (d, J=16.6 Hz, 1H), 2.89 (d, J=16.6 Hz, 1H), 2.43 (s, 3H), 2.08 (m, 1H), 1.96 (m, 1H), 1.38 (m, 1H), 1.27 (t, J=7.14 Hz, 3H), 1.18 (m, 1H), 0.87 (t, J=7.29 Hz, 3H).

5-Cyano-8-methyl-1-propyl-1,3,4,9-tetrahydropyrano[3,4-b]indole-1-acetic acid Ethyl Ester 5-Bromo-8-methyl-1-propyl-1,3,4,9-tetrahydropyrano[3,4-b]indole-1-acetic acid ethyl ester (1.27 g, 3.22 mmol) and CuCN (0.433 g, 4.83 mmol) was dissolved in N-methyl-2-pyrrolidinone (15 mL) and the solution was divided into the 4 microwave reaction vessels (3.75 mL each). The reaction vessels were heated in microwave at 220° C. for 15 minutes. The reaction mixtures in 4 vessels were combined and then diluted with water (30 mL). The crude mixture was extracted with EtOAc (3×50 mL). The combined organic phase was washed with brine (100 mL), dried over $Na_2SO_4$ and concentrated. The residue was purified by flash chromatography (silica, 20% EtOAc in hexanes) to give 0.959 g (88%) of title compound as a white solid. 1H NMR ($CDCl_3$): 300 MHz δ 9.75 (bs, 1H), 7.33 (d, J=7.52 Hz, 1H), 6.93 (d, J=7.52 Hz, 1H), 4.21 (m, 2H), 4.11 (m, 1H), 4.03 (m, 1H), 3.08 (t, J=5.52, 2H), 2.99 (d, J=4.17 Hz, 2H), 2.57 (s, 3H), 2.06 (m, 2H), 1.42 (m, 1H), 1.26 (t, J=7.16 Hz, 3H), 1.18 (m, 1H), 0.88 (t, J=7.32 Hz, 3H).

5-Cyano-8-methyl-1-propyl-1,3,4,9-tetrahydropyrano[3,4-b]indole-1-acetic acid

To a solution of 5-cyano-8-methyl-1-propyl-1,3,4,9-tetrahydropyrano[3,4-b]indole-1-acetic acid ethyl ester (0.959 g, 2.82 mmol) in THF/MeOH (7 mL/15 mL) was added 1 N NaOH (5.64 mL, 5.64 mmol). The reaction mixture was stirred at ambient temperature overnight. The most of THF/MeOH was removed under reduced pressure and the resulting mixture was acidified with 1 N HCl. The mixture was extracted with EtOAc (3×30 mL). The combined organic phase was washed with brine (60 mL), dried over $Na_2SO_4$ and concentrated to provide 0.868 g (99%) of title compound as a white solid. 1H NMR (acetone-d6): 300 MHz δ 10.37 (bs, 1H), 7.35 (d, J=7.50 Hz, 1H), 7.03 (d, J=7.50 Hz, 1H), 4.05 (m, 2H), 3.08–2.91 (m, 4H), 2.54 (s, 3H), 2.09 (m, 2H), 1.45 (m, 1H), 1.03 (m, 1H), 0.84 (t, J=7.26 Hz, 3H).

EXAMPLE 2 AND EXAMPLE 3

[(R)-5-cyano-8-methyl-1-propyl-1,3,4,9-tetrahydropyrano[3,4-b]indol-1-yl]acetic acid

[(S)-5-cyano-8-methyl-1-propyl-1,3,4,9-tetrahydropyrano[3,4-b]indol-1-yl]acetic acid Resolution of (±)-5-Cyano-8-methyl-1-propyl-1,3,4,9-tetrahydropyrano[3,4-b]indole-1-acetic acid Preparative high pressure liquid chromatography (HPLC) using CHIRALPACK-AD (250×20 mm) and 10% isopropyl alcohol in heptane (0.1% trifluoroacetic acid (TFA)) as eluant gave (R) and (S) enantiomers of 5-cyano-8-methyl-1-propyl-1,3,4,9-tetrahydropyrano[3,4-b]indole-1-acetic acid as white solids. HRMS (ESI) [M+H]$^+$ calculated for $C_{18}H_{21}N_2O_3$ 313.1547, found 313.1545 (R enantiomer) and 313.1547 (S enantiomer); Chiral HPLC HP 1100 with spiderlink CHIRALPACK-AD, 250×4.6 mm, isopropyl alcohol/heptane containing 0.1% TFA (10:90), 1.0 mL/minutes, DAD 215 nm; $t_R$=6.98 minutes (R enantiomer), 9.37 minutes (S enantiomer).

Alternatively, [(R)-5-cyano-8-methyl-1-propyl-1,3,4,9-tetrahydropyrano[3,4-b]indol-1-yl]acetic acid can be obtained by resolution with cinchonine according to the following procedure. (±)-5-Cyano-8-methyl-1-propyl-1,3,4,9-tetrahydropyrano[3,4-b]indole-1-acetic acid (6.4 g, 20.5 mmol) and cinchonine (5.9 g, 20.0 mmol) were dissolved in a mixture of 2-butanone (125 mL) and water (5 mL) with heating. The clear solution was stirred and allowed to cool to room temperature overnight. The resulting solid was isolated, washed with 10 mL of 2-butanone, and dried to give 2.4 g (20% yield, >98% e.e.). The mother liquor was concentrated and dissolved again in a mixture of 2-butanone (100 mL) and water (1.5 mL) with heating. The solution was stirred and allowed to cool to room temperature overnight. The resulting solid was isolated, washed with 10 mL of 2-butanone, and dried to give a second crop of salt: 2.3 g (18% yield, >98% e.e.). The two crops (total 4.7 g) were combined and treated with 50 mL of 1N HCl and 100 mL of ethyl acetate. The ethyl acetate layer was washed with 1N HCl (30 mL) and water (50 mL). The aqueous layers were combined and extracted with ethyl acetate (50 mL). This ethyl acetate layer was washed with water (50 mL). The combined ethyl acetate layers were dried over sodium sulfate, filtered, and concentrated in vacuo to give 2.25 g.

This material was triturated with 10 mL of ethyl acetate and the precipitate was collected, rinsed with 5 mL of ethyl acetate, and dried to give 1.27 g (e.e. >98%). The mother liquor was concentrated to a volume of 5 mL and the new formed precipitate was collected, rinsed with 2 mL of ethyl acetate and dried. A second crop of 0.4 g was obtained with an e.e. of >99%. The mother liquor was concentrated and gave a third crop of 0.5 g with an e.e. of >99%.

The absolute configuration of the compound of Example 2 was determined by single crystal X-ray crystallography of the 4-bromobenzyl amide derivative, which was prepared as described below.

1-(R)-N-(4-Bromo-benzyl)-2-(5-cyano-8-methyl-1-propyl-1,3,4,9-tetrahydropyrano[3,4-b]indol-1-yl)-acetamide To a solution of 1-(R)-5-cyano-8-methyl-1-propyl-1,3,4,9-tetrahydropyrano[3,4-b]indole-1-acetic acid (20.0 mg, 0.064 mmol), 1-[3-(dimethylamino)propyl]-3-ethylcarbodiimide hydrochloride (EDCI, 15.0 mg, 0.077 mmol) and 1-hydroxybenzotriazole (10.4 mg, 0.077 mmol) in DMF (4 mL) was added N,N-diisopropylethylamine (67 µl, 0.384 mmol) followed by 4-bromobenzylamine hydrochloride (17.1 mg, 0.077 mmol) at room temperature. The reaction mixture was stirred for 20 hours at ambient temperature. Water (5 mL) was added to the mixture and the resulting mixture was extracted with EtOAc (3×10 mL). The combined organic phase was washed with brine (20 mL), dried over $Na_2SO_4$ and concentrated. The residue was purified by flash chromatography (silica, 40% EtOAc in hexanes) to give 27 mg (88%) of title compound as a white solid. The solid was crystallized from EtOAc for X-ray crystallography. Mp=173–175° C.; 1H NMR ($CDCl_3$): 300 MHz δ 10.15 (bs, 1H), 7.33 (m, 3H), 6.97 (m, 2H), 6.88 (m, 1H), 4.42 (dd, J=11.2, 4.6 Hz, 1H), 4.29 (dd, J=11.2, 4.6 Hz, 1H), 4.03 (m, 2H), 3.11–2.95 (m, 4H), 2.24 (s, 3H), 2.07 (m, 1H), 1.91 (m, 1H), 1.35 (m, 2H), 0.89 (t, J=5.4 Hz, 3H); HRMS (ESI) $[M+H]^+$ calculated for $C_{25}H_{27}BrN_3O_2$ 480.1281, found 480.1285.

The absolute configuration of the compound of Example 3 was determined by single crystal X-ray crystallography of the 4-bromobenzyl amide derivative.

1-(S)-N-(4-Bromo-benzyl)-2-(5-cyano-8-methyl-1-propyl-1,3,4,9-tetrahydropyrano[3,4-b]indol-1-yl)-acetamide The above procedure was followed starting from 1-(S)-5-cyano-8-methyl-1-propyl-1,3,4,9-tetrahydropyrano[3,4-b]indole-1-acetic acid. Mp=173–175° C.; 1H NMR ($CDCl_3$): 300 MHz δ 9.99 (bs, 1H), 7.36 (m, 3H), 6.95 (m, 3H), 6.71 (bs, 1H), 4.42 (dd, J=11.4, 4.6 Hz, 1H), 4.28 (dd, J=11.4, 4.6 Hz, 1H), 4.03 (m, 2H), 3.10–2.92 (m, 4H), 2.34 (s, 3H), 2.05 (m, 1H), 1.91 (m, 1H), 1.34 (m, 2H), 0.89 (t, J=5.4 Hz, 3H); HRMS (ESI) $[M+H]^+$ calculated for $C_{25}H_{27}BrN_3O_2$ 480.1281, found 480.1274.

EXAMPLE 4

(5-Cyano-8-fluoro-1-propyl-1,3,4,9-tetrahydropyrano[3,4-b]indol-1-yl)acetic acid 5-Bromo-2-fluoroaniline Iron powder (9.3 g, 0.166 mM) and ammonium chloride (1.7 g, 0.032 mM) were stirred in water (42 ml) at 100° C. for 30 minutes. Commercially available 2-nitro 4-bromo fluorobenzene (9.2 g, 0.42 mM) was added drop wise to the above solution over a period of 45 minutes. The reaction was stirred at 100° C. for an additional five hours. Water was removed in vacuo. The resultant crude solution was stirred in ethyl acetate (100 mL) for 20 minutes and the organic solution was decanted off. This wash was repeated two more times. The organic layers were combined, dried ($MgSO_4$), passed through a plug of $SiO_2$, and concentrated to afford 4.2 g (53% yield) of the desired product as a red oil. The product was used without further purification. NMR ($CHCl_3$) δ 3.78 (bs, 2H); 6.65–7.07(m, 3H).

See, Courtin, A. Helv. Chim. Acta. 66, 1, (1983), hereby incorporated by reference.

5-Bromo-2-fluorophenylhydrazine

A solution of sodium nitrate (0.49 g, 0.007 mM) in water (1.5 ml) was added drop wise to a vigorously stirred heterogeneous solution of 5-bromo-2-fluoroaniline (1.4 g) in concentrated HCl(aq) (3.5 ml) over a 30 minutes period at 0° C. Tin (II) chloride dihydrate (4.5 g, 0.02 mM) in concentrated HCl(aq) (3.5 ml) was added drop wise to the above solution over a period of 30 minutes. After the addition, the solution was allowed to stir at 0° C. for one hour. The reaction solution was basified (pH>7) by slowly adding a solution of 50% aqueous NaOH to the reaction mixture. The water layer was washed with diethyl ether (3×). The organic layers were combined, dried ($MgSO_4$), and concentrated. The resultant solid was thoroughly washed with hexanes. The undissolved solid was captured on filter and further washed with hexanes to afford 0.81 g (54% yield) of the desired product as an off-white solid. NMR ($CHCl_3$) δ 5.45 (bs, 1H); 6.80–6.86(m, 2H); 7.25–7.28 (m, 1H).

See, McKittrick, B. et al., J. Heterocyclic Chem. 27, 2151 (1990), hereby incorporated by reference.

4-Bromo-7-fluoro Tryptophol 2,3-Dihydrofuran (2.0 ml, 0.026 mM) was added to a solution of 5-bromo-2-fluorophenyl hydrazine (4.43 g, 0.21 mM) in dry THF (40 ml) at 0° C. Concentrated HCl(aq) (2.0 ml) was added to the mixture and the reaction was allowed to warm to room temperature and stirred overnight. THF was removed in vacuo. The crude residue was taken up in water and washed with ethyl acetate (3×). The organic layers were combined, dried ($MgSO_4$), and concentrated to afford 4.2 g of a mixture of the mono and di-adducts as a red oil. This crude mixture was used without further purification in the next step.

Zinc chloride (5.4 g, 0.39 mM) and the crude mixture were stirred in ethylene glycol at 160° C. for three hours. The reaction was cooled and diluted with 10% HCl (aq) (50 ml). The aqueous layer was washed with ethyl acetate (3×). The organic layers were combined, dried ($MgSO_4$), and concentrated. The product was purified by using silica gel flash chromatography (mobile phase: 3:2/hexanes:ethyl acetate) to afford 1.2 g (yield: 21%) of the desired product as an off-white solid. NMR($CHCl_3$) δ 3.26 (t, 2H, 6.3 Hz); 3.96(t, 2H, 6.4 Hz); 6.75 (m, 1H); 7.15(m, 2H); 8.54(bs, 1H).

5-Bromo-8-fluoro-1-propyl-1,3,4,9-tetrahydropyrano[3,4-b]indole-1-acetic acid Ethyl Ester $BF_3$-etherate (0.74 ml, 0.0059 mM) was added to a solution of 4-bromo-7-fluorotryptophol (1.0 g, 0.0039 mM) and ethyl butyrylacetate (0.93 ml, 0.0059 mM) in dry dichloromethane (15 ml). This reaction was stirred for three hours at room temperature. Sat. NaHCO$_3$ (aq) (15 ml) was added to quench the reaction. The solution was washed with DCM (2×). The organic layers were combined, dried (MgSO$_4$), passed through a plug of SiO$_2$, and concentrated to afford 1.02 g (66% yield) of the desired product as an off-white solid. NMR (CHCl$_3$) δ 0.87 (t, 3H, 7.38 Hz); 1.44(m, 1H); 1.28(t, 3H, 7.14 Hz); 1.39(m, 1H); 1.93(m, 1H); 2.03(m, 1H); 2.91m(m, 1H); 3.06(m 1H); 3.15(m, 2H); 3.91(m, 1H); 4.03(m, 1H); 4.22(m, 2H); 6.72(m, 1H); 7.09 (m, 1H); 9.50(s, 1H).

5-Cyano-8-fluoro-1-propyl-1,3,4,9-tetrahydropyrano [3,4-b]indole-1-acetic acid Ethyl Ester The above ester (1.02 g, 0.026 mM) was dissolved in N-Methyl pyrrolidinone (12 ml). This solution was distributed equally into four Personal Chemistry microwave reaction vessels. CuCN (0.085 g, 0.0096 mM) was added into each reaction vessel. The reaction vessels were heated, under microwave conditions, at 220° C. for 15 minutes. The reaction solutions were combined and diluted with water (30 ml). The aqueous layer was washed with ethyl acetate (3×). The organic layers were combined, dried (MgSO$_4$), and concentrated. The product was purified by SiO$_2$ flash chromatography to afford 0.81 g (92% yield) of the desired product as an off-white solid. NMR (d$_6$-DMSO) δ 0.78 (t, 3H); 0.86(m, 2H); 1.0(t, 3H); 1.29(m, 2H); 1.92(m, 2H); 2.76(d, 1H); 2.86(t, 2H); 3.02(d, 1H); 3.9(m, 4H); 7.07(m, 1H); 7.5(m, 1H); 11.94(s, 1H).

5-Cyano-8-fluoro-1-propyl-1,3,4,9-tetrahydropyrano [3,4-b]indole-1-acetic acid

1N NaOH(aq) (4.6 ml) was added to a solution of the above ester (0.8 g, 0.0023 mM) in 1:1/MeOH:THF (10 ml) and stirred at room temperature overnight. THF and MeOH were removed in vacuo. The residue was diluted with brine (10 ml), acidified with (pH<2) concentrated HCl (aq), and washed with ethyl acetate (3×). The organic layers were combined, dried (MgSO$_4$), and concentrated to afford 0.61 g (82% yield) of the desired product as a white solid. NMR (d$_6$-DMSO) δ 0.95 (t, 3H, 5.4 Hz); 1.23(m, 1H); 1.42(m, 1H); 2.05(m, 1H); 2.99–3.13 (m, 4H); 3.99(m, 1H); 4.11(m, 2H); 6.90(m, 1H); 7.39(m, 1H); 9.45(s, 1H).

EXAMPLE 5 AND EXAMPLE 6

[(R)-5-cyano-8-fluoro-1-propyl-1,3,4,9-tetrahydropyrano[3,4-b]indol-1-yl]acetic acid

[(S)-5-cyano-8-fluoro-1-propyl-1,3,4,9-tetrahydropyrano[3,4-b]indol-1-yl]acetic acid Resolution of (±)-5-Cyano-8-fluoro-1-propyl-1,3,4, 9-tetrahydropyrano[3,4-b]indole-1-acetic acid Preparative HPLC using CHIRALPACK-AD (250×20 mm) and 10% isopropyl alcohol in heptane (0.1% TFA) as eluant gave (R) and (S) enantiomers of 5-cyano-8-fluoro-1-propyl-1,3,4,9-tetrahydropyrano[3,4-b]indole-1-acetic acid as white solids. Chiral HPLC HP 1100 with spiderlink CHIRALPACK-AD, 250×4.6 mm, isopropyl alcohol/heptane containing 0.1% TFA (10:90), 1.0 mL/minutes, DAD 215 nm; tR=6.1 minutes (R enantiomer), 8.3 minutes (S enantiomer).

Alternatively, [(S)-5-cyano-8-fluoro-1-propyl-1,3,4,9-tetrahydropyrano[3,4-b]indol-1-acetic acid can be obtained by resolution with (+) (1S,2R) ephedrine according to the following procedure. (±)-5-Cyano-8-fluoro-1-propyl-1,3,4, 9-tetrahydropyrano[3,4-b]indole-1-acetic acid (27.75 g, 87.8 mmol) and (+) (1S,2R) ephedrine hemihydrate (15.28 g, 87.8 mmol) were dissolved in a mixture of isopropyl alcohol (730 mL) and water (43 mL) with heating. The clear solution was seeded with 98% e.e. ephedrine salt and allowed to cool to room temperature overnight. The resulting solid was isolated and washed with isopropyl alcohol (20 mL) to give 18.82 g of salt (44% yield, >98% e.e.). Liberation of the salt was accomplished by addition of 1N HCl and ethylacetate to afford 12.4 g of acid. This material was combined with 0.9 g of acid obtained from previous experiments and recrystallized from ethyl acetate (30 mL) to afford 7.4 g in the first crop (>99.8% e.e.) and another 3.8 g in the second crop (99.3–99.6% e.e.). These two crops were combined to give 11.1 g of resolved (S) acid (40% yield, >99.5% e.e.). Concentration of the mother liquor afforded 2.4 g of (S) acid (98% e.e.).

The absolute configuration of the compound of Example 5 was determined by single crystal X-ray crystallography of the 4-bromobenzyl amide derivative.

1-(R)-N-(4-Bromo-benzyl)-2-(5-cyano-8-fluoro-1-propyl-1,3,4,9-tetrahydropyrano[3,4-b]indol-1-yl)-acetamide The procedure described for Example 3 was followed starting from 1-(R)-5-cyano-8-fluoro-1-propyl-1,3,4,9-tetrahydropyrano[3,4-b]indole-1-acetic acid. 1H NMR (d$_6$-DMSO) δ 0.79 (t, 3H, 5.4 Hz); 0.94(m, 1H); 1.31(m, 1H); 1.96(m, 2H); 2.75 (d, 1H, 10.2 Hz); 2.91(m, 3H); 4.03(m, 2H); 4.21(d, 2H, 4.5 Hz); 7.09(m, 3H); 7.37(d, 2H, 6.0 Hz); 7.52(m, 1H); 8.22(t, 1H, 6.0 Hz); 11.93(s, 1H); MS: M–H: 482.1; CHN for C$_{24}$H$_{23}$BrFN$_3$O$_2$— Theory: C, 59.51; H, 4.79; N, 8.68. Found: C, 59.53; H, 4.86; N, 8.66.

EXAMPLE 7

5,8-Dichloro-1-propyl-1,3,4,9-tetrahydro-pyrano[3, 4-b]indol-1-yl)acetic acid 4,7-Dichloro-Tryptophol To a solution of 2,5 dichlorophenylhydrazine hydrochloride (20.4 g 0.11 mol) in THF (80 mL) at 0° C. was added dropwise a solution of 2,3-dihydrofuran (10.5 mL, 0.14 mol), water (15 mL) and HCl concentrated (5 mL). After stirring for 4 hours, the reaction mixture was diluted with ether (100 mL). The organic solution was washed with saturated NaCl (2×50 mL) and dried (Na$_2$SO$_4$) and concentrated. The residue was dissolved in ethylene glycol (60 mL), treated with ZnCl$_2$ (34.6 g, 0.25 mol), and heated at 140° C. for 8 hours. The reaction mixture was cooled down to room temperature and 10% HCl was added. The mixture was extracted with ethyl actetate (3×75 mL) and washed with brine. The organic solution was dried over Na$_2$SO$_4$ and concentrated. The residue was purified by flash chromatography (silica gel 60, EtOAc:Hexane 3:1) to give 10.4 g (39%) of title compound as a light brown oil. 1H NMR (CDCl$_3$): 300 MHz δ 8.35 (bs, 1H), 7.16 (d, J=2.1 Hz, 1H), 7.09 (d, J=8.4 Hz, 1H), 7.01 (d, J=8.1 Hz, 1H), 3.95 (t, J=6.3 Hz, 2H), 3.25 (t, J=6.3 Hz, 2H), 1.49 (bs, 1H).

5,8-Dichloro-1-propyl-1,3,4,9-tetrahydropyrano[3,4-b]indole-1-acetic Acid Ethyl Ester To a solution of 5,8 dichloro tryptophol (4.25 g, 18.55 mmol) and ethyl butyrylacetate (4.37 mL, 27.63 mmol) in $CH_2Cl_2$ (40 mL) was added $BF_3xOEt_2$ (3.50 mL, 27.63 mmol) dropwise at room temperature. The solution was stirred for 2 hours and then washed with saturated aqueous $NaHCO_3$ (30 mL) and brine and concentrated. The oil was then purified by flash chromatography (silica gel 60, EtOAc: Hexane 4:1) to yield 1.5 g (32%). 1H NMR ($CDCl_3$): 300 MHz δ 9.55 (bs, 1H), 7.03 (d, J=8.10 Hz, 1H), 6.95 (d, J=8.10 Hz, 1H), 4.3 (m, 2H), 4.02 (m, 1H), 3.89 (m, 1H), 3.01 (m, 2H), 2.99 (m, 1H), 2.92(m, 1H), 2.01 (m, 2H), 1.28 (m, 5H), 0.88 (t, J=7.30 Hz, 3H).

5,8-Dichloro-1-propyl-1,3,4,9-tetrahydropyrano[3,4-b]indole-1-acetic acid

To a solution of 5,8 dichloro-1-propyl-1,3,4,9-tetrahydropyrano[3,4-b]indole-1-acetic acid ethyl ester (1.2 g, 3.24 mmol) in EtOH (35 mL) was added 1 N NaOH (7 mL). The reaction mixture was stirred at 50° C. for 6 hours. The most of EtOH/NaOH was removed under reduced pressure and the resulting mixture was purified on HPLC to yield a white solid 0.730 g (66%). 1H NMR ($CDCl_3$): 300 MHz δ 9.12 (bs, 1H), 7.03 (d, J=8.26 Hz, 1H), 6.96 (d, J=8.26 Hz, 1H), 4.04 (m, 2H), 3.14(m, 2H), 3.06(m, 2H), 2.03 (m, 2H), 1.42 (m, 1H), 1.21(m, 1H), 0.89 (t, J=7.34 Hz, 3H).

EXAMPLE 8 AND EXAMPLE 9

[(R)-5,8-dichloro-1-propyl-1,3,4,9-tetrahydropyrano[3,4-b]indol-1-yl]acetic acid

[(S)-5,8-dichloro-1-propyl-1,3,4,9-tetrahydropyrano[3,4-b]indol-1-yl]acetic acid

Resolution of (±)-5,8-dichloro-1-propyl-1,3,4,9-tetrahydropyrano[3,4-b]indole-1-acetic Acid Preparative HPLC using CHIRALCEL OJ (250×20 mm) and 3% isopropyl alcohol in heptane (0.1% TFA) as eluant gave (S) and (R) enantiomer of 5,8-dichloro-1-propyl-1,3,4,9-tetrahydropyrano[3,4-b]indole-1-acetic acid as a white solid. Chiral HPLC-HP 1100 with spiderlink; CHIRALCEL OJ, 250×4.6 mm, isopropyl alcohol/heptane (containing 0.1% TFA)=3:97, 1.0 mL/minutes, DAD 215 nm; $t_R$=10.2 minutes (S enantiomer), 15.7 minutes (R enantiomer).

EXAMPLE 10

(5-cyano-6-fluoro-8-methyl-1-propyl-1,3,4,9-tetrahydropyrano[3,4-b]indol-1yl)acetic acid

4-Bromo-3-fluoro-6-nitrotoluene

To a stirred solution of 4-bromo-3-fluorotoluene (10 g, 52.9 mmol) in $H_2SO_4$ (100 mL) was added $KNO_3$ (5.34 g, 52.9 mmol) at 0° C. After stirring overnight at room temperature, the reaction mixture was poured into ice (200 g) and extracted with EtOAc (3×300 mL). The organic solution was washed with brine (200 mL), dried ($Na_2SO_4$), and concentrated to give 12.35 g (100%) of title compound as a pale yellow oil. 1H NMR ($CDCl_3$): 300 MHz δ 8.29 (d, J=6.30 Hz, 1H), 7.12 (d, J=8.61 Hz, 1H), 2.60 (s, 3H).

5-Bromo-4-fluoro-2-methylaniline

The mixture of iron powder (17.8 g, 318 mmol) and $NH_4Cl$ (5.10 g, 95.4 mmol) in water (100 mL) was refluxed for 30 minutes. To this hot mixture was added 4-bromo-3-fluoro-6-nitrotoluene (18.6 g, 79.5 mmol) slowly and then the reaction mixture was refluxed for 48 hours. The mixture was cooled to room temperature and extracted with EtOAc (3×200 mL). The organic solution was washed with $H_2O$ (3×300 mL) and brine (300 mL), dried ($Na_2SO_4$), and concentrated. The residue was purified by flash chromatography (silica, 20% EtOAc in hexanes) to give 11.7 g (72%) of title compound as a pale yellow solid. 1H NMR ($CDCl_3$): 300 MHz δ 6.82 (m, 2H), 3.49 (bs, 2H), 2.11 (s, 3H).

5-Bromo-4-fluoro-2-methylphenylhydrazine Hydrochloride

To a suspension of 5-bromo-4-fluoro-2-methylaniline (11.2 g, 54.9 mmol) in concentrated HCl (35 mL) was added dropwise a solution of sodium nitrite (4.17 g, 60.4 mmol) in water (20 mL) over 30 minutes at 0° C. To the mixture was added dropwise a solution of $SnCl_2.2H_2O$ (37.2 g, 165 mmol) in concentrated HCl (45 mL) over 1 hour. After stirring for 2 hours at 0° C., the reaction mixture was basified with 50% NaOH (50 mL). The mixture was further diluted with water (50 mL) and treated with another 50% NaOH (20 mL) and then crushed ice (200 g). The reaction mixture was extracted with ether (3×200 mL) and the combined organic phases were washed with brine, dried over $Na_2SO_4$, and filtered. The filtrate was acidified by adding an anhydrous solution of HCl in ether (2 N in ether, 42 mL, 82.5 mmol). The precipitate was collected and dried under reduced pressure to give 9.92 g (71%) of title compound as a pale yellow solid. 1H NMR (DMSO): 300 MHz δ 10.18 (bs, 3H), 7.98 (bs, 1H), 7.21 (m, 2H), 2.16 (s, 3H).

4-Bromo-5-fluoro-7-methyl Tryptophol

To a solution of 5-bromo-4-fluoro-2-methylphenylhydrazine hydrochloride (4.75 g, 18.6 mmol) in 20% aqueous THF (100 mL) at 0° C. was added dropwise a solution of 2,3-dihydrofuran (1.55 mL, 20.4 mmol) in THF (10 mL). After stirring for 2 hours at 0° C. and 12 hours at room temperature, the reaction mixture was diluted with ether (100 mL). The organic solution was washed with saturated $NaHCO_3$ (2×100 mL) and brine (100 mL), dried ($Na_2SO_4$) and concentrated. The residue was dissolved in ethylene glycol (50 mL), treated with $ZnCl_2$ (5.58 g, 40.9 mmol), and heated at 170° C. for 4 hours. The reaction mixture was cooled down to room temperature and 6 N HCl (100 mL) was added. The mixture was extracted with ether (3×100 mL) and washed with water (200 mL) and brine (200 mL). The organic solution was dried over $Na_2SO_4$ and concentrated. The residue was purified by flash chromatography (silica, 40% EtOAc in hexanes) to give 1.52 g (30%) of title compound containing inseparable impurities (<20%) as a light brown oil. 1H NMR ($CDCl_3$): 300 MHz δ 8.68 (bs, 1H), 7.06 (d, J=2.4 Hz, 1H), 6.76 (d, J=9.63 Hz, 1H), 3.92 (t, J=6.48 Hz, 2H), 3.21 (t, J=6.48 Hz, 2H), 2.35 (s, 3H), 2.27 (bs, 1H).

5-Bromo-6-fluoro-8-methyl-1-propyl-1,3,4,9-tetrahydropyrano[3,4-b]indole-1-acetic Acid Ethyl Ester To a solution of 4-bromo-7-methyl tryptophol (400 mg g, 1.47 mmol) and ethyl butyrylacetate (0.28 mL, 1.76 mmol)

in CH$_2$Cl$_2$ (5 mL) was added BF$_3$.OEt$_2$ (0.22 mL, 1.76 mmol) dropwise at room temperature. The solution was stirred for 2 hours and then washed with saturated aqueous NaHCO$_3$ (5 mL) and brine (5 mL). The organic phase was dried (Na$_2$SO$_4$) and concentrated. The residue was purified by flash chromatography (silica, 15% EtOAc in hexanes) to give 496 mg (82%) of title compound as a pale yellow solid. Mp=137–138° C.; 1H NMR (CDCl$_3$): 300 MHz δ 9.73 (bs, 1H), 6.76 (d, J=10.1 Hz, 1H), 4.21 (m, 2H), 4.05 (m, 1H), 3.91 (m, 1H), 3.05–2.89 (m, 4H), 2.53 (s, 3H), 2.07 (m, 1H), 1.92 (m, 1H), 1.38 (m, 1H), 1.30 (t, J=6.98 Hz, 3H), 1.21 (m, 1H), 0.89 (t, J=7.08 Hz, 3H).

5-Cyano-6-fluoro-8-methyl-1-propyl-1,3,4,9-tetrahydropyrano[3,4-b]indole-1-acetic Acid Ethyl Ester 5-Bromo-6-fluoro-8-methyl-1-propyl-1,3,4,9-tetrahydropyrano[3,4-b]indole-1-acetic acid ethyl ester (496 mg, 1.20 mmol) and CuCN (162 mg, 1.81 mmol) was dissolved in N-methyl-2-pyrrolidinone (6 mL) and the solution was divided into the 2 microwave reaction vessels (3.0 mL each). The reaction vessels were heated in microwave at 220° C. for 15 minutes. The reaction mixtures in 2 vessels were combined and then diluted with water (10 mL). The crude mixture was extracted with EtOAc (3×20 mL). The combined organic phase was washed with brine (50 mL), dried over Na$_2$SO$_4$ and concentrated. The residue was purified by flash chromatography (silica, 25% EtOAc in hexanes) to give 404 mg (94%) of title compound as a white solid. 1H NMR (DMSO): 300 MHz δ 12.02 (bs, 1H), 11.33 (bs, 1H), 7.00 (d, J=9.00 Hz, 1H), 3.96 (m, 2H), 2.95 (d, J=10.3 Hz, 1H), 2.83 (t, J=3.9 Hz, 1H), 2.72 (d, J=10.3 Hz, 1H), 2.54 (s, 3H), 1.99 (m, 2H), 1.28 (m, 1H), 0.85 (m, 1H), 0.79 (t, J=5.41 Hz, 3H).

5-Cyano-6-fluoro-8-methyl-1-propyl-1,3,4,9-tetrahydropyrano[3,4-b]indole-1-acetic Acid To a solution of 5-cyano-6-fluoro-8-methyl-1-propyl-1,3,4,9-tetrahydropyrano[3,4-b]indole-1-acetic acid ethyl ester (404 mg, 1.13 mmol) in THF/MeOH (2.5 mL/5 mL) was added 1 N NaOH (2.26 mL, 2.26 mmol). The reaction mixture was stirred at ambient temperature overnight. Most of the THF/MeOH was removed under reduced pressure and the resulting mixture was acidified with 1 N HCl. The mixture was extracted with EtOAc (3×10 mL). The combined organic phase was washed with brine (20 mL), dried over Na$_2$SO$_4$ and concentrated to provide 341 mg (91%) of title compound as a white solid. 1H NMR (DMSO): 300 MHz δ 12.02 (bs, 1H), 11.33 (bs, 1H), 7.00 (d, J=9.00 Hz, 1H), 3.96 (m, 2H), 2.95 (d, J=10.3 Hz, 1H), 2.83 (t, J=3.9 Hz, 1H), 2.72 (d, J=10.3 Hz, 1H), 2.54 (s, 3H), 1.99 (m, 2H), 1.28 (m, 1H), 0.85 (m, 1H), 0.79 (t, J=5.41 Hz, 3H).

EXAMPLE 11 AND EXAMPLE 12

[(R)-5-cyano-6-fluoro-8-methyl-1-propyl-1,3,4,9-tetrahydropyrano[3,4b]indol-1-yl]acetic acid

[(S)-5-cyano-6-fluoro-8-methyl-1-propyl-1,3,4,9-tetrahydropyrano[3,4b]indol-1-yl]acetic acid Resolution of (±)-5-Cyano-6-fluoro-8-methyl-1-propyl-1,3,4,9-tetrahydropyrano[3,4-b]indole-1-acetic Acid Preparative HPLC using CHIRALPACK-AD (250×20 mm) and 10% isopropyl alcohol in heptane (0.1% TFA) as eluant gave (R) and (S) enantiomers of 5-cyano-6-fluoro-8-methyl-1-propyl-1,3,4,9-tetrahydropyrano[3,4-b]indole-1-acetic acid as white solids. HRMS (ESI) [M+H]$^+$ calculated for C$_{18}$H$_{20}$FN$_2$O$_3$ 331.1453, found 331.1447 (R enantiomer) and 331.1452 (S enantiomer); Chiral HPLC HP 1100 with spiderlink CHIRALPACK-AD, 250×4.6 mm, isopropyl alcohol/heptane containing 0.1% TFA (10:90), 1.0 mL/minutes, DAD 215 nm; tR=7.19 minutes (R enantiomer), 9.27 minutes (S enantiomer).

Example 13–30 were synthesized following the above mentioned procedure for example 1 using the intermediates 4-Chloro or 4-Bromotryptophol and reacting with β-ketoesters like methylacetoacetate, ethylpropionyl acetate, ethylbutyryl acetate, ethylisobutyryl acetate, methyl-3-oxo-6-octenoate, ethylbenzoyl acetate, methyl-4-methoxycarbonyl benzoyl acetate, ethyl 3 or 4-nitrobenzoyl acetate, ethyl 2-fluorobenzoyl acetate, ethyl β-oxo-3-furan propionate or ethyl-3,4,5-trimethoxybenzoyl acetate. The resulting esters were hydrolyzed using 1N (aq) NaOH in THF/MeOH.

Examples 31–49 were synthesized following Suzuki reaction conditions using 5-bromo-1-propyl-1,3,4,9-tetrahydropyrano[3,4-b]indole-1-acetic Acid Ethyl Ester (1 eq), corresponding boronic acids (1.2 eq), Pd(Ph$_3$P)$_4$ (0.1 eq) and 2M Na$_2$CO$_3$ in dimethoxy ethane as solvent at 65° C. (overnight). The resulting esters were hydrolyzed using 1N (aq.) NaOH in THF/MeOH.

Examples 50–57 were synthesized following the above mentioned procedure for example 1 using the intermediate 4,7-dichlorotryptophol and reacting with β-ketoesters like methyl-3-oxo-6-octenoate, ethylisobutyryl acetate, ethylbenzoyl acetate, ethyl β-oxo-3-furan propionate, ethylisoamyl acetoacetate, ethyl-3,4,5-trimethoxybenzoyl acetate, ethyl 2-fluorobenzoyl acetate or methyl-4-methoxycarbonyl benzoyl acetate. The resulting esters were hydrolyzed using 1N (aq) NaOH in THF/MeOH.

Examples 58–66 were synthesized following the above mentioned procedure for example 1 using the intermediates 4-Bromotryptophol and reacting with β-ketoesters like ethylbutyryl acetate, ethylisobutyryl acetate, methyl-3-oxo-6-octenoate, ethyl β-oxo-3-furan propionate, ethylbenzoyl acetate, ehtyl-3,4,5-trimethoxybenzoyl acetate, ethyl 4 or 3-nitrobenzoyl acetate or ethyl 2-fluorobenzoyl acetate. The product was converted to the corresponding 5-cyano-1,3,4,9-tetrahydropyrano[3,4-b]indole-1-acetic Acid Ethyl Ester derivatives using CuCN in NMP using the microwave conditions provided in the Example 1. The resulting esters were hydrolyzed using 1N (aq) NaOH in THF/MeOH.

Examples 67–69 were synthesized following the above mentioned procedure for example 1 using the intermediates 4,7-dichloro or 4-bromo or 4-chlorortryptophol and reacting with 3-oxoenanthic acid methyl ester. The resulting esters were hydrolyzed using 1N (aq) NaOH in THF/MeOH.

Examples 70 and 71 were synthesized following the above mentioned procedure for example 1 using the intermediates 4-chlorortryptophol and reacting with dimethyl 1,3-acetonedicarboxylate. The resulting ester was hydrolyzed using 1N (aq) NaOH in THF/MeOH to give both 70 and 71.

Examples 72–88 were synthesized following the above mentioned procedure for example 1 using the intermediates 7-Chloro or 7-Bromotryptophol and reacting with β-ketoesters like methylacetoacetate, ethylpropionyl acetate, ethylbutyryl acetate, ethylisobutyryl acetate, 3-oxoenanthic acid methyl ester, methyl-3-oxo-6-octenoate, ethylbenzoyl acetate, ethyl β-oxo-3-furan propionate or methyl-4-methoxycarbonyl benzoyl acetate. The resulting esters were hydrolyzed using 1N (aq) NaOH in THF/MeOH.

Examples 89–97 were synthesized following Suzuki reaction conditions using 8-bromo-1-propyl-1,3,4,9-tetrahydropyrano[3,4-b]indole-1-acetic Acid Ethyl Ester (1 eq), corresponding boronic acids (1.2 eq), Pd(Ph3P)4 (0.1 eq) and 2M Na2CO3 in dimethoxy ethane as solvent at 650° C. (overnight). The resulting ester was hydrolyzed using 1N aq. NaOH in THF/MeOH.

Example 98 was synthesized using 8-bromo-1-propyl-1,3,4,9-tetrahydropyrano[3,4-b]indole-1-acetic Acid Ethyl Ester using CuCN in NMP using the microwave conditions provided in the Example 1. The resulting ester was hydrolyzed using 1N (aq) NaOH in THF/MeOH.

Examples 99–114 were synthesized following the above mentioned procedure for example 1 using the intermediates 5,7-dichloro or 6,7-dichloro or 4,6-dichlorotryptophol and reacting with β-ketoesters like methylacetoacetate, ethylpropionyl acetate, ethylbutyryl acetate, ethylisobutyryl acetate, 3-oxoenanthic acid methyl ester, methyl-3-oxo-6-octenoate, ethylbenzoyl acetate, methyl-4-methoxycarbonyl benzoyl acetate, ethyl 3 or 4-nitrobenzoyl acetate, ethyl 2-fluorobenzoyl acetate, ethyl β-oxo-3-furan propionate or ethyl-3,4,5-trimethoxybenzoyl acetate. The resulting esters were hydrolyzed using 1N (aq) NaOH in THF/MeOH.

Examples 115–121 were synthesized following the above mentioned procedure for example 1 using the intermediate 7-trifluoromethyltryptophol and reacting with β-ketoesters like methylacetoacetate, ethylpropionyl acetate, ethylbutyryl acetate, ethylisobutyryl acetate, 3-oxoenanthic acid methyl ester, methyl-3-oxo-6-octenoate, ethylbenzoyl acetate. The resulting esters were hydrolyzed using 1N(aq) NaOH in THF/MeOH.

Examples 122–128 were synthesized following the above mentioned procedure for example 1 using the intermediate 4,7-difluorotryptophol and reacting with β-ketoesters like methylacetoacetate, ethylpropionyl acetate, ethylbutyryl acetate, ethylisobutyryl acetate, 3-oxoenanthic acid methyl ester, methyl-3-oxo-6-octenoate or methyl-4-methoxycarbonyl benzoyl acetate. The resulting esters were hydrolyzed using 1N (aq) NaOH in THF/MeOH.

Examples 129–136 were synthesized following the above mentioned procedure for example 1 using the intermediate 7-chloro-4-trifluoromethyltryptophol and reacting with β-ketoesters like methylacetoacetate, ethylpropionyl acetate, ethylbutyryl acetate, ethylisobutyryl acetate, 3-oxoenanthic acid methyl ester, methyl-3-oxo-6-octenoate ethylbenzoyl acetate or ethyl β-oxo-3-furan propionate. The resulting esters were hydrolyzed using 1N (aq) NaOH in THF/MeOH.

Examples 137–139 were synthesized following the above mentioned procedure for example 1 using the intermediate 4,7dimethyltryptophol and reacting with β-ketoesters like methylacetoacetate, ethylpropionyl acetate or ethylbutyryl acetate. The resulting esters were hydrolyzed using 1N (aq) NaOH in THF/MeOH.

Examples 140–146 were synthesized following the above mentioned procedure for example 1 using the intermediate 4-fluoro-7-methyltryptophol and reacting with β-ketoesters like methylacetoacetate, ethylpropionyl acetate, ethylbutyryl acetate, ethylisobutyryl acetate, 3-oxoenanthic acid methyl ester, methyl-3-oxo-6-octenoate or ethylbenzoyl acetate. The resulting esters were hydrolyzed using 1N (aq) NaOH in THF/MeOH.

Examples 147–151 were synthesized following Suzuki reaction conditions using 5-bromo-8-fluoro-1-propyl-1,3,4,9-tetrahydropyrano[3,4-b]indole-1-acetic Acid Ethyl Ester (1 eq), corresponding boronic acids (1.2 eq), Pd(Ph3P)4 (0.1 eq) and 2M Na2CO3 in dimethoxy ethane as solvent at 650 C (overnight). The resulting ester was hydrolyzed using 1N (aq) NaOH in THF/MeOH.

Example 152 was synthesized by hydrolyzing the intermediate 5-bromo-8-fluoro-1-propyl-1,3,4,9-tetrahydropyrano[3,4-b]indole-1-acetic acid ethyl ester in example 4 using 1N (aq) NaOH in THF/MeOH.

Example 153 was synthesized by hydrolyzing the intermediate 5-bromo-8-methyl-1-propyl-1,3,4,9-tetrahydropyrano[3,4-b]indole-1-acetic acid ethyl ester in example 1 using 1N (aq) NaOH in THF/MeOH.

Examples 154–162 were synthesized following the above mentioned procedure for example 1 using the intermediate 4,5,7-trichlorotryptophol and reacting with β-ketoesters like methylacetoacetate, ethylpropionyl acetate, ethylbutyryl acetate, ethylisobutyryl acetate, 3-oxoenanthic acid methyl ester, methyl-3-oxo-6-octenoate or ethylbenzoyl acetate or ethyl β-oxo-3-furan propionate. The resulting esters were hydrolyzed using 1N (aq) NaOH in THF/MeOH.

Examples 163–169 were synthesized following the above mentioned procedure for example 1 using the intermediate 4-bromo-7-fluoro-5-methyltryptophol and reacting with β-ketoesters like methylacetoacetate, ethylpropionyl acetate, ethylbutyryl acetate, ethylisobutyryl acetate, 3-oxoenanthic acid methyl ester, ethylbenzoyl acetate, methyl-3-oxo-6-octenoate or methyl-4-methoxycarbonyl benzoyl acetate. The resulting esters were hydrolyzed using 1N (aq) NaOH in THF/MeOH.

Examples 170–172 were synthesized using 1-butyl-5-bromo-8-fluoro-6-methyl-1,3,4,9-tetrahydropyrano[3,4-b]indole-1-acetic acid ethyl ester or 5-bromo-8-fluoro-6-methyl-1-phenyl-1,3,4,9-tetrahydropyrano[3,4-b]indole-1-acetic acid ethyl ester or 5-bromo-1-(4'carbonylethoxyphenyl)-8-fluoro-6-methyl-1,3,4,9-tetrahydropyrano[3,4-b]indole-1acetic acid ethyl ester using CuCN in NMP using the microwave conditions provided in the Example 1. The resulting esters were hydrolyzed using 1N (aq) NaOH in THF/MeOH.

Examples 173–180 were synthesized following the above mentioned procedure for example 1 using the intermediate 4-bromo-7-chloro-5-methyltryptophol and reacting with β-ketoesters like methylacetoacetate, ethylpropionyl acetate, ethylbutyryl acetate, ethylisobutyryl acetate, 3-oxoenanthic acid methyl ester, methyl-3-oxo-6-octenoate, ethylbenzoyl acetate, or methyl-4-methoxycarbonyl benzoyl acetate. The resulting esters were hydrolyzed using 1N (aq) NaOH in THF/MeOH.

Examples 181–188 were synthesized from the intermediate esters from the examples 173–180 using CuCN in NMP using the microwave conditions provided in the Example 1. The resulting esters were hydrolyzed using 1N (aq) NaOH in THF/MeOH.

Examples 189–193 were synthesized following the above mentioned procedure for example 1 using the intermediate 4-bromo-5,7-difluorotryptophol and reacting with β-ketoesters like ethylpropionyl acetate, ethylbutyryl acetate, 3-oxoenanthic acid methyl ester, ethyl β-oxo-3-furan propionate or ethylisobutyryl acetate. The resulting esters were hydrolyzed using 1N (aq) NaOH in THF/MeOH.

Examples 194–198 were synthesized from the intermediate esters from the examples 189–193 using CuCN in NMP using the microwave conditions provided in the Example 1. The resulting esters were hydrolyzed using 1N (aq) NaOH in THF/MeOH.

Examples 199–204 were synthesized following the above mentioned procedure for example 1 using the intermediate 4-bromo-5-fluoro-7-methyltryptophol and reacting with β-ketoesters like ethylpropionyl acetate, ethylbutyryl acetate, ethylisobutyryl acetate, 3-oxoenanthic acid methyl ester or methyl-4-methoxycarbonyl benzoyl acetate. The resulting esters were hydrolyzed using 1N (aq) NaOH in THF/MeOH.

Examples 205–209 were synthesized from the intermediate esters from the examples 199–204 using CuCN in NMP using the microwave conditions provided in the Example 1. The resulting esters were hydrolyzed using 1N (aq) NaOH in THF/MeOH.

Examples 210–213 were synthesized following the above mentioned procedure for example 1 using the intermediate 4,7-dibromotryptophol and reacting with β-ketoesters like ethylpropionyl acetate, ethylbutyryl acetate, ethylisobutyryl acetate or 3-oxoenanthic acid methyl ester. The resulting esters were hydrolyzed using 1N (aq) NaOH in THF/MeOH.

Example 214–218 were synthesized using the ethyl ester of examples 152, 175 and 165 as intermediates using CuCl or CuI in NMP using the microwave conditions provided in the Example 1. The resulting esters were hydrolyzed using 1N (aq) NaOH in THF/MeOH.

Examples 219–223 were synthesized following the above mentioned procedure for example 1 using the intermediate 4-bromo-5-methyl-7-fluorotryptophol and reacting with β-ketoesters like methylacetoacetate, ethylpropionyl acetate, ethylisobutyryl acetate or methyl-3-oxo-6-octenoate. The intermediate esters were converted to the cyano compounds using CuCN in NMP using the microwave conditions provided in the Example 1. The resulting esters were hydrolyzed using 1N (aq) NaOH in THF/MeOH.

EXAMPLE 224

(8-Methyl-5-methylcarbamoyl-1-propyl-1,3,4,9-tetrahydro-pyrano[3,4-b]indol-1-yl)-acetic Acid 4-Bromo-3-[2-(tert-butyl-dimethyl-silanyloxy)-ethyl]-7-methyl-1H-indole A mixture of 2-(4-bromo-7-methyl-1H-indol-3-yl)-ethanol (2.51 g, 9.89 mmol), imidazole (1.68 g, 24.7 mmol) and tert-butyldimethylsilyl chloride (1.79 g, 11.9 mmol) in DMF (30 mL) was stirred overnight at room temperature. The reaction mixture was diluted with EtOAc (200 mL). The organic solution was washed with $H_2O$ (5×200 mL) and brine (200 mL), dried ($Na_2SO_4$), and concentrated to give 3.49 g (96%) of title compound as yellow oil. 1H NMR ($CDCl_3$): 300 MHz δ 8.14 (bs, 1H), 7.11 (d, J=7.59 Hz, 1H), 6.99 (s, 1H), 6.72 (d, J=7.59 Hz, 1H), 3.90 (t, J=7.17 Hz, 2H), 3.19 (t, J=7.17 Hz, 2H), 2.31 (s, 3H), 0.87 (s, 9H), −0.08 (s, 6H).

3-[2-(tert-Butyl-dimethyl-silanyloxy)-ethyl]-7-methyl-1H-indole-4-carboxylic acid To a suspension of KH (1.85 g of 30 wt % in oil, 13.85 mmol) in THF (100 mL) was added a solution of 4-bromo-3-[2-(tert-butyl-dimethyl-silanyloxy)-ethyl]-7-methyl-1H-indole (3.40 g, 9.24 mmol) in THF (10 mL) at 0° C. After stirring for 40 minutes, the solution was cooled to −78° C. and tert-BuLi (10.9 mL of 1.7 M in pentane, 18.47 mmol), precooled to −78° C., was added. After stirring for 1 hour at −78° C., the reaction mixture was transferred to the flask containing anhydrous $CO_2$ (dry ice, 100 g) via cannula under $N_2$ atmosphere at −78° C. The suspension was warmed to room temperature very slowly using cold bath. The mixture was diluted with EtOAc (200 mL) and the organic solution was washed with 1 N HCl (2×200 mL), $H_2O$ (200 mL) and brine (200 mL). The organic phase was dried ($Na_2SO_4$) and concentrated. The residue was purified by flash chromatography (silica, 15% EtOAc in hexanes) to give 0.74 g (41% based on the recovered SM) of title compound as a white solid. 1H NMR ($CDCl_3$): 300 MHz δ 8.26 (bs, 1H), 7.84 (d, J=7.56 Hz, 1H), 7.32 (d, J=2.46 Hz, 1H), 7.12 (d, J=7.56 Hz, 1H), 3.98 (t, J=6.39 Hz, 2H), 3.33 (t, J=6.39 Hz, 2H), 2.63 (s, 3H), 0.89 (s, 9H), −0.08 (s, 6H).

3-[2-(tert-Butyl-dimethyl-silanyloxy)-ethyl]-7-methyl-1H-indole-4-carboxylic acid methylamide To a solution of 3-[2-(tert-butyl-dimethyl-silanyloxy)-ethyl]-7-methyl-1H-indole-4-carboxylic acid (150 mg, 0.45 mmol), EDCI (104 mg, 0.54 mmol) and HOBt (91.2 mg, 0.68 mmol) in DMF (3 mL) was added diisopropylethylamine (0.39 mL, 2.25 mmol) at room temperature. A solution of methylamine (0.45 mL of 2.0 M in THF, 0.90 mmol) was added to the mixture and the mixture was stirred overnight at room temperature. The solution was diluted with $H_2O$ (5 mL) and extracted with EtOAc (3×10 mL). The organic solution was washed brine (20 mL), dried ($Na_2SO_4$) and concentrated. The residue was purified by flash chromatography (silica, 40% EtOAc in hexanes) to give 140 mg (90%) of title compound as a pale yellow solid. 1H NMR ($CDCl_3$): 300 MHz δ 8.28 (bs, 1H), 7.20 (m, 2H), 7.00 (d, J=7.35 Hz, 1H), 6.40 (bs, 1H), 3.91 (t, J=6.41 Hz, 2H), 3.08 (m, 5H), 2.54 (s, 3H), 0.88 (s, 9H), −0.08 (s, 6H).

(8-Methyl-5-methylcarbamoyl-1-propyl-1,3,4,9-tetrahydro-pyrano[3,4-b]indol-1-yl)-acetic Acid Ethyl Ester To a solution of 3-[2-(tert-butyl-dimethyl-silanyloxy)-ethyl]-7-methyl-1H-indole-4-carboxylic acid methylamide (100 mg, 0.289 mmol) and ethyl butyrylacetate (92 mL, 0.578 mmol) in $CH_2Cl_2$ (2 mL) was added $BF_3.OEt2$ (0.11 mL, 0.867 mmol) dropwise at room temperature. After stirring overnight, the solution was diluted with $CH_2Cl_2$ (10 mL) and then washed with saturated aqueous $NaHCO_3$ (10 mL) and brine (10 mL). The organic phase was dried ($Na_2SO_4$) and concentrated. The residue was purified by flash chromatography (silica, 50% EtOAc in hexanes) to give 88 mg (82%) of title compound as a yellow solid. 1H NMR ($CDCl_3$): 300 MHz δ 9.54 (bs, 1H), 7.12 (d, J=7.38 Hz, 1H), 6.89 (d, J=7.38 Hz, 1H), 6.05 (d, J=4.71 Hz, 1H), 4.15 (m, 2H), 3.96 (m, 1H), 3.86 (m, 1H), 3.03–2.83 (m, 7H), 2.48 (s, 3H), 2.00 (m, 2H), 1.37 (m, 1H), 1.25 (t, J=6.84 Hz, 3H), 1.22 (m, 1H), 0.87 (t, J=7.17 Hz, 3H).

(8-Methyl-5-methylcarbamoyl-1-propyl-1,3,4,9-tetrahydro-pyrano[3,4-b]indol-1-yl)-acetic Acid To a solution of (8-methyl-5-methylcarbamoyl-1-propyl-1,3,4,9-tetrahydro-pyrano[3,4-b]indol-1-yl)-acetic acid ethyl ester (87 mg, 0.234 mmol) in THF/MeOH (1.5 mL/1.5 mL) was added 1 N NaOH (0.468 mL, 0.468 mmol). The reaction mixture was stirred at ambient temperature overnight. The most of THF/MeOH was removed under reduced pressure and the resulting mixture was acidified with 1 N HCl. The mixture was extracted with EtOAc (3×10 mL). The combined organic phase was washed with brine (20 mL), dried over $Na_2SO_4$ and concentrated. The residue was purified by preparative HPLC to give 67 mg (84%) of title compound as a white solid. Mp=89–91° C.; HRMS (ESI) [M+H]$^+$ calculated for $C_{19}H_{25}N_2O_4$ 345.1809, found 345.1807; 1H NMR (DMSO-d$_6$): 300 MHz δ 10.63 (s, 1H), 8.00 (s, 1H), 6.97 (d, J=6.00 Hz, 1H), 6.84 (d, J=6.00 Hz, 1H), 3.89 (m, 1H), 3.81 (m, 1H), 2.93–2.46 (m, 10H), 2.01 (m, 2H), 1.29 (m, 1H), 0.82 (m, 1H), 0.78 (t, J=5.10 Hz, 3H). LCMS retention time: 1.936 minutes.

EXAMPLE 225

[8-Fluoro-5-(morpholine-4-carbonyl)-1-propyl-1,3,4,9-tetrahydro-pyrano[3,4-b]indol-1-yl]-acetic Acid 5-Bromo-1-[2-(tert-butyl-dimethyl-silanyloxy)-ethyl]-8-fluoro-1-propyl-1,3,4,9-tetrahydro-pyrano[3,4-b]indole To a solution of (5-bromo-8-fluoro-1-propyl-1,3,4,9-tetrahydro-pyrano[3,4-b]indol-1-yl)-acid ethyl ester (2.0 g, 5.02 mmol) in THF (10 mL) was added LAH (5.27 mL of 1.0 M in THF, 5.27 mmol) slowly at room temperature. The mixture was stirred for 30 minutes at room temperature. The reaction mixture was quenched by the addition of H$_2$O (0.5 mL) and then 10% NaOH (0.5 mL) was added to the mixture. Na$_2$SO$_4$ was added to the mixture and the resulting mixture was filtered. The filtrate was concentrated to give 1.79 g (100%) of 2-(5-bromo-8-fluoro-1-propyl-1,3,4,9-tetrahydro-pyrano[3,4-b]indol-1-yl)-ethanol as yellow oil. A mixture of 2-(5-bromo-8-fluoro-1-propyl-1,3,4,9-tetrahydro-pyrano[3,4-b]indol-1-yl)-ethanol (1.79 g, 5.02 mmol), imidazole (0.854 g, 12.55 mmol) and tert-butyldimethylsilyl chloride (0.909 g, 6.03 mmol) in DMF (10 mL) was stirred overnight at room temperature. The reaction mixture was diluted with EtOAc (100 mL). The organic solution was washed with H$_2$O (5×100 mL) and brine (100 mL), dried (Na$_2$SO$_4$), and concentrated. The residue was purified by flash chromatography (silica, 7% EtOAc in hexanes) to give 2.29 g (97%) of title compound as a white solid. 1H NMR (CDCl$_3$): 300 MHz δ 8.97 (bs, 1H), 6.95 (dd, J=8.37, 4.17 Hz, 1H), 6.57 (d, J=10.41, 8.37 Hz, 1H), 3.98–3.54 (m, 4H), 3.00 (m, 2H), 2.00–0.90 (m, 6H), 0.80 (s, 9H), 0.74 (d, J=7.32 Hz, 3H), 0.06 (s, 3H), 0.03 (s, 3H).

1-[2-(tert-Butyl-dimethyl-silanyloxy)-ethyl]-8-fluoro-1-propyl-1,3,4,9-tetrahydro-pyrano[3,4-b]indole-5-carboxylic acid To a suspension of KH (0.36 g of 30 wt % in oil, 2.70 mmol) in THF (20 mL) was added a solution of 5-bromo-1-[2-(tert-butyl-dimethyl-silanyloxy)-ethyl]-8-fluoro-1-propyl-1,3,4,9-tetrahydro-pyrano[3,4-b]indole (0.845 g, 1.80 mmol) in THF (2 mL) at 0° C. After stirring for 30 minutes, the solution was cooled to −78° C. and tert-BuLi (2.18 mL of 1.7 M in pentane, 3.60 mmol), precooled to −78° C., was added. After stirring for 30 minutes at −78° C., the reaction mixture was transferred to the flask containing anhydrous CO$_2$ (dry ice, 8 g) via cannula under N$_2$ atmosphere at −78° C. The suspension was warmed to room temperature very slowly using cold bath. The mixture was diluted with EtOAc (100 mL) and the organic solution was washed with 1 N HCl (2×100 mL), H$_2$O (100 mL) and brine (100 mL). The organic phase was dried (Na$_2$SO$_4$) and concentrated. The residue was purified by flash chromatography (silica, 40% EtOAc in hexanes) to give 0.60 g (77%) of title compound as a white solid. 1H NMR (CDCl$_3$): 300 MHz δ 11.55 (bs, 1H), 9.37 (s, 1H), 7.75 (dd, J=8.50, 5.04 Hz, 1H), 6.74 (dd, J=10.05, 8.50 Hz, 1H), 3.89 (m, 1H), 3.80 (m, 2H), 3.61 (m, 1H), 3.03 (m, 1H), 2.05 (m, 2H), 1.74 (m, 1H), 1.31 (m, 1H), 1.14 (m, 1H), 1.01 (m, 1H), 0.80 (s, 9H), 0.75 (t, J=7.38 Hz, 3H), 0.06 (s, 3H), 0.03 (s, 3H).

{1-[2-(tert-Butyl-dimethyl-silanyloxy)-ethyl]-8-fluoro-1-propyl-1,3,4,9-tetrahydro-pyrano[3,4-b]indol-5-yl}-morpholin-4-yl-methanone To a solution of 1-[2-(tert-butyl-dimethyl-silanyloxy)-ethyl]-8-fluoro-1-propyl-1,3,4,9-tetrahydro-pyrano[3,4-b]indole-5-carboxylic acid (6) (400 mg, 0.918 mmol), EDCI (211 mg, 1.10 mmol) and HOBt (186 mg, 1.38 mmol) in DMF ( 5 mL) was added diisopropylethylamine (0.80 mL, 4.59 mmol) at room temperature. Morpholine (0.12 mL, 1.38 mmol) was added to the mixture and the mixture was stirred overnight at room temperature. The solution was diluted with H$_2$O (10 mL) and extracted with EtOAc (3×15 mL). The organic solution was brine washed (30 mL), dried (Na$_2$SO$_4$) and concentrated. The residue was purified by flash chromatography (silica, 50% EtOAc in hexanes) to give 415 mg (90%) of title compound as a colorless oil. 1H NMR (CDCl$_3$): 300 MHz δ 9.38 (s, 1H), 6.77 (m, 2H), 3.86–3.20 (m, 12 H), 2.67 (m, 2H), 1.97–1.15 (m, 6H), 0.81 (s, 9H), 0.76 (t, J=7.34 Hz, 3H), 0.06 (s, 3H), 0.03 (s, 3H).

[8-Fluoro-5-(morpholine-4-carbonyl)-1-propyl-1,3,4,9-tetrahydro-pyrano[3,4-b]indol-1-yl]-acetaldehyde To a solution of {1-[2-(tert-Butyl-dimethyl-silanyloxy)-ethyl]-8-fluoro-1-propyl-1,3,4,9-tetrahydro-pyrano[3,4-b]indol-5-yl}-morpholin-4-yl-methanone (350 mg, 0.693 mmol) in THF (5 mL) was added TBAF (0.832 mL of 1.0 M in THF, 0.832 mmol) at room temperature. After stirring for 4 hours at room temperature, the reaction mixture was diluted with EtOAc (20 mL). The organic solution was washed with 0.5 N HCl (20 mL) and brine (20 mL), dried (Na$_2$SO$_4$) and concentrated. The residue was purified by flash chromatography (silica, 50% EtOAc in hexanes) to give 254 mg (94%) of [8-fluoro-1-(2-hydroxy-ethyl)-1-propyl-1,3,4,9-tetrahydro-pyrano[3,4-b]indol-5-yl]-morpholin-4-yl-methanone as white solid.

The mixture of [8-fluoro-1-(2-hydroxy-ethyl)-1-propyl-1,3,4,9-tetrahydro-pyrano[3,4-b]indol-5-yl]-morpholin-4-yl-methanone (100 mg, 0.256 mmol) and o-iodoxybenzoic acid (IBX, 430 mg, 1.54 mmol) in DMSO (3.5 mL) was stirred overnight at room temperature. The solution was diluted with H$_2$O (7 mL) and the precipitates were filtered and the filter cake was rinsed with EtOAc. The filtrate was extracted with EtOAc (3×10 mL) and the combined organic solution was washed with brine (20 mL), dried (Na$_2$SO$_4$) and concentrated. The residue was purified by flash chromatography (silica, 60% EtOAc in hexanes) to give 89 mg (90%) of the title compound as a pale yellow solid. 1H NMR (CDCl$_3$): 300 MHz δ 9.75 (bs, 1H), 9.05 (bs, 1H), 6.89 (m, 2H), 4.00–2.64 (m, 14H), 1.89 (m, 1H), 1.63 (s, 1H), 1.26 (m, 2H), 0.88 (t, J=5.49 Hz, 3H).

[8-Fluoro-5-(morpholine-4-carbonyl)-1-propyl-1,3,4,9-tetrahydro-pyrano[3,4-b]indol-1-yl]-acetic Acid To a solution of [8-fluoro-5-(morpholine-4-carbonyl)-1-propyl-1,3,4,9-tetrahydro-pyrano[3,4-b]indol-1-yl]-acetaldehyde (8) (99 mg, 0.255 mmol) in DMSO (3.5 mL) was added a solution of NaH$_2$PO$_4$ in H$_2$O (0.36 mL of 0.7 M in H$_2$O, 0.255 mmol) at room temperature. To the mixture was added a solution of NaClO$_2$ in H$_2$O (1.52 mL of 0.5 M in H$_2$O, 0.765 mmol). After stirring for 20 hours at room temperature, the mixture was acidified with HCl. The resulting mixture was extracted with EtOAc (3×10 mL). The combined organic phase was washed with brine (20 mL), dried over Na$_2$SO$_4$ and concentrated. The residue was purified by preparative HPLC to give 77 mg (75%) of title compound as a white solid. Mp=98–100° C.; HRMS (ESI) [M+H]$^+$ calculated for $C_{21}H_{26}FN_2O_5$ 405.1820, found 405.1821; 1H NMR (DMSO-d$_6$): 300 MHz δ 12.30 (bs, 1H), 11.45 (s, 1H), 6.95–6.85 (m, 2H), 3.92 (m, 2H), 3.66 (m, 2H), 3.45 (m, 1H), 3.15 (m, 1H), 2.94 (d, J=10.2 Hz, 2H), 2.70 (d, J=10.2 Hz, 2H), 2.59 (m, 1H), 2.57 (s, 1H), 2.51 (m, 2H), 1.99 (t, J=5.10 Hz, 2H), 1.31 (m, 1H), 0.86 (m, 1H), 0.08 (t, J=5.10 Hz, 3H). LCMS retention time: 2.073 minutes.

EXAMPLE 226

(5-Carbamoyl-8-methyl-1-propyl-1,3,4,9-tetrahydro-pyrano[3,4-b]indol-1-yl)-acetic acid The compound was synthesized by using the same procedures that were used for the synthesis of Example 224 except using ammonium chloride and PyBop instead of methylamine and EDCI. LCMS retention time: 1.756 minutes, [M+H]$^+$ calculated for $C_{18}H_{23}N_2O_4$ 331.39, found 331.10; [M−1]$^+$ calculated for $C_{18}H_{21}N_2O_4$ 329.39, found 329.10.

EXAMPLE 227

(5-Dimethylcarbamoyl-8-methyl-1-propyl-1,3,4,9-tetrahydro-pyrano[3,4-b]indol-1-yl)-acetic Acid The compound was synthesized by using the same procedures that were used for the synthesis of Example 224 except using dimethylamine instead of methylamine. LCMS retention time: 2.127 minutes, [M+H]$^+$ calculated for $C_{20}H_{27}N_2O_4$ 359.44, found 359.10; [M−1]$^+$ calculated for $C_{20}H_{25}N_2O_4$ 357.44, found 357.10.

EXAMPLE 228

(5-Cyano-8-fluoro-3-methyl-1-propyl-1,3,4,9-tetrahydro-pyrano[3,4-b]indol-1-yl)-acetic Acid (4-Bromo-7-fluoro-1H-indol-3-yl)-acetaldehyde The mixture of 2-(4-bromo-7-fluoro-1H-indol-3-yl)-ethanol (3.00 g, 11.6 mmol) and o-iodoxybenzoic acid (IBX, 9.76 g, 34.9 mmol) in DMSO (60 mL) was stirred overnight at room temperature. The solution was diluted with H$_2$O (100 mL) and the precipitates were filtered and the filter cake was rinsed with EtOAc. The filtrate was extracted with EtOAc (3×150 mL) and the combined organic solution was washed with brine (300 mL), dried (Na$_2$SO$_4$) and concentrated. The residue was purified by flash chromatography (silica, 25% EtOAc in hexanes) to give 2.48 g (83%) of the title compound as a pale yellow solid. 1H NMR (CDCl$_3$): 300 MHz δ 9.93 (s, 1H), 8.44 (bs, 1H), 7.20 (m, 1H), 7.17 (dd, J=8.40, 4.32 Hz, 1H), 6.80 (dd, J=10.2, 8.40 Hz, 1H), 4.12 (s, 2H).

1-(4-Bromo-7-fluoro-1H-indol-3-yl)-propan-2-ol

To a solution of (4-bromo-7-fluoro-1H-indol-3-yl)-acetaldehyde (358 mg, 1.40 mmol) in THF (10 mL) was added a solution of MeMgBr (4.0 mL of 1.4 M in toluene-THF (75:25), 5.59 mmol) at room temperature. The mixture was stirred overnight at room temperature. The reaction mixture was quenched with H$_2$O and extracted with EtOAc (3×20 mL). The combined organic phase was washed with brine (50 mL), dried over Na$_2$SO$_4$ and concentrated. The residue was purified by flash chromatography (silica, 30% EtOAc in hexanes) to give 158 mg (42%) of the title compound as a white solid. 1H NMR (CDCl$_3$): 300 MHz δ 8.97 (bs, 1H), 7.11 (dd, J=8.10, 4.20 Hz, 1H), 6.70 (dd, J=10.2, 8.10 Hz, 1H), 4.18 (m, 1H), 3.29(dd, J=14.5, 3.93 Hz, 1H), 2.87 (dd, J=14.5, 8.43 Hz, 1H), 2.16 (bs, 1H), 1.29 (d, J=6.18 Hz, 3H).

(5-Cyano-8-fluoro-3-methyl-1-propyl-1,3,4,9-tetrahydro-pyrano[3,4-b]indol-1-yl)-acetic Acid Ethyl Ester To a solution of 1-(4-bromo-7-fluoro-1H-indol-3-yl)-propan-2-ol (155 mg, 0.570 mmol) and ethyl butyrylacetate (0.137 mL, 0.854 mmol) in CH$_2$Cl$_2$ (3 mL) was added BF$_3$.OEt$_2$ (0.11 mL, 0.854 mmol) dropwise at room temperature. After stirring for 3 hours, the mixture was diluted with CH$_2$Cl$_2$ (15 mL) and then washed with saturated aqueous NaHCO$_3$ (15 mL) and brine (15 mL). The organic phase was dried (Na$_2$SO$_4$) and concentrated. The residue was purified by flash chromatography (silica, 10% EtOAc in hexanes) to give (5-bromo-8-fluoro-3-methyl-1-propyl-1,3, 4,9-tetrahydro-pyrano[3,4-b]indol-1-yl)-acetic acid ethyl ester as a pale yellow solid (this sample contains ethyl butyrylacetate).

(5-Bromo-8-fluoro-3-methyl-1-propyl-1,3,4,9-tetrahydro-pyrano[3,4-b]indol-1-yl)-acid ethyl ester (235 mg, 0.570 mmol) and CuCN (77 mg, 0.854 mmol) was dissolved in N-methyl-2-pyrrolidinone (3 mL). The reaction vessels were heated in microwave at 220° C. for 15 minutes. The reaction mixtures was diluted with water (3 mL). The crude mixture was extracted with EtOAc (3×10 mL). The combined organic phase was washed with brine (30 mL), dried over Na$_2$SO$_4$ and concentrated. The residue was purified by flash chromatography (silica, 10% EtOAc in hexanes) to give 156 mg (76% in two steps) of title compound as a yellow oil. 1H NMR (CDCl$_3$): 300 MHz δ 10.16 (bs, 1H), 7.37 (m, 1H), 6.88 (m, 1H), 4.27 (m, 2H), 4.04 (m, 1H), 3.14 (m, 2H), 2.73 (m, 2H), 2.00 (m, 2H), 1.57 (m, 1H), 1.40 (d, J=6.12 Hz, 3H), 1.29 (m, 4H), 0.95 (t, J=7.32 Hz, 3H).

(5-Cyano-8-fluoro-3-methyl-1-propyl-1,3,4,9-tetrahydro-pyrano[3,4-b]indol-1-yl)-acetic Acid To a solution of (5-cyano-8-fluoro-3-methyl-1-propyl-1, 3,4,9-tetrahydro-pyrano[3,4-b]indol-1-yl)-acetic Acid Ethyl Ester (156 mg, 0.435 mmol) in THF/MeOH (1.5 mL/1.5 mL) was added 1 N NaOH (0.871 mL, 0.871 mmol). The reaction mixture was stirred at ambient temperature overnight. The most of THF/MeOH was removed under reduced pressure and the resulting mixture was acidified with 1 N HCl. The mixture was extracted with EtOAc (3×10 mL). The combined organic phase was washed with brine (20 mL), dried over Na$_2$SO$_4$ and concentrated. The residue was purified by preparative HPLC to give 125 mg (87%) of title compound as a white solid. LCMS retention time: 2.775 minutes, [M+H]$^+$ calculated for $C_{18}H_{20}FN_2O_3$ 331.36, found 331.10, [M−1]$^+$ calculated for $C_{18}H_{18}FN_2O$ 329.36, found 329.10.

EXAMPLE 229

(5,8-Dichloro-4-methyl-1-propyl-1,3,4,9-tetrahydro-pyrano[3,4-b]indol-1-yl)acetic acid To a solution of [2-(4,7-dichloro1H-indol-3-yl)-propan-1-ol] (500 mg) (prepared following the procedure described in EP 0238226) in DCM (50 mL) was added ethyl butyrylacetate (488 mg, 3.08 mmol), BF$_3$.Et$_2$O (437 mg, 3.08 mmol) and stirred at room temperature overnight. The solution was then washed with saturated aqueous NaHCO$_3$ and brine. Dried over Na$_2$SO$_4$ and flashed over silica gel (hexane: EtOAc 4:1) to yield white/blue crystals 700 mg (88%).

To a solution of above ester (700 mg, 1.83 mmol) in EtOH was added 1 N NaOH and heated in oil bath at 60° C. for 4 hours. The resulting mixture was then concentrated down where 35 mg was purified on HPLC to yield white solid 25 mg. LCMS retention time: 3.308 minutes, 355 [M–H]+.

Example 230–231 were prepared following the above mentioned procedure for example 229 starting from [2-(4, 7-dichloro1H-indol3-yl)-2-methylpropan-1-ol] and [2-(4,7-dichloro-1-indol-3-yl)cyclobutylmethanol].

EXAMPLE 232

(5,8-Dichloro-9-methyl-1-propyl-1,3,4,9-tetrahydropyrano[3,4-b]indol-1-yl)acetic acid To a solution of (5,8-dichloro-1-propyl-1,3,4,9-tetrahydropyrano[3,4-b]indol-1-yl)-acetic acid ethyl ester (160 mg, 0.432 mmol) in N,N, dimethylformamide (4.5 mL) was added sodium hydride (20.7 mg, 0.866 mmol). The reaction was stirred for 30 minutes and then added iodomethane (184 mg, 1.30 mmol). The reaction mixture was microwaved at 170° C. for 12 minutes. The resulting mixture was concentrated down and purified by flash column. The ester was dissolved in EtOH (4 ml) and 1 N NaOH (1 mL) and stirred at 50° C. for 3 hours. The EtOH/NaOH was removed under reduced pressure and the resulting mixture was purified on HPLC to yield a white solid.

Examples 233–234 were prepared following the above mentioned procedure for example 232 starting using allyl bromide and benzyl bromide in the place of methyl iodide.

Examples 235–239 were synthesized following the above mentioned procedure for example 1 using the intermediate 4,5-dichlorotryptophol and reacting with β-ketoesters like ethyl 3-cyclobutyl-3-oxopropionate, ethyl 3-cyclopentyl-3-oxopropionate, methyl 4-methoxy-3-oxobutyrate, methyl 5-methoxy-3-oxopentanoate, or ethyl 6,6,6-trifluoro-3-oxohexanoate. The resulting esters were hydrolyzed using aqueous NaOH in THF/EtOH.

Examples 240 and 241 were synthesized following the above mentioned procedure for example 1 using the intermediate 5,6-dichlorotryptophol and reacting with β-ketoesters like ethyl butyrylacetate or ethyl 4-ethoxy-3-oxobutyrate. The resulting esters were hydrolyzed using aqueous NaOH in THF/EtOH.

Examples 242–258 were synthesized following the above mentioned procedure for example 1 using the intermediate 4,7-dichlorotryptophol and reacting with β-ketoesters like methyl acetoacetate, ethyl propionylacetate, ethyl 5-cyano-3-oxopentanoate, ethyl 3-oxo-6-butenoate, ethyl 3-cyclopropyl-3-oxopropionate, ethyl 3-cyclobutyl-3-oxopropionate, ethyl 3-cyclopentyl-3-oxopropionate, ethyl 3-cyclohexyl-3-oxopropionate, ethyl 4-cyclopropyl-3-oxobutyrate, ethyl 4-cyclopentyl-3-oxobutyrate, (±)-ethyl 4-methyl-3-oxopentanoate, methyl 4-methoxy-3-oxobutyrate, methyl 5-methoxy-3-oxopentanoate, ethyl 4-ethoxy-3-oxobutyrate, methyl 3-oxo-4-thiomethylbutyrate, methyl 3-oxo-4-thioethylbutyrate, or ethyl 6,6,6-trifluoro-3-oxohexanoate. The resulting esters were hydrolyzed using aqueous NaOH in THF/EtOH.

Examples 259 and 260 were synthesized following the above mentioned procedure for example 1 using the intermediate 4-chloro-7-methyltryptophol and reacting with β-ketoesters like ethyl 3-cyclobutyl-3-oxopropionate, or ethyl butyrylacetate. The resulting esters were hydrolyzed using aqueous NaOH in THF/EtOH.

Example 262 was synthesized following the above mentioned procedure for example 1 using the intermediate 7-chloro-4-methyltryptophol and reacting with β-ketoesters like ethyl butyrylacetate. The resulting ester was hydrolyzed using aqueous NaOH in THF/EtOH.

Examples 263–267 were synthesized following the above mentioned procedure for example 1 using the intermediate 7-chloro-4-trifluoromethyltryptophol and reacting with β-ketoesters like ethyl 3-cyclobutyl-3-oxopropionate, methyl 4-methoxy-3-oxobutyrate, methyl 5-methoxy-3-oxopentanoate, ethyl 4-ethoxy-3-oxobutyrate, or ethyl 6,6,6-trifluoro-3-oxohexanoate. The resulting esters were hydrolyzed using aqueous NaOH in THF/EtOH.

Examples 268–270 were synthesized following the above mentioned procedure for example 1 using the intermediate 7-fluoro-4-trifluoromethyltryptophol and reacting with β-ketoesters like ethyl butyrylacetate, ethyl 3-cyclobutyl-3-oxopropionate, or ethyl 3-cyclopentyl-3-oxopropionate. The resulting esters were hydrolyzed using aqueous NaOH in THF/EtOH.

Example 271 was synthesized following the above mentioned procedure for example 1 using the intermediate 4,7-bis(trifluoromethyl)tryptophol and reacting with β-ketoesters like ethyl butyrylacetate. The resulting esters were hydrolyzed using aqueous NaOH in THF/EtOH.

Examples 272–275 were synthesized following the above mentioned procedure for example 1 using the intermediate 4-trifluoromethyl-7-methyltryptophol and reacting with β-ketoesters like ethyl butyrylacetate, ethyl 3-oxoheptanoate, ethyl 3-cyclobutyl-3-oxopropionate, or ethyl 3-cyclopropyl-3-oxopropionate. The resulting esters were hydrolyzed using aqueous NaOH in THF/EtOH.

Examples 276 and 277 were synthesized following the above mentioned procedure for example 1 using the intermediate 7-bromo-4-trifluoromethyltryptophol and reacting with β-ketoesters like ethyl butyrylacetate, or ethyl 3-cyclobutyl-3-oxopropionate. The bromo substituent was converted to a cyano group using CuCN in N-methyl-2-pyrrolidinone as described in example 1. The resulting esters were hydrolyzed using aqueous NaOH in THF/EtOH.

Examples 280–284, 287, 288, and 294 were synthesized following the above mentioned procedure for example 1 using the intermediate 4-bromo-7-methyltryptophol and reacting with β-ketoesters like ethyl 3-cyclobutyl-3-oxopropionate, ethyl 3-cyclopentyl-3-oxopropionate, ethyl 3-cyclopropyl-3-oxobutyrate, ethyl 4-cyclopentyl-3-oxobutyrate, ethyl 4-ethyl-3-oxohexanoate, methyl 4-methoxy-3-oxobutyrate, methyl 3-oxo-4-thiomethylbutyrate, or ethyl 6,6,6-trifluoro-3-oxohexanoate. The bromo substituent was converted to a cyano group using CuCN in N-methyl-2-pyrrolidinone as described in example 1. The resulting esters were hydrolyzed using aqueous NaOH in THF/EtOH.

EXAMPLE 285 AND EXAMPLE 286

(1R)-(5-Cyano-1-cyclobutyl-8-methyl-1,3,4,9-tetrahydropyrano[3,4-b]indol-1-yl)acetic acid (1S)-(5-Cyano-1-cyclobutyl-8-methyl-1,3,4,9-tetrahydropyrano[3,4-b]indol-1-yl)acetic acid Resolution of (±)-(5-Cyano-1-cyclobutyl-8-methyl-1,3,4,9-tetrahydropyrano[3,4-b]indol-1-yl)acetic acid Preparative HPLC using a CHIRALPAK-AS (250×20 mm) and 10% ethyl alcohol in heptane (0.1% TFA) as eluant gave (R)- and (S)-enantiomers of 1-cyclobutyl-5-cyano-8-methyl-1,3,4,9-tetrahydropyrano[3,4-b]indole-1-acetic acid as white solids. MS (API-ES) [M–] calculated for $C_{19}H_{20}N_2O_3$ 324.3, found 323.1 (R-enantiomer) and 323.1 (S-enantiomer); Chiral HPLC HP 1100 with CHIRALPAK-AS, 250×4.6 mm, ethyl alcohol/heptane containing 0.1% TFA (10:90), 0.6 mL/minutes, DAD 215 nm; tR=12.97 minutes (R-enantiomer), 15.46 minutes (S-enantiomer).

Examples 295 and 296 were synthesized following the above mentioned procedure for example 1 using the intermediate 4-bromo-7-ethyltryptophol and reacting with β-ketoesters like ethyl butyrylacetate, or ethyl 3-oxoheptanoate. The bromo substituent was converted to a cyano group using CuCN in N-methyl-2-pyrrolidinone as described in example 1. The resulting esters were hydrolyzed using aqueous NaOH in THF/EtOH.

Example 297 was synthesized following the above mentioned procedure for example 1 using the intermediate 4-bromo-7-isopropyltryptophol and reacting with β-ketoesters like ethyl butyrylacetate. The bromo substituent was converted to a cyano group using CuCN in N-methyl-2-pyrrolidinone as described in example 1. The resulting ester was hydrolyzed using aqueous NaOH in THF/EtOH.

Examples 298 and 299 were synthesized following the above mentioned procedure for example 1 using the intermediate 4-nitro-7-methyltryptophol and reacting with β-ketoesters like ethyl butyrylacetate, or ethyl 3-cyclobutyl-3-oxopropionate. The resulting esters were hydrolyzed using aqueous NaOH in THF/EtOH.

Examples 301–311 were synthesized following the above mentioned procedure for example 1 using the intermediate 4-bromo-7-fluorotryptophol and reacting with β-ketoesters like ethyl 3-cyclobutyl-3-oxopropionate, ethyl 3-cyclopentyl-3-oxopropionate, ethyl 4-cyclopropyl-3-oxobutyrate, ethyl 3-cyclohexyl-3-oxopropionate, ethyl 4-cyclopentyl-3-oxobutyrate, ethyl 4-ethyl-3-oxohexanoate, ethyl 3-oxo-6-butenoate, methyl 4-methoxy-3-oxobutyrate, 5-methoxy-3-oxopentanoate, methyl 3-oxo-4-thiomethylbutyrate, or ethyl 6,6,6-trifluoro-3-oxohexanoate. The bromo substituent was converted to a cyano group using CuCN in N-methyl-2-pyrrolidinone as described in example 1. The resulting esters were hydrolyzed using aqueous NaOH in THF/EtOH.

Example 317 was synthesized following the above mentioned procedure for example 1 using the intermediate 4-bromo-5-fluoro-7-methyltryptophol and reacting with β-ketoesters like ethyl 3-cyclobutyl-3-oxopropionate. The bromo substituent was converted to a cyano group using CuCN in N-methyl-2-pyrrolidinone as described in example 1. The resulting ester was hydrolyzed using aqueous NaOH in THF/EtOH.

Examples 321 and 327 were synthesized following the above mentioned procedure for example 1 using the intermediate 4-bromo-7-chlorotryptophol and reacting with β-ketoesters like ethyl butyrylacetate, or ethyl 3-cyclobutyl-3-oxopropionate. The bromo substituent was converted to a cyano group using CuCN in N-methyl-2-pyrrolidinone as described in example 1. The resulting esters were hydrolyzed using aqueous NaOH in THF/EtOH.

EXAMPLE 322 AND EXAMPLE 323

(1R)-(8-Chloro-5-cyano-1-propyl-1,3,4,9-tetrahydropyrano[3,4-b]indol-1-yl)acetic acid (1S)-(8-Chloro-5-cyano-1-propyl-1,3,4,9-tetrahydropyrano[3,4-b]indol-1-yl)acetic acid Resolution of (±)-(8-Chloro-5-cyano-1-propyl-1,3,4,9-tetrahydropyrano[3,4-b]indol-1-yl)acetic acid Preparative HPLC using a CHIRALPAK-AS (250×20 mm) and 10% isopropyl alcohol in heptane as eluant gave (R)- and (S)-enantiomers of 8-chloro-5-cyano-1-propyl-1,3,4,9-tetrahydropyrano[3,4-b]indole-1-acetic acid as white solids. MS (API-ES) [M–H]$^-$ calculated for $C_{17}H_{17}ClN_2O_3$ 332.7, found 330.9 (R-enantiomer) and 330.9 (S-enantiomer); Chiral HPLC HP 1100 with CHIRALPAK-AS, 250× 4.6 mm, isopropyl alcohol/heptane (10:90) containing 0.1% TFA, 0.6 mL/minutes, DAD 215 nm; tR=10.9 minutes (R-enantiomer), 12.22 minutes (S-enantiomer).

EXAMPLES 289 AND 290

(±)-(1R*,10S*)-5-Bromo-8-methyl-1-(1-methylpropyl)-1,3,4,9-tetrahydropyrano[3,4-b]indole-1-acetic acid Ethyl Ester and (±)-(1R*,10R*)-5-Bromo-8-methyl-1-(1-methylpropyl)-1,3,4,9-tetrahydropyrano[3,4-b]indole-1-acetic acid Ethyl Ester To a solution of 4-bromo-7-methyl tryptophol (2.04 g, 8.03 mmol) and (±)-ethyl 4-methyl-3-oxohexanate (1.52 g, 8.83 mmol) in $CH_2Cl_2$ (10 mL) was added $BF_3.OEt_2$ (1.12 mL, 8.83 mmol) dropwise at room temperature. The solution was stirred for 16 h then quenched by the addition of saturated aqueous $Na_2CO_3$ (2 mL). The reaction mixture was diluted with water and extracted three times with diethyl ether (150 mL). The combined organic layer was washed with brine then dried over anhydrous $Na_2SO_4$, filtered and concentrated to dryness. The crude product was purified by normal phase HPLC (isocratic, 5% EtOAc/hexane) to afford 1.4 g (43%) of esters as a mixture of 4 stereoisomers. Mass spectrum (APCI–): m/z 408 [M–].

(±)-(1R*,10S*)-5-Cyano-8-methyl-1-(1-methylpropyl)-1,3,4,9-tetrahydropyrano[3,4-b]indole-1-acetic acid ethyl ester and (±)-(1R*,10R*)-5-Cyano-8-methyl-1-(1-methylpropyl)-1,3,4,9-tetrahydropyrano[3,4-b]indole-1-acetic acid ethyl ester A mixture of (±)-(1R*,10S*)-5-bromo-8-methyl-1-(1-methylpropyl)-1,3,4,9-tetrahydropyrano[3,4-b]indole-1-acetic acid ethyl ester and (±)-(1R*,10R*)-5-bromo-8-methyl-1-(1-methylpropyl)-1,3,4,9-tetrahydropyrano[3,4-b]indole-1-acetic acid ethyl ester (1.4 g, 3.43 mmol) and CuCN (1.54 g, 17.1 mmol) was dissolved in N-methyl-2-pyrrolidinone (20 mL) and the solution was warmed to 160° C. After 5.5 h, the reaction was complete by TLC analysis and cooled to ambient temperature. The reaction mixture was diluted with water (25 mL) and extracted three times with diethyl ether (150 mL). The combined organic layer was washed once with brine, dried over anhydrous $Na_2SO_4$, filtered and concentrated. The crude product was purified by normal phase HPLC (isocratic, 5% EtOAc/hexanes) to afford a mixture of diastereomers. The two racemic diastereomers were separated by repeated normal phase HPLC (isocratic, 5% EtOAc/hexanes) combining only those fractions which contained diastereomer in >3:1 ratio. The enriched, separated diastereomers were resubjected to HPLC conditions (isocratic, 5% EtOAc/hexanes) until >10:1 diastereomeric ratio ($^1$H NMR analysis) was obtained. This material was used directly in the next step.

(±)-(1R*,10S*)-5-Cyano-8-methyl-1-(1-methylpropyl)-1,3,4,9-tetrahydropyrano[3,4-b]indole-1-acetic acid To a solution of (±)-(1R*,10S*)-5-cyano-8-methyl-1-(1-methylpropyl)-1,3,4,9-tetrahydropyrano[3,4-b]indole-1-acetic acid ethyl ester (0.04 g, 0.12 mmol) in EtOH (1 mL) was added 1.0 M LiOH (2 mL). The reaction mixture was stirred 16 h at ambient temperature. The reaction mixture was concentrated in vacuo and the residue was partitioned between water and diethyl ether. The mixture was acidified with dilute aqueous HCl and the layers were separated. The aqueous phase was extracted once with ether and the combined ether extracts were washed once with brine, dried over anhydrous $Na_2SO_4$, filtered and concentrated to afford 25 mg (68%) of (±)-(1R*,10S*)-5-cyano-8-methyl-1-(1-methylpropyl)-1,3,4,9-tetrahydropyrano[3,4-b]indole-1-acetic acid as a white solid. $^1$H NMR (CDCl$_3$, 300 MHz) δ 9.61 (br s, 1H), 7.34 (d, J=8 Hz, 1H), 6.97 (d, J=8 Hz, 1H), 4.28–4.09 (m, 2H), 3.82–3.73 (m, 1H), 3.17–2.98 (m, 3H), 2.55 (s, 3H), 2.23–2.15 (m, 1H), 1.29 (dt, J=7 Hz, J=2 Hz, 3H), 1.21–1.08 (m, 1H), 1.05 (d, J=7 Hz, 3H), 0.75 (d, J=7 Hz, 3H) ppm. Mass spectrum (API-ES): m/z 325 [M–H]$^-$.

(±)-(1R*,10R*)-5-Cyano-8-methyl-1-(1-methylpropyl)-1,3,4,9-tetrahydropyrano[3,4-b]indole-1-acetic acid To a solution of (±)-(1R*,10R*)-5-cyano-8-methyl-1-(1-methylpropyl)-1,3,4,9-tetrahydropyrano[3,4-b]indole-1-acetic acid ethyl ester (0.12 g, 0.36 mmol) in EtOH (1 mL) was added 1.0 M LiOH (2 mL). The reaction mixture was stirred 16 h at ambient temperature. The reaction mixture was concentrated in vacuo and the residue was partitioned between water and diethyl ether. The mixture was acidified with dilute aqueous HCl and the layers were separated. The aqueous phase was extracted once with ether and the combined ether extracts were washed once with brine, dried over anhydrous $Na_2SO_4$, filtered and concentrated to afford 110 mg (99%) of (±)-(1R*,10R*)-5-cyano-8-methyl-1-(1-methylpropyl)-1,3,4,9-tetrahydropyrano[3,4-b]indole-1-acetic acid as a white solid. $^1$H NMR (CDCl$_3$, 300 MHz) δ 9.08 (br s, 1H), 7.34 (d, J=8 Hz, 1H), 6.93 (d, J=8 Hz, 1H), 4.19 (dt, J=5 Hz, 1H), 3.96–3.87 (m, $^1$H), 3.17–3.10 (m, 4H), 2.41 (s, 3H), 2.27–2.17 (m, 1H), 1.74–1.64 (m, 1H), 1.39–1.26 (m, 1H), 0.95 (t, J=7 Hz, 3H), 0.78 (d, J=6 Hz, 3H) ppm. Mass spectrum (API-ES): m/z 325 [M–H]$^-$.

Examples 312 and 313 were synthesized following the above mentioned procedure for examples 289 and 290 using the intermediate 4-bromo-7-fluorotryptophol and reacting with (±)-ethyl 4-methyl-3-oxohexanate. The bromo substituent was converted to a cyano group using CuCN in N-methyl-2-pyrrolidinone as described in examples 289 and 290. The resulting esters were hydrolyzed using aqueous NaOH in THF/EtOH.

EXAMPLE 291

(1R*,10S)-[5-Bromo-8-methyl-1-(1-methylpropyl)-1,3,4,9 tetrahydropyrano[3,4-b]indol-1-yl]acetic acid ethyl ester To a solution of 4-bromo-7-methyl tryptophol (2.66 g, 10.4 mmol) and (S)-ethyl 4-methyl-3-oxohexanate (1.8 g, 10.4 mmol) in CH$_2$Cl$_2$ (50 mL) was added BF$_3$.OEt$_2$ (1.33 mL, 10.4 mmol) dropwise at room temperature. The solution was stirred for 48 h then quenched by the addition of saturated aqueous Na$_2$CO$_3$ (10 mL). The reaction mixture was diluted with water and extracted three times with diethyl ether (250 mL). The combined organic layer was washed with brine then dried over anhydrous Na$_2$SO$_4$, filtered and concentrated to dryness. The crude product was purified by normal phase HPLC (3% to 7% EtOAc/hexane, 70 minutes, 40 mL/minutes) to afford 1.85 g (43%) of esters as a mixture of 2 diastereomers. $^1$H NMR (CDCl$_3$, 300 MHz): ~1:1 mixture of 2 diastereomers, δ 9.32 (br s, 1H), 7.12 (d, J=7 Hz, 1H), 6.78 (d, J=7 Hz, 1H), 4.22–4.15 (m, 2H), 4.10–4.05 (m, 1H), 3.81–3.71 (m, 1H), 3.17–2.95 (m, 4H), 2.44 (s, 3H), 2.41–2.17 (m, 1H), 1.81–1.61 (m, 1H), 1.53–1.51 (m, 1H), 1.30–1.22 (m, 1H), 1.14–1.11 (m, 4H), 1.10–1.02 (m, 1H), 0.97–0.87 (m, 1H), 0.74 (t, J=7 Hz, 3H), 0.65 (d, j=7 Hz, 3H) ppm.

(1R*,10S)-[5-Cyano-8-methyl-1-(1-methylpropyl)-1,3,4,9-tetrahydropyrano[3,4-b]indol-1-yl]acetic acid Ethyl Ester A mixture of (1R,10S)-5-bromo-8-methyl-1-(1-methylpropyl)-1,3,4,9-tetrahydropyrano[3,4-b]indole-1-acetic acid ethyl ester and (1S,10S)-5-bromo-8-methyl-1-(1-methylpropyl)-1,3,4,9-tetrahydropyrano[3,4-b]indole-1-acetic acid ethyl ester (1.8 g, 4.41 mmol) and CuCN (1.98 g, 22.06 mmol) was dissolved in N-methyl-2-pyrrolidinone (20 mL) and the solution was warmed to 175° C. After 4 h, the reaction was complete by TLC analysis and cooled to ambient temperature. The reaction mixture was diluted with water (30 mL) and diethyl ether (30 mL) and filtered through a pad of celite. The filtrate was extracted three times with diethyl ether (150 mL). The combined organic layer was washed five times with water, once with brine, dried over anhydrous Na$_2$SO$_4$, filtered and concentrated. The crude product was purified by normal phase HPLC (3% to 7% EtOAc/hexane, 70 minutes, 40 mL/minutes) to afford 1.0 g (64%) of esters as a mixture of 2 diastereomers. $^1$H NMR (CDCl$_3$, 300 MHz): ~1:1 mixture of 2 diastereomers, δ 9.58 (br s, 1H), 7.34 (d, J=8 Hz, 1H), 6.97 (d, J=8 Hz, 1H), 4.27–4.09 (m, 3H), 3.82–3.73 (m, 1H), 3.17–2.84 (m, 4H), 2.55 (s, 3H), 2.51–2.14 (m, 1H), 1.72–1.64 (m, 1H), 1.40–1.23 (m, 1H), 1.28 (t, J=7 Hz, 3H), 1.21–1.10 (m, 1H), 1.05 (d, J=6 Hz, 1H), 0.94 (t, J=8 Hz, 3H), 0.75 (t, J=7 Hz, 3H), 0.65 (d, J=6 Hz, 1H) ppm.

(1R*,10S)-[5-Cyano-8-methyl-1-(1-methylpropyl)-1,3,4,9-tetrahydropyrano[3,4-b]indol-1-yl]acetic acid To a solution of (1R,10S)-5-cyano-8-methyl-1-(1-methylpropyl)-1,3,4,9-tetrahydropyrano[3,4-b]indole-1-acetic acid ethyl ester and (1S,10S)-5-cyano-8-methyl-1-(1-methylpropyl)-1,3,4,9-tetrahydropyrano[3,4-b]indole-1-acetic acid ethyl ester (0.95 g, 2.68 mmol) in EtOH (10 mL) was added 2.0 M LiOH (5 mL). After 2 h, an additional portion of 2.0 M LiOH (2 mL) was added. The reaction mixture was stirred 16 h at ambient temperature. The reaction mixture was concentrated in vacuo and the residue was partitioned between water (25 mL) and diethyl ether (25 mL). The mixture was acidified with dilute aqueous HCl and the layers were separated. The aqueous phase was extracted once with ether (15 mL) and the combined ether extracts were washed once with brine, dried over anhydrous Na$_2$SO$_4$, filtered and concentrated to afford 0.8 g (92%) of the mixture of 2 diastereomeric acids as a white solid. $^1$H NMR (CDCl$_3$, 300 MHz) δ 9.16–9.12 (m, 1H), 7.34 (d, J=8 Hz, 1H), 6.92 (d, J=8 Hz, 1H), 4.22–4.14 (m, 1H), 3.96–3.88 (m, 1H), 3.17–3.09 (m, 4H), 2.38 (s, 3H), 2.25–2.15 (m, 1H), 1.74–1.67 (m, 1H), 1.36–1.12 (m, 2H), 1.08 (d, J=7 Hz, 1H), 0.95 (t, J=8 Hz, 3H), 0.84–0.77 (m, 6H) ppm. Mass spectrum (API-ES$^+$): m/z 327 [M+H]$^+$.

Example 261 was synthesized following the above mentioned procedure for example 291 using the intermediate 4-chloro-7-methyltryptophol and reacting with (S)-ethyl 4-methyl-3-oxohexanate. The resulting esters were hydrolyzed using aqueous NaOH in THF/EtOH.

Example 279 was synthesized following the above mentioned procedure for example 291 using the intermediate 7-bromo-4-trifluoromethyltryptophol and reacting with (S)-ethyl 4-methyl-3-oxohexanate. The bromo substituent was converted to a cyano group using CuCN in N-methyl-2-pyrrolidinone as described in example 291. The resulting esters were hydrolyzed using aqueous NaOH in THF/EtOH.

Example 278 was formed as a by-product during the base-mediated saponification of the ester described in example 279.

Example 300 was synthesized following the above mentioned procedure for example 291 using the intermediate 7-methyl-4-nitrotryptophol and reacting with (S)-ethyl 4-methyl-3-oxohexanate. The resulting esters were hydrolyzed using aqueous NaOH in THF/EtOH.

Example 314 was synthesized following the above mentioned procedure for example 291 using the intermediate 4-bromo-7-fluorotryptophol and reacting with (S)-ethyl 4-methyl-3-oxohexanate. The bromo substituent was converted to a cyano group using CuCN in N-methyl-2-pyrrolidinone as described in example 291. The resulting esters were hydrolyzed using aqueous NaOH in THF/EtOH.

Example 318 was synthesized following the above mentioned procedure for example 291 using the intermediate 4-bromo-5-fluoro-7-methyltryptophol and reacting with (S)-ethyl 4-methyl-3-oxohexanate. The bromo substituent was converted to a cyano group using CuCN in N-methyl-2-pyrrolidinone as described in example 291. The resulting esters were hydrolyzed using aqueous NaOH in THF/EtOH.

Example 324 was synthesized following the above mentioned procedure for example 291 using the intermediate 4-bromo7-chlorotryptophol and reacting with (S)-ethyl 4-methyl-3-oxohexanate. The bromo substituent was converted to a cyano group using CuCN in N-methyl-2-pyrrolidinone as described in example 291. The resulting esters were hydrolyzed using aqueous NaOH in THF/EtOH.

EXAMPLE 292 AND EXAMPLE 293

(1R,10S)-[5-Cyano-8-methyl-1-(1-methylpropyl)-1,3,4,9-tetrahydropyrano[3,4-b]indol-1-yl]acetic acid (1S,10S)-[5-Cyano-8-methyl-1-(1-methylpropyl)-1,3,4,9-tetrahydropyrano[3,4-b]indol-1-yl]acetic acid Separation of (1R*,10S)-5-Cyano-8-methyl-1-(1-methylpropyl)-1,3,4,9-tetrahydropyrano[3,4-b]indole-1-acetic acid Preparative HPLC using a CHIRALPAK-AS (250×20 mm) and 10% isopropyl alcohol in heptane (0.1% TFA) as eluant gave the (1R, 10S)- and (1S,10S)-diastereomers of 5-cyano-8-methyl-1-(1-methylpropyl)-1,3,4,9-tetrahydropyrano[3,4-b]indole-1-acetic acid as white solids. MS (API-ES) [M−] calculated for $C_{19}H_{22}N_2O_3$ 326.4, found 325.1 {(1R,10S)-diastereomer, [M−H]$^-$} and 327.0 {(1S,10S)-diastereomer, [M+H]$^+$}; Chiral HPLC HP 1100 with CHIRALPAK-AS, 250×4.6 mm, isopropyl alcohol/heptane (10:90), 0.6 mL/minutes, DAD 215 nm; tR=8.12 minutes [(1R,10S)-diastereomer], 16.41 minutes [(1S,10S)-diastereomer].

EXAMPLE 315 AND 316

(1R,10S)-[5-Cyano-8-fluoro-1-(1-methylpropyl)-1,3,4,9-tetrahydropyrano[3,4-b]indol-1-yl]acetic acid (1S,10S)-[5-Cyano-8-fluoro-1-(1-methylpropyl)-1,3,4,9-tetrahydropyrano[3,4-b]indol-1-yl]acetic acid Separation of (1R*,10S)-5-Cyano-8-fluoro-1-(1-methylpropyl)-1,3,4,9-tetrahydropyrano[3,4-b]indole-1-acetic acid Preparative HPLC using a CHIRALPAK-AS (250×20 mm) and 10% isopropyl alcohol in heptane (0.1% TFA) as eluant gave the (1R,10S)- and (1S,10S)-diastereomers of 5-cyano-8-fluoro-1-(1-methylpropyl)-1,3,4,9-tetrahydropyrano[3,4-b]indole-1-acetic acid as white solids. MS (API-ES) [M−] calculated for $C_{18}H_{19}N_2O_3$ 330.3, found 329.2 {(1R,10S)-diastereomer, [M−H]$^-$} and 329.2 {(1S,10S)-diastereomer, [M−H]$^-$}; Chiral HPLC HP 1100 with CHIRALCEL OD, 250×4.6 mm, isopropyl alcohol/heptane (10:90) containing 0.1% TFA, 0.6 mL/minute, DAD 215 nm; tR=6.10 minutes [(1R,10S)-diastereomer], 7.20 minutes [(1S,10S)-diastereomer].

EXAMPLE 319 AND 320

(1R,10S)-[5-Cyano-6-fluoro-8-methyl-1-(1-methylpropyl)-1,3,4,9-tetrahydropyrano[3,4-b]indol-1-yl] acetic acid (1S,10S)-[5-Cyano-6-fluoro-8-methyl-1-(1-methylpropyl)-1,3,4,9-tetrahydropyrano[3,4-b]indol-1-yl] acetic acid Separation of (1R*,10S)-5-Cyano-6-fluoro-8-methyl-1-(1-methylpropyl)-1,3,4,9-tetrahydropyrano[3,4-b]indole-1-acetic acid Preparative HPLC using a CHIRALPAK-AS (250×20 mm) and 10% isopropyl alcohol in heptane as eluant gave the (1R,10S)- and (1S,10S)-diastereomers of 5-cyano-6-fluoro-8-methyl-1-(1-methylpropyl)-1,3,4,9-tetrahydropyrano[3,4-b]indole-1-acetic acid as white solids. MS (API-ES) [M−] calculated for $C_{19}H_{21}FN_2O_3$ 344.3, found 345.1 {(1R,10S)-diastereomer, [M+H]$^+$} and 342.9 {(1S,10S)-diastereomer, [M−H]$^-$}; Chiral HPLC HP 1100 with CHIRALPAK-AS, 250×4.6 mm, isopropyl alcohol/heptane (10:90), 0.6 mL/minute, DAD 215 nm; tR=20.21 minutes [(1R,10S)-diastereomer], 9.28 minutes [(1S,10S)-diastereomer].

EXAMPLE 325 AND 326

(1R,10S)-[8-Chloro-5-cyano-1-(1-methylpropyl)-1,3,4,9-tetrahydropyrano[3,4-b]indol-1yl]acetic acid (1S,10S)-[8-Chloro-5-cyano-1-(1-methylpropyl)-1,3,4,9-tetrahydropyrano[3,4-b]indol-1-yl]acetic acid Separation of (1R*,10S)-8-Chloro-5-cyano-1-(1-methylpropyl)-1,3,4,9-tetrahydropyrano[3,4-b]indole-1-acetic acid Preparative HPLC using a CHIRALPAK-AS (250×20 mm) and 10% isopropyl alcohol in heptane containing 0.1% TFA as eluant gave the (1R,10S)- and (1S,10S)-diastereomers of 8-chloro-5-cyano-1-(1-methylpropyl)-1,3,4,9-tetrahydropyrano[3,4-b]indole-1-acetic acid as white solids. MS (API-ES) [M−] calculated for $C_{18}H_{19}ClN_2O_3$ 346.8, found 345.0 {(1R,10S)-diastereomer, [M−H]$^-$]} and 345.0 {(1S,10S)-diastereomer, [M−H]$^-$}; Chiral HPLC HP 1100 with CHIRALPAK-AS, 250×4.6 mm, isopropyl alcohol/heptane (10:90) containing 0.1% TFA, 0.6 mL/minutes, DAD 215 nm; tR=7.24 minutes [(1R,10S)-diastereomer], 9.89 minutes [(1S,10S)-diastereomer].

Example 328 was synthesized following the above mentioned procedure for example 1 using the intermediate 4,5-dichlorotryptophol and reacting with α-ketoesters like ethyl-2-oxopentanoate. The resulting ester was hydrolyzed using aqueous NaOH in THF/EtOH.

Example 329 was synthesized following the above mentioned procedure for example 1 using the intermediate 4,7-dichlorotryptophol and reacting with α-ketoesters like ethyl-2-oxopentanoate. The resulting ester was hydrolyzed using aqueous NaOH in THF/EtOH.

Example 330 was synthesized following the above mentioned procedure for example 1 using the intermediate 4-chloro-7-methyltryptophol and reacting with α-ketoesters like ethyl-2oxopentanoate. The resulting ester was hydrolyzed using aqueous NaOH in THF/EtOH.

Example 331 was synthesized following the above mentioned procedure for example 1 using the intermediate 7-chloro-4-trifluoromethyltryptophol and reacting with a-ketoesters like ethyl-2-oxopentanoate. The resulting ester was hydrolyzed using aqueous NaOH in THF/EtOH.

Example 332 was synthesized following the above mentioned procedure for example 1 using the intermediate 7-fluoro-4-trifluoromethyltryptophol and reacting with α-ketoesters like ethyl-2-oxopentanoate. The resulting ester was hydrolyzed using aqueous NaOH in THF/EtOH.

Example 333 was synthesized following the above mentioned procedure for example 1 using the intermediate 7-methyl-4-trifluoromethyltryptophol and reacting with α-ketoesters like ethyl-2-oxopentanoate. The resulting ester was hydrolyzed using aqueous NaOH in THF/EtOH.

Examples 334, 337, and 338 were synthesized following the above mentioned procedure for example 1 using the intermediate 4-bromo-7-methyltryptophol and reacting with α-ketoesters like ethyl-2-oxopentanoate, methyl 4-methyl-2-oxopentanoate, methyl 2-cyclobutyl-2-oxoacetate. The bromo substituent was converted to a cyano group using CuCN in N-methyl-2-pyrrolidinone as described in example 1. The resulting ester was hydrolyzed using aqueous NaOH in THF/EtOH.

Examples 335 and 336 were synthesized following the above mentioned procedure for example 291 using the intermediate 4-bromo-7-methyltryptophol and reacting with (S)-methyl 3-methyl-2-oxopentanoate. The resulting esters were separated by normal phase HPLC and the hydrolyzed using aqueous NaOH in THF/EtOH.

Example 339 was synthesized following the above mentioned procedure for example 1 using the intermediate 4-bromo-5-fluoro-7-methyltryptophol and reacting with α-ketoesters like ethyl-2-oxopentanoate. The bromo substituent was converted to a cyano group using CuCN in N-methyl-2-pyrrolidinone as described in example 1. The resulting ester was hydrolyzed using aqueous NaOH in THF/EtOH.

Example 340 was synthesized following the above mentioned procedure for example 1 using the intermediate 4-bromo-7-ethyltryptophol and reacting with α-ketoesters like ethyl-2-oxopentanoate. The bromo substituent was converted to a cyano group using CuCN in N-methyl-2-pyrrolidinone as described in example 1. The resulting ester was hydrolyzed using aqueous NaOH in THF/EtOH.

Example 341 was synthesized following the above mentioned procedure for example 1 using the intermediate 4-bromo-7-chlorotryptophol and reacting with α-ketoesters like ethyl-2-oxopentanoate. The bromo substituent was converted to a cyano group using CuCN in N-methyl-2-pyrrolidinone as described in example 1. The resulting ester was hydrolyzed using aqueous NaOH in THF/EtOH.

Example 342 was synthesized following the above mentioned procedure for example 1 using the intermediate 4-bromo-7-fluorotryptophol and reacting with α-ketoesters like ethyl-2-oxopentanoate. The bromo substituent was converted to a cyano group using CuCN in N-methyl-2-pyrrolidinone as described in example 1. The resulting ester was hydrolyzed using aqueous NaOH in THF/EtOH.

EXAMPLE 343 AND EXAMPLE 344

Resolution of (±)-(5-Cyano-8-fluoro-1-propyl-1,3,4,9-tetrahydropyrano[3,4-b]indol-1-yl)carboxylic acid Preparative HPLC using a CHIRALPAK-AS (250×20 mm) and 10% ethyl alcohol in heptane (0.1% TFA) as eluant gave (R)- and (S)-enantiomers of 5-cyano-8-fluoro-1-propyl-1,3,4,9-tetrahydropyrano[3,4-b]indole-1-carboxylic acid as white solids. MS (API-ES) [M−] calculated for $C_{16}H_{15}FN_2O_3$ 302.3, found 301.1 (R-enantiomer) and 301.0 (S-enantiomer); Chiral HPLC HP 1100 with CHIRALPAK-AS, 250×4.6 mm, ethyl alcohol/heptane containing 0.1% TFA (10:90), 0.6 mL/minute, DAD 215 nm; tR=7.07 minutes (R-enantiomer), 10.5 minutes (S-enantiomer).

Examples 345–347, 350, and 351 were synthesized following the above mentioned procedure for example 1 using the intermediate 4-bromo-7-fluorotryotophol and reacting with α-ketoesters like methyl 2-oxohexanoate, methyl 2-oxohex-5-enoate, methyl 4-methyl-2-oxopentanoate, methyl 2-cyclopentyl-2-oxoacetate, and methyl 2-cyclohexyl-2-oxoacetate. The bromo substituent was converted to a cyano group using CuCN in N-methyl-2-pyrrolidinone as described in example 1. The resulting esters were hydrolyzed using aqueous NaOH in THF/EtOH.

Examples 348 and 349 were synthesized following the above mentioned procedure for example 291 using the intermediate 4-bromo-7-methyltryptophol and reacting with (S)-methyl 3-methyl-2-oxopentanoate. The resulting esters were separated by normal phase HPLC and the esters were hydrolyzed using aqueous NaOH in THF/EtOH.

Example 352 was synthesized following the above mentioned procedure for example 291 using the intermediate 7-methyl-4-nitrotryptophol and reacting with ethyl-2-oxopentanoate. The resulting ester was separated by normal phase HPLC and the hydrolyzed using aqueous NaOH in THF/EtOH.

EXAMPLE 353

1-Carboxymethyl-5-cyano-8-methyl-1-propyl-1,3,4,9-tetrahydro-pyrano[3,4-b]indole-7-carboxylic acid 5-Bromo-2-methyl-3-nitrobenzoic acid A 5000 mL, three neck round bottom flask (RBF) equipped with an overhead stirrer was charged with 2-methyl-3-nitro benzoic acid (150.0 g, 0.82 mol) and concentrated $H_2SO_4$ (600 mL). To this solution was added 1,3-dibromo-5,5 dimethylhydantoin (130.7 g, 0.455 mol) over ten minutes with vigorous stirring. The reaction was vigorously stirred at ambient temperature for 5 hours. The reaction mixture was then added to water (4000 mL), and the mixture was cooled in an ice bath over 30 minutes. This mixture was then filtered, and the solids were washed twice with water and further dried under vacuum to yield 217.7 g (99.8%) of an off-white solid. $^1$H NMR (CDCl$_3$) δ 8.18 (s, 1H), 7.95 (s, 1H), 2.59 (s, 3H).

5-bromo-2-methyl-3-nitrobenzole acid benzyl ester

A 5000 mL three neck RBF equipped with an overhead stirrer and thermometer was charged with 5-bromo-2-methyl-3-nitro benzoic acid (116.2 g, 0.45 mol), THF (1 L), and benzyl bromide (BnBr) (84.90 mL, 0.715 mol). To the stirring solution was added diisopropyl ethylamine (DIEA)

(78 mL, 0.450 mol). The reaction was then brought to reflux. After 5.5 hours at reflux, the reaction was cooled to 40° C., and pyrrolidine (83 mL, 1.00 mol) was added. The reaction was stirred for 10 minutes at 40° C., then allowed to cool to ambient temperature over approximately 20 minutes. The reaction mixture was diluted with EtOAc and washed with 3% HCl (2×), water (1×), and saturated NaCl (1×), dried (MgSO4), and concentrated. The brown oil was taken up in DCM and slurried with approximately 300 g of silica gel. The slurry was filtered, solids were washed with EtOAc, and the filtrate was concentrated to afford a yellow oil. Upon trituration with hexanes, 244.9 g (83.8%) of an off white powder was obtained. 1H NMR (CDCl3) δ 8.10 (s, 1H), 7.96 (s, 1H), 7.41 (m, 5H), 5.37 (s, 2H), 2.55 (s, 3H).

3-Amino-5-bromo-2-methylbenzoic acid benzyl ester

A 1000 mL RBF equipped with an overhead stirrer was charged with 5-bromo-2-methyl-3-nitro benzoic acid benzyl ester (75.0 g, 0.214 mol) and water (200 mL). While stirring vigorously, Fe powder (–325 mesh, 47.81 g, 0.857 mol) and $NH_4Cl$ (13.88 g, 0.257 mol) were added. The mixture was heated to reflux for 4.5 hours. The reaction mixture was then allowed to cool to room temperature, diluted with EtOAc and filtered through a pad of Celite. The filtrate was washed with water (2×), saturated NaCl (1×), dried ($MgSO_4$), and concentrated. Upon trituration with hexanes, 63.2 g (92.1%) of an off-white powder was obtained. $^1H$ NMR ($CDCl_3$) δ 7.38 (m, 6H), 6.90 (s, 1H), 5.31 (s, 2H), 3.76 (br s, 2H), 2.25 (s, 3H).

5-Bromo-3-hydrazino-2-methyl benzoic acid benzyl ester hydrochloride

A 1000 mL three neck RBF equipped with an overhead stirrer was charged with 3-amino-5-bromo-2-methyl benzoic acid benzyl ester (25.0 g, 0.078 mol), water (150 mL), and concentrated HCl (150 mL). This mixture was stirred vigorously while cooling to –10° C. in a MeOH/ice bath. A solution of $NaNO_2$ (8.08 g, 0.120 mol) in water (150 mL) was cooled to –10° C. and then added to the reaction mixture dropwise over 15 minutes. The reaction was vigorously stirred at –10° C. for 1.5 hours, then a solution of $SnCl_2.2H_2O$ (73.99 g, 0.330 mol) at –10° C. in concentrated HCl (150 mL) was added to the reaction mixture dropwise over 20 minutes. The resulting mixture was allowed to react for 1.5 hours at –10° C. with very vigorous stirring. The reaction mixture was then added to 6N NaOH (600 mL) and extracted with EtOAc. The organic layer was separated and washed with saturated NaCl (1×), dried over $MgSO_4$, and concentrated. The yellow solid was taken up in THF (100 mL), and 4N HCl (30 mL) in dioxane was added. The solvents were removed under vacuum. Trituration with DCM/hexanes yielded 27.1 g (93.5%) of a white powder. $^1H$ NMR ($d_6$-DMSO) δ 10.47(br s, 2H), 8.39 (br s, 1H), 7.40 (m, 7H), 5.33 (s, 2H), 2.26 (s, 3H).

4-Bromo-3-(2-hydroxy-ethyl)-7-methyl-1H-indole-6-carboxylic acid benzyl ester

A 1000 mL RBF was charged with 5-bromo-3-hydrazino-2-methyl benzoic acid benzyl ester hydrochloride (30.0 g, 0.081 mol), ethylene glycol (350 mL), and water (60 mL). This mixture was heated to 40° C., and dihydrofuran (7.63 mL, 0.101 mol) was added. The reaction mixture was next heated to 100–105° C. with stirring for 2.25 hours. The reaction was then cooled to ambient temperature, diluted with EtOAc, washed with saturated NaCl (2×), dried ($MgSO_4$), and concentrated. The resulting oil was chromatographed on $SiO_2$, eluting with a 10% EtOAc/DCM to 50% EtOAc/DCM gradient. Isolation of the product as an impure solid, followed by trituration with DCM and hexanes, afforded 8.45 g (27.0%) of a pale yellow solid. $^1H$ NMR ($CDCl_3$) δ 8.28 (br s, 1 H), 7.94 (s, 1H), 7.40 (m, 6H), 5.36 (s, 2H), 3.96 (q, J=6.4 Hz, 2H), 3.28 (t, J=6.4 Hz, 2H), 2.72 (s, 3H).

5-Bromo-1-ethoxycarbonylmethyl-8-methyl-1-propyl-1,3,4,9-tetrahydro-pyrano[3,4-b]indole-7-carboxy acid benzyl ester A 1000 mL RBF was charged with of 4-bromo-3-(2-hydroxy-ethyl)-7-methyl-1H-indole-6-carboxylic acid benzyl ester (12,03 g, 0.031 mol), ethyl butyrylacetate (5.45 mL, 0.034 mol), and DCM (500 mL). This mixture was cooled to 0° C. with stirring. Over approximately 5 minutes, $BF_3.Et_2O$ (9.82 mL, 0.078 mol) was added to the stirring mixture. The reaction was allowed to warm to ambient temperature and was stirred for 1 hour. The mixture was then diluted with EtOAc, washed with saturated $NaHCLO_3$ (2×) and saturated NaCl (1×), dried ($MgSO_4$), and concentrated. The resulting oil was purified by flash chromatography on $SiO_2$ eluting with a 10% EtOAc/hexanes to 20% EtOAc/hexanes gradient. Trituration with hexanes yielded 13.71 g (84.0%) of a white powder. $^1H$ NMR ($CDCl_3$) δ 9.81 (br s, 1H), 7.89 (s, 1H), 7.40 (m, 5H), 5.35 (s, 2H), 4.21 (m, 2H), 3.95 (m, 2H), 3.15 (t, J=4.7 Hz, 2H), 3.03 (d, J=16.7 Hz, 1H), 2.91 (d, J=16.7 Hz, 1H), 2.73 (s, 3H), 2.00 (m, 2H), 1.29 (m, 5H), 0.88 (t, J=7.6 Hz, 3H).

5-Cyano-1-ethoxycarbonylmethyl-8-methyl-1-propyl-1,3,4,9-tetrahydro-pyrano[3,4-b]indole-7-carboxylic acid benzyl ester A 500 mL RBF was charged with 5-bromo-1-ethoxycarbonylmethyl-8-methyl-1-propyl-1,3,4,9-tetrahydro-pyrano[3,4-b]indole-7-carboxylic acid benzyl ester (12.00 g, 23 mmol), NMP (100 mL), and CuCN (20.34 g, 0.227 mol). The reaction was heated to 190° C. with vigorous stirring for 45 minutes. The reaction was then cooled to ambient temperature, diluted with EtOAc followed by water (300 mL). A 1:1 mixture of Celite/silica gel were added to the mixture. This suspension was stirred for several minutes and filtered through a pad of Celite. The Celite pad was washed with EtOAc, and the filtrate was washed with water (5×) and saturated NaCl (1×), dried over $MgSO_4$, and concentrated. Upon trituration with hexanes, 8.82 g (81.8%) of a light tan solid was obtained. $^1H$ NMR ($CDCl_3$) δ 10.11 (br s, 1H), 8.12 (s, 1H), 7.40 (m, 5H), 5.37 (s, 2H), 4.22 (m, 2H), 3.95 (m, 2H), 3.00 (m, 4H), 2.83 (s, 3H), 2.00 (m, 2H), 1.30 (m, 5H), 0.89 (t, J=7.6 Hz, 3H).

5-Cyano-1-ethoxycarbonylmethyl-8-methyl-1-propyl-1,3,4,9-tetrahydro-pyrano[3,4-b]indole-7-carboxylic acid A 500 mL Parr flask was charged with 5-cyano-1-ethoxycarbonylmethyl-8-methyl-1-propyl-1,3,4,9-tetrahydro-pyrano[3,4-b]indole-7-carboxylic acid benzyl ester (14.24 g, 0.030 mol), 1:1 MeOH/EtOAc (180 mL), and $Pd(OH)_2$ (20% on C, 3.02 g). The flask was shaken on a Parr shaker at 5 psi above ambient pressure for 30 minutes. The reaction mixture was filtered through a pad of Celite, washed with methanol and concentrated. Trituration with hexanes yielded 11.11 g (96.4%) of an off-white powder. $^1H$ NMR ($CDCl_3$) δ 10.21 (br s, 1H), 8.22 (s, 1H), 4.22 (m, 2H), 4.00 (m, 2H), 3.09 (m, 4H), 2.89 (s, 3H), 2.00 (m, 2H), 1.30 (m, 5H), 0.90 (t, J=7.6 Hz, 3H).

1-Carboxymethyl-5-cyano-8-methyl-1-propyl-1,3,4, 9-tetrahydro-pyrano[3,4-b]indole-7-carboxylic acid To a solution of 5-Cyano-1-ethoxycarbonylmethyl-8-methyl-1-propyl-1,3,4,9-tetrahydro-pyrano[3,4-b]indole-7-carboxylic acid (27.9 mg, 0.073 mmol) in EtOH (2 mL) was added 10% NaOH (200 μL). The solution was stirred for 18 hours, acidified with 3% HCl, and extracted with EtOAc (2×). The organic layers were combined, washed with brine, dried (Na$_2$SO$_4$) and concentrated in vacuo to afford 25.6 mg (99%) of the title compound as an off-white solid. $^1$H NMR (d$_6$-DMSO) δ 11.42 (br s,1 H), 7.93 (s, 1H), 3.97 (m, 2H), 3.00 (d, J=13.8 Hz, 1H), 2.88 (m, 2H), 2.81 (s, 3H), 2.76 (d, J=13.8 Hz, 1H), 2.04 (m, 2H), 1.30 (m,1H), 0.80 (m, 4H). ESI MS m/z 355 (M–H).

EXAMPLE 354

(5-Cyano-8-methyl-1-propyl-7-propylcarbamoyl-1,3, 4,9-tetrahydro-pyrano[3,4-b]indol-1-yl)-acetic acid To a solution of 5-cyano-1-ethoxycarbonylmethyl-8-methyl-1-propyl-1,3,4,9-tetrahydro-pyrano[3,4-b]indole-7-carboxylic acid (36.3 mg, 0.09 mmol) in methylene chloride (2 mL) was added N-methylmorpholine (NMM) (31 μL, 0.2 mmol), propylamine (15 μL, 0.19 mmol), and O-(7-Azabenzotriazol-1-yl)-N,N,N',N'-tetramethyluronium hexafluorophosphate (HATU) (54 mg, 0.14 mmol). After 21 hours, the solution was diluted with EtOAc, and then water was added. The layers were separated, and the organic layer was washed with 3% HCL (2×), 5% NaHCO$_3$ (2×), water (1×), and brine (1×), dried (Na$_2$SO$_4$), and concentrated in vacuo to afford 37.1 mg (92%) of crude product which was carried on to the next step.

EtOH (2 mL) and 10% NaOH (aq, 125 μL) were added to the crude propylamide. The solution was stirred for 16 hours, acidified with 3% HCl, and extracted with DCM. The organic layer was washed with water and brine, dried (Na2SO4) and concentrated in vacuo to afford 30.3 mg (88%) of the title compound as a pale yellow solid. 1H NMR (CDCl3) δ 10.10 (br s, 1H), 7.40 (s, 1H), 6.11 (t, J=5.9 Hz, 1H), 4.04 (m, 1H), 3.92 (m, 1H), 3.44 (m, 2H), 3.05 (t, J=5.6 Hz, 2H), 2.97 (br s, 2H), 2.53 (s, 3H), 2.0 (m, 2H), 1.68 (m, 2H), 1.43 (m, 1H), 1.20 (m,1H), 1.03 (m, 3H), 0.87 (t, J=7.3 Hz, 3H). ESI MS m/z 398 (MH)+.

Examples 355–358 were synthesized following the above mentioned procedure for example 354 using the intermediate 5-cyano-1-ethoxycarbonylmethyl-8-methyl-1-propyl-1, 3,4,9-tetrahydro-pyrano[3,4-b]indole-7-carboxylic acid and coupling it with the following amines: isopropylamine, 3,3-dimethylbutylamine, methylamine, and dimethylamine. The resulting esters were hydrolyzed using 10% NaOH (aq) in EtOH. In most instances the final products required no chromatographic purification.

EXAMPLE 359

(5-Cyano-8-methyl-7-propoxy-1-propyl-1,3,4,9-tetrahydro-pyrano[3,4-b]indol-1-yl)acetic acid (5-Cyano-7-hydroxymethyl-8-methyl-1-propyl-1,3, 4,9-tetrahydro-pyrano!3,4-b]indol-1-yl)-acetic acid ethyl ester To a solution of 5-cyano-1-ethoxycarbonylmethyl-8-methyl-1-propyl-1,3,4,9-tetrahydro-pyrano[3,4-b]indole-7carboxylic acid (11.1 g, 29.0 mmol) in THF (150 mL) at 0° C. was added BH$_3$.THF (1.0M in THF, 72.2 mL, 72.2 mmol). The cooling bath was removed, and the solution was stirred for 1.5 hours. The reaction was quenched with 3% HCl, diluted with EtOAc, and the layers separated. The organic layer was washed with saturated NaHCO$_3$, water and brine, dried (MgSO$_4$), and concentrated in vacuo. Purification via flash chromatography on SiO$_2$ using 20% EtOAc/DCM as eluent afforded 8.28 g (77%) of a pale green foam. ESI-MS m/z 369 (M–H)$^-$. $^1$HNMR (CDCl$_3$) δ 9.72 (bs, 1H), 7.43 (s, 1H), 4.80 (d, J=5.5, 2H), 4.25 (m, 2H), 4.15 (m, 1H), 3.93 (m, 1H), 3.02 (m, 3H), 2.92 (d, J=17.0 Hz, 1H), 2.57 (s, 3H), 2.00 (m, 2H), 1.30 (m, 5H), 0.88 (t, J=7.6 Hz, 3H).

(5-Cyano-7-formyl-8-methyl-1-propyl-1,3,4,9-tetrahydro-pyrano[3,4-b]indol-1-yl)-acetic acid ethyl ester To a solution of (5-cyano-7-hydroxymethyl-8-methyl-1-propyl-1,3,4,9-tetrahydro-pyrano[3,4-b]indol-1-yl)-acetic acid (8.28 g, 22 mmol) in dichloroethane/benzene (85 mL/85 mL) was added a homogeneous mixture of activated MnO$_2$ (19.4 g, 223 mmol) and Celite (19.4 g). The solution was heated to 40° C. and agitated vigorously for 1.3 hours. The reaction was cooled, diluted with EtOAc and filtered through Celite. Concentration of the filtrate in vacuo afforded 7.88 g (96%) of a pale yellow foam. $^1$H NMR (CDCl$_3$) δ 10.31 (bs, 1 H), 10.27 (s, 1H), 7.90 (s, 1H), 4.27 (m, 2H), 4.11 (m, 1H), 3.95 (m, 1H), 3.09 (m, 2H), 3.04 (d, J=17.0 Hz, 1H), 2.95 (d, J=7.6 Hz, 1H), 2.57 (s, 3H), 2.00 (m, 2H), 1.30 (m, 4H), 0.90 (t, J=7.62 Hz, 2H).

(5-Cyano-7-hydroxy-8-methyl-7-propyl-1,3,4,9-tetrahydro-pyrano[3,4-b]indol-1-yl)-acetic acid ethyl ester To a solution of (5-cyano-7-formyl-8-methyl-1-propyl-1, 3,4,9-tetrahydropyrano[3,4-b]indol-1-yl]-acetic acid (7.88 g, 21 mmol) in tert-butanol (150 mL) was added SeO$_2$ (0.90 g, 6.4 mmol) followed by 30% H$_2$O$_2$ (75 mL) and trifluoroacetic acid (0.23 mL). The solution was stirred at ambient temperature for 1 hour. The reaction was diluted with EtOAc, washed with saturated NaHCO$_3$ (2×), water and brine, dried (MgSO$_4$), and concentrated in vacuo to afford a brown foam. ESI-MS m/z 383 (M–H)–, $^1$H NMR CDCl$_3$ (300 MHz) δ 9.86 (bs, 1H), 8.35 (s, 1H), 7.16 (s, 1H), 4.20 (m, 2H), 4.00 (m, 2H), 3.01 (m, 4H), 2.57 (s, 3H), 2.00 (m, 2H), 1.30 (m, 5H), 0.89 (t, J=7.6 Hz, 3H).

The residue was dissolved in MeOH (145 mL), and to this was added 10% K$_2$CO$_3$ (aq., 14.5 mL). After stirring for 30 minutes, the reaction was diluted with EtOAc, washed with water (2×) and brine, dried (MgSO$_4$) and concentrated in vacuo. Trituration with DCM/hexane afforded 5.59 g (73%) of the title compound as an off-white solid. ESI-MS m/z 355 (M–H). $^1$HNMR (CD$_3$OD) δ 6.90 (s,1H), 4.01 (m, 4H), 3.03 (d, J=13.5 Hz, 1H), 2.91 (m, 2H), 2.82 (d, J=13.5 Hz, 1H), 2.39 (s, 3H), 2.00 (m, 2H), 1.42 (m, 1H), 1.06 (m, 4H), 0.87 (t, J=7.0 Hz, 3H).

(5-Cyano-8-methyl-7-propoxy-1-propyl-1,3,4,9-tetrahydro-pyrano[3,4-b]indol-1-yl)-acetic acid To a solution of (5-cyano-7-hydroxy-8-methyl-1-propyl-1,3,4,9-tetrahydro-pyrano[3,4-b]indol-1-yl)-acetic acid ethyl ester (41.5 mg, 0.12 mmol) in dry THF (2 mL) was added triphenyl phosphine (52.2 mg, 0.20 mmol) and n-propanol (14.7 μL, 0.20 mmol). To this solution was added diisopropylazodicarboxylate (DIAD, 39 μL, 0.20 mmol). After 20 minutes, additional portions of triphenyl phosphine (5 mg) and DIAD (5 μL) were added. The reaction mixture was stirred for 10 minutes and quenched with water. The mixture was diluted with EtOAc, and the layers were separated. The organic layer was washed with water and brine, dried (Na$_2$SO$_4$), and concentrated in vacuo. Flash chromatography on SiO$_2$ using 5% EtOAc/hexanes as eluent afforded 30.9 mg (67%) of the ester intermediate as a white solid.

To the ester intermediate was added EtOH (2 mL) and 10% NaOH (aq., 150 μL). The solution was stirred for 20 hours, acidified with 3% HCl, and extracted with EtOAc. The organic layer was washed with water and brine, dried (Na$_2$SO$_4$), and concentrated in vacuo to afford 28.9 mg (quant.) of the title compound as a white solid. ESI-MS m/z 371 (MH)$^+$. $^1$H NMR (d$_6$-DMSO) δ 11.95 (br s, 1H), 10.85 (s, 1H), 7.18 (s, 1H), 3.96 (m, 4H), 2.93 (d, J=13.9 Hz, 1H), 2.82 (m, 2H), 2.71 (d, J=13.9 Hz, 1H), 2.38 (s, 3H), 1.98 (m, 2H), 1.74 (m, 2H), 1.25 (m, 1H), 1.01 (t, J=7.3 Hz, 3H), 0.85 (m, 4H).

EXAMPLE 360 AND 361

(1R)-(5-cyano-8-methyl-7-propoxy-1-propyl-1,3,4,9-tetrahydro-pyrano[3,4-b]indol-1-yl)-acetic acid (1S)-(5-Cyano-8-methyl-7-propoxy-1-propyl-1,3,4,9-tetrahydro-pyrano[3,4-b]indol-1-yl)-acetic acid Preparative HPLC using CHIRALPAK AS (250×20mm) and 5% ethanol in hexane as eluant gave the (R) and (S) enantiomers of (5-cyano-8-methyl-7-propoxy-1-propyl-1,3,4,9-tetrahydro-pyrano[3,4-b]indol-1-yl)-acetic acid as white solids. ESI-MS m/z 371 (MH$^+$, R isomer) and m/z 371 (MH$^+$, S isomer). Chiral HPLC HP 100 with CHIRALPAK AS, 250×4.6 mm, ethanol/hexane (7/93), 1.0 mL/min, 235 nm UV detection; tR=8.46 min (R enantiomer), 13.42 min (broad peak, S enantiomer).

Examples 362–368 were synthesized following the above mentioned procedure for example 359 using the intermediate (5-cyano-7-hydroxy-8-methyl-1-propyl-1,3,4,9-tetrahydro-pyrano[3,4-b]indol-1-yl)-acetic acid ethyl ester and coupling it with the following alcohols: ethanol, methanol, isopropanol, n-butyl alcohol, 3,3-dimethyl-1-butanol, 3-fluorobenzyl alcohol, and benzyl alcohol. The resulting esters were hydrolyzed using 10% NaOH (aq) in EtOH.

EXAMPLE 369

[5-Cyano-7-(2-fluoro-ethoxy)-8-methyl-1-propyl-1,3,4,9-tetrahydro-pyrano[3,4-b]indol-1-yl]-acetic acid To a solution of (R)-[5-cyano-7-hydroxy-8-methyl-1-propyl-1,3,4,9-tetrahydro-pyrano[3,4]indol-1-yl-]-acetic acid methyl ester (35 mg, 0.10 mmol) in anhydrous dichloromethane (1 mL) was added 2-fluoroethanol (40 mg, 0.62 mmol), 1,1'-(azodicarbonyl)dipiperidine (39 mg, 0.15 mmol), and triphenylphosphine (40 mg, 0.15 mmol) at ambient temperature. After 48 h, the reaction mixture was absorbed onto silica gel and the product was eluted with hexane/EtOAc (4:1). The ester was used directly in the next reaction.

The crude ester was dissolved in EtOH (2 mL) and THF (1 mL). At ambient temperature, 3 N NaOH (2 mL) was added and the reaction mixture was stirred for 3 h. The reaction mixture was then acidified with 1 M HCl and the aqueous solution was extracted with ethyl ether. The organic phase was washed once with 1 M HCl, once with brine, dried over anhydrous Na$_2$SO$_4$, filtered and concentrated. The crude acid was triturated with ethyl ether/hexanes and the solid was collected on a Hirsch funnel and washed several times with hexane to afford 21 mg of the title compound as an off-white solid. ESI-MS m/z 373 (M–H)$^-$. $^1$H NMR (CDCl$_3$) δ 8.99 (br s, 1H), 6.99 (s, 1H), 4.77 (dt, J=47.4, 3.5 Hz, 2 H), 4.03–4.27 (m, 4H), 3.12 (m, 4H), 2.15 (s, 3H), 1.89–2.11 (m, 4H), 1.19–1.61 (m, 2H), 0.91 (t, J=7.0 Hz, 3H) ppm.

EXAMPLE 370

[5-Cyano-7-(3-fluoro-propoxy)-8-methyl-1-propyl-1,3,4,9-tetrahydro-pyrano[3,4-b]indol-1-yl]-acetic acid To a solution of (R)-[5-cyano-7-hydroxy-8-methyl-1-propyl-1,3,4,9-tetrahydropyrano[[3,4-b]indol-1-yl]-acetic acid methyl ester (32 mg, 0.09 mmol) in anhydrous N-methyl-2-pyrrolidinone (2 mL) was added Cs$_2$CO$_3$ (76 mg, 0.23 mmol), KI (2 mg, 10 mol %), and 1-bromo-3-fluoropropane (26 mg, 0.18 mmol) at ambient temperature. After 6 h, the reaction mixture was diluted with water (50 mL) and ethyl ether (50 mL). Aqueous HCl (1 M) was added and the layers were separated. The organic phase was washed 5 times with water, once with brine, dried over anhydrous Na$_2$SO$_4$, filtered and concentrated to provide the crude ester which was used directly in the next reaction.

The crude ester was dissolved in EtOH (2 mL) and THF (1 mL). At ambient temperature, 3 N NaOH (2 mL) was added and the reaction mixutre was stirred for 3 h. The reaction mixture was then acidified with 1 M HCl and the aqueous solution was extracted with ethyl ether. The organic phase was washed once with 1 M HCl, once with brine, dried over anhydrous Na$_2$SO$_4$, filtered and concentrated. The crude acid was triturated with ethyl ether/hexanes and the solid was collected on a Hirsch funnel and washed several times with hexane to afford 25 mg of the title compound as a yellow solid. ESI-MS m/z 387 (M–H)$^-$. 1H NMR (CDCl$_3$) δ 8.91 (br s, 1H), 6.99 (s, 1H), 4.69 (dt, J=46.8, 5.8 Hz, 2 H), 4.09 (m, 4H), 3.11 (m, 4H), 1.89–2.35 (m, 4H), 2.09 (s, 3H), 1.23–1.59 (m, 2H), 0.91. (t, J=7.0 Hz, 3H) ppm.

TABLE 2

Pyranoindole derivatives

| EX | LC@254 minutes | MS |
|---|---|---|
| 1 | 2.61 | 311 (M – H) |
| 2 | 6.98* | |
| 3 | 9.37* | |
| 4 | 2.58 | 315 (M – H) |
| 5 | 6.18* | |
| 6 | 8.32* | |
| 7 | 3.15 | 340 (M – H) |
| 8 | 15.1* | |
| 9 | 10.2* | |
| 10 | 2.803 | 329 (M – H) |
| 11 | 7.19* | |
| 12 | 9.27* | |
| 13 | 2.663 | 316 (M + Na) |
| 14 | 2.849 | 330 (M + Na) |
| 15 | 2.892 | 330 (M + Na) |
| 16 | 3.096 | 356 (M + Na) |
| 17 | 3.010 | 364 (M + Na) |
| 18 | 3.113 | 409 (M + Na) |
| 19 | 3.031 | 409 (M + Na) |
| 20 | 3.029 | 382 (M + Na) |
| 21 | 2.716 | 362 (M + Na) |

TABLE 2-continued

Pyranoindole derivatives

| EX | LC@254 minutes | MS |
|---|---|---|
| 22 | 2.919 | 376 (M + Na) |
| 23 | 2.947 | 376 (M + Na) |
| 24 | 3.157 | 400 (M + Na) |
| 25 | 2.825 | 399 (M + Na) |
| 26 | 3.067 | 410 (M + Na) |
| 27 | 2.930 | 500 (M + Na) |
| 28 | 3.136 | 453 (M + Na) |
| 29 | 3.082 | 453 (M + Na) |
| 30 | 3.093 | 428 (M + Na) |
| 31 | 3.103 | 372 (M + Na) |
| 32 | 3.27 | 386 (M + Na) |
| 33 | 3.039 | 402 (M + Na) |
| 34 | 3.352 | 406 (M + Na) |
| 35 | 3.44 | 440 (M + Na) |
| 36 | 3.411 | 440 (M + Na) |
| 37 | 3.047 | 378 (M + Na) |
| 38 | 3.401 | 422 (M + Na) |
| 39 | 3.569 | 448 (M + Na) |
| 40 | 2.884 | 362 (M + Na) |
| 41 | 3.407 | 452 (M + Na) |
| 42 | 3.227 | 386 (M + Na) |
| 43 | 2.991 | 402 (M + Na) |
| 44 | 3.158 | 406 (M + Na) |
| 45 | 3.199 | 440 (M + Na) |
| 46 | 3.259 | 418 (M + Na) |
| 47 | 3.051 | 402 (M + Na) |
| 48 | 3.157 | 390 (M + Na) |
| 49 | 3.327 | 406 (M + Na) |
| 50 | 3.364 | 390 (M + Na) |
| 51 | 3.217 | 364 (M + Na) |
| 52 | 2.741 | 398 (M + Na) |
| 53 | 3.708 | 388 (M + Na) |
| 54 | 3.999 | 406 (M + Na) |
| 55 | 3.74 | 488 (M + Na) |
| 56 | 3.806 | 416 (M + Na) |
| 57 | 3.549 | 442 (M + Na) |
| 58 | 2.472 | 321 (M + Na) |
| 59 | 2.470 | 321 (M + Na) |
| 60 | 2.723 | 347 (M + Na) |
| 61 | 2.364 | 345 (M + Na) |
| 62 | 2.614 | 355 (M + Na) |
| 63 | 2.489 | 423 (M + H) |
| 64 | 2.673 | 400 (M + Na) |
| 65 | 2.636 | 400 (M + Na) |
| 66 | 2.625 | 373 (M + Na) |
| 67 | 3.321 | 378 (M + Na) |
| 68 | 3.067 | 388 (M + Na) |
| 69 | 3.017 | 344 (M + Na) |
| 70 | 2.242 | 360 (M + Na) |
| 71 | 2.035 | 346 (M + Na) |
| 72 | 2.346 | 302 (M + Na) |
| 73 | 2.540 | 316 (M + Na) |
| 74 | 2.744 | 330 (M + Na) |
| 75 | 2.792 | 330 (M + Na) |
| 76 | 2.926 | 344 (M + Na) |
| 77 | 2.982 | 356 (M + Na) |
| 78 | 2.880 | 342 (M + H) |
| 79 | 2.629 | 354 (M + Na) |
| 80 | 2.409 | 346 (M + Na) |
| 81 | 2.606 | 360 (M + Na) |
| 82 | 2.794 | 374 (M + Na) |
| 83 | 2.845 | 374 (M + Na) |
| 84 | 2.965 | 388 (M + Na) |
| 85 | 3.025 | 400 (M + Na) |
| 86 | 2.931 | 408 (M + Na) |
| 87 | 2.585 | 452 (M + Na) |
| 88 | 2.690 | 398 (M + Na) |
| 89 | 3.125 | 350 (M + H) |
| 90 | 3.274 | 364 (M + H) |
| 91 | 3.129 | 380 (M + H) |
| 92 | 3.339 | 384 (M + H) |
| 93 | 3.355 | 440 (M + Na) |
| 94 | 3.443 | 418 (M + H) |
| 95 | 2.813 | 374 (M + Na) |
| 96 | 2.816 | 452 (M + Na) |
| 97 | 2.586 | 365 (M + H) |
| 98 | 2.521 | 321 (M + H) |
| 99 | 2.783 | 312 (M − H) |
| 100 | 2.952 | 326 (M − H) |
| 101 | 3.138 | 340 (M − H) |
| 102 | 3.204 | 340 (M − H) |
| 103 | 3.302 | 354 (M − H) |
| 104 | 3.376 | 366 (M − H) |
| 105 | 2.792 | 374 (M − H) |
| 106 | 2.877 | 418 (M − H) |
| 107 | 2.703 | 312 (M − H) |
| 108 | 2.877 | 326 (M − H) |
| 109 | 3.049 | 340 (M − H) |
| 110 | 3.088 | 340 (M − H) |
| 111 | 3.210 | 354 (M − H) |
| 112 | 3.289 | 366 (M − H) |
| 113 | 2.826 | 418 (M − H) |
| 114 | 2.818 | 312 (M − H) |
| 115 | 2.564 | 314 (M + H) |
| 116 | 2.759 | 328 (M + H) |
| 117 | 2.944 | 364 (M + Na) |
| 118 | 3.013 | 363 (M + Na) |
| 119 | 3.101 | 378 (M + Na) |
| 120 | 3.160 | 368 (M + H) |
| 121 | 3.062 | 376 (M + H) |
| 122 | 2.283 | 304 (M + Na) |
| 123 | 2.468 | 318 (M + Na) |
| 124 | 2.684 | 332 (M + Na) |
| 125 | 2.693 | 332 (M + Na) |
| 126 | 2.862 | 324 (M + H) |
| 127 | 2.917 | 358 M + Na) |
| 128 | 2.451 | 410 (M + Na) |
| 129 | 2.852 | 346 (M − H) |
| 130 | 3.013 | 360 (M − H) |
| 131 | 3.198 | 374 (M − H) |
| 132 | 3.269 | 374 (M − H) |
| 133 | 3.341 | 388 (M − H) |
| 134 | 3.404 | 400 (M − H) |
| 135 | 3.332 | 408 (M − H) |
| 136 | 3.079 | 398 (M − H) |
| 137 | 2.413 | 296 (M + Na) |
| 138 | 2.556 | 310 (M + Na) |
| 139 | 2.794 | 324 (M + Na) |
| 140 | 2.506 | 276 (M − H) |
| 141 | 2.852 | 304 (M − H) |
| 142 | 2.653 | 290 (M − H) |
| 143 | 2.881 | 304 (M − H) |
| 144 | 3.018 | 318 (M − H) |
| 145 | 3.093 | 330 (M − H) |
| 146 | 3.583 | 338 (M − H) |
| 147 | 3.202 | 366 (M − H) |
| 148 | 3.378 | 380 (M − H) |
| 149 | 3.140 | 396 (M − H) |
| 150 | 3.478 | 434 (M − H) |
| 151 | 2.393 | 381 (M − H) |
| 152 | 2.897 | 368 (M − H) |
| 153 | 3.064 | 364 (M − H) |
| 154 | 3.002 | 346 (M − H) |
| 155 | 3.170 | 360 (M − H) |
| 156 | 3.362 | 374 (M − H) |
| 157 | 3.432 | 374 (M − H) |
| 158 | 3.528 | 388 (M − H) |
| 159 | 3.575 | 402 (M − H) |
| 160 | 3.492 | 408 (M − H) |
| 161 | 3.088 | 452 (M − H) |
| 162 | 3.236 | 398 (M − H) |
| 163 | 2.827 | 254 (M − H) |
| 164 | 3.043 | 368 (M − H) |
| 165 | 3.237 | 382 (M − H) |
| 166 | 3.277 | 382 (M − H) |
| 167 | 3.397 | 396 (M − H) |
| 168 | 3.377 | 416 (M − H) |
| 169 | 2.963 | 461 (M − H) |

TABLE 2-continued

Pyranoindole derivatives

| EX | LC@254 minutes | MS |
|---|---|---|
| 170 | 2.939 | 343 (M − H) |
| 171 | 2.876 | 363 (M − H) |
| 172 | 2.484 | 407 (M − H) |
| 173 | 3.148 | 370 (M − H) |
| 174 | 3.337 | 384 (M − H) |
| 175 | 3.519 | 398 (M − H) |
| 176 | 3.600 | 398 (M − H) |
| 177 | 3.683 | 412 (M − H) |
| 178 | 3.735 | 424 (M − H) |
| 179 | 3.643 | 432 (M − H) |
| 180 | 3.284 | 476 (M − H) |
| 181 | 2.572 | 317 (M − H) |
| 182 | 2.767 | 331 (M − H) |
| 183 | 2.967 | 345 (M − H) |
| 184 | 3.041 | 345 (M − H) |
| 185 | 3.135 | 359 (M − H) |
| 186 | 3.187 | 371 (M − H) |
| 187 | 3.097 | 379 (M − H) |
| 188 | 2.682 | 423 (M − H) |
| 189 | 2.907 | 372 (M − H) |
| 190 | 3.090 | 388 (M − H) |
| 191 | 3.252 | 402 (M − H) |
| 192 | 2.977 | 412 (M − H) |
| 193 | 3.129 | 388 (M − H) |
| 194 | 2.524 | 319 (M − H) |
| 195 | 2.725 | 333 (M − H) |
| 196 | 2.907 | 347 |
| 197 | 2.604 | 357 (M − H) |
| 198 | 2.739 | 333 (M − H) |
| 199 | 2.799 | 356 (M − H) |
| 200 | 2.953 | 370 (M − H) |
| 201 | 3.137 | 384 (M − H) |
| 202 | 3.181 | 384 (M − H) |
| 203 | 3.287 | 398 (M − H) |
| 204 | 2.862 | 462 (M − H) |
| 205 | 2.481 | 301 (M − H) |
| 206 | 2.598 | 315 (M − H) |
| 207 | 2.820 | 329 (M − H) |
| 208 | 2.964 | 343 (M − H) |
| 209 | 2.514 | 407 (M − H) |
| 210 | 3.117 | 416 (M − H) |
| 211 | 3.314 | 430 (M − H) |
| 212 | 3.397 | 430 (M − H) |
| 213 | 3.478 | 444 (M − H) |
| 214 | 3.006 | 324 (M − H) |
| 215 | 3.125 | 416 (M − H) |
| 216 | 3.354 | 354 (M − H) |
| 217 | 3.491 | 446 (M − H) |
| 218 | 3.222 | 338 (M − H) |
| 219 | 2.391 | 301 (M − H) |
| 220 | 2.561 | 315 (M − H) |
| 221 | 2.758 | 315 (M − H) |
| 222 | 2.768 | 329 (M − H) |
| 223 | 2.996 | 355 (M − H) |
| 224 | 1.936 | 345 (M + H) |
| 225 | 2.073 | 405 (M − H) |
| 226 | 1.756 | 329 (M − H) |
| 227 | 2.127 | 357 (M − 1) |
| 228 | 2.775 | 329 (M + H) |
| 229 | 3.308 | 355 ((M − 1) |
| 230 | 3.431 | 369 (M − 1) |
| 231 | 3.524 | 381 (M − 1) |
| 232 | 3.313 | 355 ((M − 1) |
| 233 | 3.457 | 381 (M − 1) |
| 234 | 3.066 | 431 (M − 1) |
| 235 | | 353 (M − H) |
| 236 | | 368 (M+) |
| 237 | | 344 (M+) |
| 238 | | 356 (M − H) |
| 239 | | 395 (M − H) |
| 240 | | 342 (M) |
| 241 | | 358 (M) |
| 242 | | 313 (M − H) |
| 243 | | 327 (M − H) |
| 244 | | |
| 245 | | 396 (M+) |
| 246 | | 344 (M+) |
| 247 | | 256 (M − 2H) |
| 248 | | 358 (M+) |
| 249 | | 360 (M+) |
| 250 | | 374 (M+) |
| 251 | | 354 (M+) |
| 252 | | 340 (M+) |
| 253 | | 354 (M+) |
| 254 | | 368 (M+) |
| 255 | | 382 (M+) |
| 256 | | 354 (M − 2H) |
| 257 | | 352 (M − 2H) |
| 258 | | 381 (M − H) |
| 259 | | 332 (M − H) |
| 260 | | 321 (M+) |
| 261 | | 334 (M − H) |
| 262 | | 320 (M − H) |
| 263 | | 428 (M − H) |
| 264 | | 376 (M − H) |
| 265 | | 392 (M + H) |
| 266 | | 392 (M + H) |
| 267 | | 388 (M+) |
| 268 | | 358 (M − H) |
| 269 | | 370 (M − H) |
| 270 | | 384 (M − H) |
| 271 | | 408 (M − H) |
| 272 | | 354 (M − H) |
| 273 | | 368 (M − H) |
| 274 | | 354 (M + H) |
| 275 | | 368 (M + H) |
| 276 | | 365 (M − H) |
| 277 | | 577 (M − H) |
| 278 | | 397 (M − H) |
| 279 | | 379 (M − H) |
| 280 | | 365 (M − H) |
| 281 | | 313 (M − H) |
| 282 | | 329 (M − H) |
| 283 | | 309 (M − H) |
| 284 | | 323 (M − H) |
| 285 | | 323 (M − H) |
| 286 | | |
| 287 | | 339 (M + H) |
| 288 | | 351 (M − H) |
| 289 | | 325 (M − H) |
| 290 | | 325 (M − H) |
| 291 | | 327 (M + H) |
| 292 | | 325 (M − H) |
| 293 | | 327 (M + H) |
| 294 | | 339 (M − H) |
| 295 | | 325 (M − H) |
| 296 | | 339 (M − H) |
| 297 | | 341 (M + H) |
| 298 | | 331 (M − H) |
| 299 | | 343 (M − H) |
| 300 | | 347 (M + H) |
| 301 | | 369 (M − H) |
| 302 | | 327 (M − H) |
| 303 | | 317 (M − H) |
| 304 | | 331 (M − H) |
| 305 | | 333 (M − H) |
| 306 | | 313 (M − H) |
| 307 | | 327 (M − H) |
| 308 | | 341 (M − H) |
| 309 | | 355 (M − H) |
| 310 | | 355 (M − H) |
| 311 | | 343 (M − H) |
| 312 | | 329 (M − H) |
| 313 | | |
| 314 | | |
| 315 | | |
| 316 | | |
| 317 | | 341 (M − H) |

TABLE 2-continued

Pyranoindole derivatives

| EX | LC@254 minutes | MS |
|---|---|---|
| 318 | | 343 (M − H) |
| 319 | | 343 (M − H) |
| 320 | | 343 (M − H) |
| 321 | | 331 (M − H) |
| 322 | | 331 (M − H) |
| 323 | | 331 (M − H) |
| 324 | | 345 (M − H) |
| 325 | | 345 (M − H) |
| 326 | | 345 (M − H) |
| 327 | | 343 (M − H) |
| 328 | | |
| 329 | | 328 (M+) |
| 330 | | 306 (M − H) |
| 331 | | 362 (M+) |
| 332 | | 344 (M − H) |
| 333 | | 340 (M − H) |
| 334 | | 297 (M − H) |
| 335 | | 312 (M+) |
| 336 | | 312 (M+) |
| 337 | | 313 (M + H) |
| 338 | | 309 (M − H) |
| 339 | | 315 (M − H) |
| 340 | | 311 (M − H) |
| 341 | | 317 (M − H) |
| 342 | | 302 (M−) |
| 343 | | |
| 344 | | 301 (M − H) |
| 345 | | 315 (M − H) |
| 346 | | 314 (M+) |
| 347 | | 317 (M + H) |
| 348 | | 315 (M − H) |
| 349 | | |
| 350 | | 328 (M+) |
| 351 | | 342 (M+) |
| 352 | | 317 (M − H) |
| 353 | | 355 (M − H) |
| 354 | | 398 (M + H) |
| 355 | | 398 (M + H) |
| 356 | | 440 (M + H) |
| 357 | | 368 (M + H) |
| 358 | | 384 (M + H) |
| 359 | | 371 (M + H) |
| 360 | | 371 (M + H) |
| 361 | | 371 (M + H) |
| 362 | | 357 (M − H) |
| 363 | | 341 (M − H) |
| 364 | | 369 (M − H) |
| 365 | | 383 (M + H) |
| 366 | | 411 (M − H) |
| 367 | | 435 (M − H) |
| 368 | | 419 (M + H) |

EXAMPLE 1

(5-cyano-8-methyl-1-propyl-1,3,4,9-tetrahydro-pyrano[3,4-b]indol-1-yl)acetic acid

EXAMPLE 2

[(R)-5-cyano-8-methyl-1-propyl-1,3,4,9-tetrahydro-pyrano[3,4-b]indol-1-yl]acetic acid

EXAMPLE 3

[(S)-5-cyano-8-methyl-1-propyl-1,3,4,9-tetrahydro-pyrano[3,4-b]indol-1-yl]acetic acid

EXAMPLE 4

(5-cyano-8-fluoro-1-propyl-1,3,4,9-tetrahydro-pyrano[3,4-b]indol-1-yl)acetic acid

EXAMPLE 5

[(R)-5-cyano-8-fluoro-1-propyl-1,3,4,9-tetrahydro-pyrano[3,4-b]indol-1-yl]acetic acid

EXAMPLE 6

[(S)-5-cyano-8-fluoro-1-propyl-1,3,4,9-tetrahydro-pyrano[3,4-b]indol-1-yl]acetic acid

EXAMPLE 7

(5,8-dichloro-1-propyl-1,3,4,9-tetrahydro-pyrano[3,4-b]indol-1-yl)acetic acid

EXAMPLE 8

[(R)-5,8-dichloro-1-propyl-1,3,4,9-tetrahydropyrano[3,4-b]indol-1-yl]acetic acid

EXAMPLE 9

[(S)-5,8-dichloro-1-propyl-1,3,4,9-tetrahydropyrano[3,4-b]indol-1-yl]acetic acid

EXAMPLE 10

(5-cyano-6-fluoro-8-methyl-1-propyl-1,3,4,9-tetrahydropyrano[3,4-b]indol-1-yl)acetic acid

EXAMPLE 11

[(R)-5-cyano-6-fluoro-8-methyl-1-propyl-1,3,4,9-tetrahydropyrano[3,4-b]indol-1-yl]acetic acid

EXAMPLE 12

[(S)-5-cyano-6-fluoro-8-methyl-1-propyl-1,3,4,9-tetrahydropyrano[3,4-b]indol-1-yl]acetic acid

EXAMPLE 13

(5-Chloro-1-ethyl-1,3,4,9-tetrahydropyrano[3,4-b]indol-1-yl)acetic acid

EXAMPLE 14

(5-Chloro-1-propyl-1,3,4,9-tetrahydropyrano[3,4-b]indol-1-yl)acetic acid

EXAMPLE 15

(5-chloro-1-isopropyl-1,3,4,9-tetrahydropyrano[3,4-b]indol-1-yl)acetic acid

EXAMPLE 16

{5-chloro-1-[(3E)-pent-3-enyl]-1,3,4,9-tetrahydropyrano[3,4-b]indol-1-yl}acetic acid

EXAMPLE 17

(5-chloro-1-phenyl-1,3,4,9-tetrahydropyrano[3,4-b]
indol-1-yl)acetic acid

EXAMPLE 18

[5-chloro-1-(4-nitrophenyl)-1,3,4,9-tetrahydropyrano
[3,4-b]indol-1-yl]acetic acid

EXAMPLE 19

[5-chloro-1-(3-nitrophenyl)-1,3,4,9-tetrahydropyrano
[3,4-b]indol-1-yl]acetic acid

EXAMPLE 20

[5-chloro-1-(2-fluorophenyl)-1,3,4,9-tetrahydropy-
rano[3,4-b]indol-1-yl]acetic acid

EXAMPLE 21

(5-bromo-1-ethyl-1,3,4,9-tetrahydro-pyrano[3,4-b]
indol-1-yl)acetic acid

EXAMPLE 22

(5-bromo-1-propyl-1,3,4,9-tetrahydropyrano[3,4-b]
indol-1-yl)acetic acid

EXAMPLE 23

(5-bromo-1-isopropyl-1,3,4,9-tetrahydropyrano[3,4-
b]indol-1-yl)acetic acid

EXAMPLE 24

{5-bromo-1-[(3E)-pent-3-enyl]-1,3,4,9-tetrahydropy-
rano[3,4-b]indol-1-yl}acetic acid

EXAMPLE 25

[5-bromo-1-(3-furyl)-1,3,4,9-tetrahydropyrano[3,4-
b]indol-1-yl]acetic acid

EXAMPLE 26

(5-bromo-1-phenyl-1,3,4,9-tetrahydropyrano[3,4-b]
indol-1-yl)acetic acid

EXAMPLE 27

[5-bromo-1-(3,4,5-trimethoxyphenyl)-1,3,4,9-tet-
rahydropyrano[3,4-b]indol-1-yl]acetic acid

EXAMPLE 28

[5-bromo-1-(4-nitrophenyl)-1,3,4,9-tetrahydropy-
rano[3,4-b]indol-1-yl]acetic acid

EXAMPLE 29

[5-bromo-1-(3-nitrophenyl)-1,3,4,9-tetrahydropy-
rano[3,4-b]indol-1-yl]acetic acid

EXAMPLE 30

[5-bromo-1-(2-fluorophenyl)-1,3,4,9-tetrahydropy-
rano[3,4-b]indol-1-yl]acetic acid

EXAMPLE 31

(5-phenyl-1-propyl-1,3,4,9-tetrahydropyrano[3,4-b]
indol-1-yl)acetic acid

EXAMPLE 32

[5-(4-methylphenyl)-1-propyl-1,3,4,9-tetrahydropy-
rano[3,4-b]indol-1-yl]acetic acid

EXAMPLE 33

[5-(4-methoxyphenyl)-1-propyl-1,3,4,9-tetrahydro-
pyrano[3,4-b]indol-1-yl]acetic acid

EXAMPLE 34

(5-(4-chlorophenyl)-1-propyl-1,3,4,9-tetrahydropy-
rano[3,4-b]indol-1-yl)acetic acid

EXAMPLE 35

[5-(2,4-dichlorophenyl)-1-propyl-1,3,4,9-tetrahydro-
pyrano[3,4-b]indol-1-yl]acetic acid

EXAMPLE 36

{1-propyl-5-[4-(trifluoromethyl)phenyl]-1,3,4,9-
tetrahydropyrano[3,4-b]indol-1-yl}acetic acid

EXAMPLE 37

(1-propyl-5-thien-2-yl-1,3,4,9-tetrahydropyrano[3,4-
b]indol-1-yl)acetic acid

EXAMPLE 38

[5-(2-naphthyl)-1-propyl-1,3,4,9-tetrahydropyrano[3,
4-b]indol-1-yl]acetic acid

EXAMPLE 39

[5-(1,1'-biphenyl-4-yl)-1-propyl-1,3,4,9-tetrahydro-
pyrano[3,4-b]indol-1-yl]acetic acid

EXAMPLE 40

[5-(2-furyl)-1-propyl-1,3,4,9-tetrahydropyrano[3,4-
b]indol-1-yl]acetic acid

EXAMPLE 41

[5-(4-bromophenyl)-1-propyl-1,3,4,9-tetrahydropy-
rano[3,4-b]indol-1-yl]acetic acid

EXAMPLE 42

[5-(2-methylphenyl)-1-propyl-1,3,4,9-tetrahydropy-
rano[3,4-b]indol-1-yl]acetic acid

EXAMPLE 43

[5-(2-methoxyphenyl)-1-propyl-1,3,4,9-tetrahydro-pyrano[3,4-b]indol-1-yl]acetic acid

EXAMPLE 44

[5-(2-chlorophenyl)-1-propyl-1,3,4,9-tetrahydropyrano[3,4-b]indol-1-yl]acetic acid

EXAMPLE 45

(1-propyl-5-[2-(trifluoromethyl)phenyl]-1,3,4,9-tetrahydropyrano[3,4-b]indol-1-yl)acetic acid

EXAMPLE 46

(5-[4-(methylthio)phenyl]-1-propyl-1,3,4,9-tetrahydropyrano[3,4-b]indol-1-yl)acetic acid

EXAMPLE 47

[5-(3-methoxyphenyl)-1-propyl-1,3,4,9-tetrahydro-pyrano[3,4-b]indol-1-yl]acetic acid

EXAMPLE 48

[5-(4-fluorophenyl)-1-propyl-1,3,4,9-tetrahydropyrano[3,4-b]indol-1-yl]acetic acid

EXAMPLE 49

[5-(3-chlorophenyl)-1-propyl-1,3,4,9-tetrahydropyrano[3,4-b]indol-1-yl]acetic acid

EXAMPLE 50

(5,8-dichloro-1-[(3E)-pent-3-enyl]-1,3,4,9-tetrahydropyrano[3,4-b]indol-1-yl)acetic acid

EXAMPLE 51

(5,8-dichloro-1-isopropyl-1,3,4,9-tetrahydropyrano[3,4-b]indol-1-yl)acetic acid

EXAMPLE 52

(5,8-dichloro-1-phenyl-1,3,4,9-tetrahydropyrano[3,4-b]indol-1-yl)acetic acid

EXAMPLE 53

[5,8-dichloro-1-(3-furyl)-1,3,4,9-tetrahydropyrano[3,4-b]indol-1-yl]acetic acid

EXAMPLE 54

[5,8-dichloro-1-(4-methylpentyl)-1,3,4,9-tetrahydro-pyrano[3,4-b]indol-1-yl]acetic acid

EXAMPLE 55

[5,8-dichloro-1-(3,4,5-trimethoxyphenyl)-1,3,4,9-tetrahydropyrano[3,4-b]indol-1-yl]acetic acid

EXAMPLE 56

[5,8-dichloro-1-(2-fluorophenyl)-1,3,4,9-tetrahydro-pyrano[3,4-b]indol-1-yl]acetic acid

EXAMPLE 57

4-[1-(carboxymethyl)-5,8-dichloro-1,3,4,9-tetrahy-dropyrano[3,4-b]indol-1-yl]benzoic acid

EXAMPLE 58

(5-cyano-1-propyl-1,3,4,9-tetrahydro-pyrano[3,4-b]indol-1-yl)acetic acid

EXAMPLE 59

(5-cyano-1-isopropyl-1,3,4,9-tetrahydropyrano[3,4-b]indol-1-yl)acetic acid

EXAMPLE 60

{5-cyano-1-[(3E)-pent-3-enyl]-1,3,4,9-tetrahydropyrano[3,4-b]indol-1-yl}acetic acid

EXAMPLE 61

[5-cyano-1-(3-furyl)-1,3,4,9-tetrahydropyrano[3,4-b]indol-1-yl]acetic acid

EXAMPLE 62

(5-cyano-1-phenyl-1,3,4,9-tetrahydropyrano[3,4-b]indol-1-yl)acetic acid

EXAMPLE 63

[5-cyano-1-(3,4,5-trimethoxyphenyl)-1,3,4,9-tet-rahydropyrano[3,4-b]indol-1-yl]acetic acid

EXAMPLE 64

[5-cyano-1-(4-nitrophenyl)-1,3,4,9-tetrahydropyrano[3,4-b]indol-1-yl]acetic acid

EXAMPLE 65

[5-cyano-1-(3-nitrophenyl)-1,3,4,9-tetrahydropyrano[3,4-b]indol-1-yl]acetic acid

EXAMPLE 66

[5-cyano-1-(2-fluorophenyl)-1,3,4,9-tetrahydropyrano[3,4-b]indol-1-yl]acetic acid

EXAMPLE 67

(1-butyl-5,8-dichloro-1,3,4,9-tetrahydropyrano[3,4-b]indol-1-yl)acetic acid

EXAMPLE 68

(5-bromo-1-butyl-1,3,4,9-tetrahydropyrano[3,4-b]indol-1-yl)acetic acid

EXAMPLE 69

(1-butyl-5-chloro-1,3,4,9-tetrahydropyrano[3,4-b]
indol-1-yl)acetic acid

EXAMPLE 70

[5-chloro-1-(2-methoxy-2-oxoethyl)-1,3,4,9-tetrahy-
dropyrano[3,4-b]indol-1-yl]acetic acid

EXAMPLE 71

[1-(carboxymethyl)-5-chloro-1,3,4,9-tetrahydropy-
rano[3,4-b]indol-1-yl]acetic acid

EXAMPLE 72

(8-chloro-1-methyl-1,3,4,9-tetrahydropyrano[3,4-b]
indol-1-yl)acetic acid

EXAMPLE 73

(8-chloro-1-ethyl-1,3,4,9-tetrahydropyrano[3,4-b]
indol-1-yl)acetic acid

EXAMPLE 74

(8-chloro-1-propyl-1,3,4,9-tetrahydropyrano[3,4-b]
indol-1-yl)acetic acid

EXAMPLE 75

(8-chloro-1-isopropyl-1,3,4,9-tetrahydropyrano[3,4-
b]indol-1-yl)acetic acid

EXAMPLE 76

(1-butyl-8-chloro-1,3,4,9-tetrahydropyrano[3,4-b]
indol-1-yl)acetic acid

EXAMPLE 77

{8-chloro-1-[(3E)-pent-3-enyl]-1,3,4,9-tetrahydropy-
rano[3,4-b]indol-1-yl}acetic acid

EXAMPLE 78

(8-chloro-1-phenyl-1,3,4,9-tetrahydropyrano[3,4-b]
indol-1-yl)acetic acid

EXAMPLE 79

[8-chloro-1-(3-furyl)-1,3,4,9-tetrahydropyrano[3,4-
b]indol-1-yl]acetic acid

EXAMPLE 80

(8-bromo-1-methyl-1,3,4,9-tetrahydropyrano[3,4-b]
indol-1-yl)acetic acid

EXAMPLE 81

(8-bromo-1-ethyl-1,3,4,9-tetrahydropyrano[3,4-b]
indol-1-yl)acetic acid

EXAMPLE 82

(8-bromo-1-propyl-1,3,4,9-tetrahydropyrano[3,4-b]
indol-1-yl)acetic acid

EXAMPLE 83

(8-bromo-1-isopropyl-1,3,4,9-tetrahydropyrano[3,4-
b]indol-1-yl)acetic acid

EXAMPLE 84

(8-bromo-1-butyl-1,3,4,9-tetrahydropyrano[3,4-b]
indol-1-yl)acetic acid

EXAMPLE 85

{8-bromo-1-[(3E)-pent-3-enyl]-1,3,4,9-tetrahydropy-
rano[3,4-b]indol-1-yl}acetic acid

EXAMPLE 86

(8-bromo-1-phenyl-1,3,4,9-tetrahydropyrano[3,4-b]
indol-1-yl)acetic acid

EXAMPLE 87

4-[8-bromo-1-(carboxymethyl)-1,3,4,9-tetrahydropy-
rano[3,4-b]indol-1-yl]benzoic acid

EXAMPLE 88

[8-bromo-1-(3-furyl)-1,3,4,9-tetrahydropyrano[3,4-
b]indol-1-yl]acetic acid

EXAMPLE 89

(8-phenyl-1-propyl-1,3,4,9-tetrahydropyrano[3,4-b]
indol-1-yl)acetic acid

EXAMPLE 90

[8-(4-methylphenyl)-1-propyl-1,3,4,9-tetrahydropy-
rano[3,4-b]indol-1-yl]acetic acid

EXAMPLE 91

[8-(4-methoxyphenyl)-1-propyl-1,3,4,9-tetrahydro-
pyrano[3,4-b]indol-1-yl]acetic acid

EXAMPLE 92

[8-(4-chlorophenyl)-1-propyl-1,3,4,9-tetrahydropy-
rano[3,4-b]indol-1-yl]acetic acid

EXAMPLE 93

[8-(2,4-dichlorophenyl)-1-propyl-1,3,4,9-tetrahydro-
pyrano[3,4-b]indol-1-yl]acetic acid

EXAMPLE 94

{1-propyl-8-[4-(trifluoromethyl)phenyl]-1,3,4,9-
tetrahydropyrano[3,4-b]indol-1-yl}acetic acid

EXAMPLE 95

(1-propyl-8-thien-2-yl-1,3,4,9-tetrahydropyrano[3,4-b]indol-1-yl)acetic acid

EXAMPLE 96

[8-(3-bromophenyl)-1-propyl-1,3,4,9-tetrahydropyrano[3,4-b]indol-1-yl]acetic acid

EXAMPLE 97

[8-(3-aminophenyl)-1-propyl-1,3,4,9-tetrahydropyrano[3,4-b]indol-1-yl]acetic acid

EXAMPLE 98

(8-cyano-1-propyl-1,3,4,9-tetrahydropyrano[3,4-b]indol-1-yl)acetic acid

EXAMPLE 99

(6,8-dichloro-1-methyl-1,3,4,9-tetrahydropyrano[3,4-b]indol-1-yl)acetic acid

EXAMPLE 100

(6,8-dichloro-1-ethyl-1,3,4,9-tetrahydropyrano[3,4-b]indol-1-yl)acetic acid

EXAMPLE 101

(6,8-dichloro-1-propyl-1,3,4,9-tetrahydropyrano[3,4-b]indol-1-yl)acetic acid

EXAMPLE 102

(6,8-dichloro-1-isopropyl-1,3,4,9-tetrahydropyrano[3,4-b]indol-1-yl)acetic acid

EXAMPLE 103

(1-butyl-6,8-dichloro-1,3,4,9-tetrahydropyrano[3,4-b]indol-1-yl)acetic acid

EXAMPLE 104

{6,8-dichloro-1-[(3E)-pent-3-enyl]-1,3,4,9-tetrahydropyrano[3,4-b]indol-1-yl}acetic acid

EXAMPLE 105

(6,8-dichloro-1-phenyl-1,3,4,9-tetrahydropyrano[3,4-b]indol-1-yl)acetic acid

EXAMPLE 106

4-[1-(carboxymethyl)-6,8-dichloro-1,3,4,9-tetrahydropyrano[3,4-b]indol-1-yl]benzoic acid

EXAMPLE 107

(5,6-dichloro-1-methyl-1,3,4,9-tetrahydropyrano[3,4-b]indol-1-yl)acetic acid

EXAMPLE 108

(5,6-dichloro-1-ethyl-1,3,4,9-tetrahydropyrano[3,4-b]indol-1-yl)acetic acid

EXAMPLE 109

(5,6-dichloro-1-propyl-1,3,4,9-tetrahydropyrano[3,4-b]indol-1-yl)acetic acid

EXAMPLE 110

(5,6-dichloro-1-isopropyl-1,3,4,9-tetrahydropyrano[3,4-b]indol-1-yl)acetic acid

EXAMPLE 111

(1-butyl-5,6-dichloro-1,3,4,9-tetrahydropyrano[3,4-b]indol-1-yl)acetic acid

EXAMPLE 112

{5,6-dichloro-1-[(3E)-pent-3-enyl]-1,3,4,9-tetrahydropyrano[3,4-b]indol-1-yl}acetic acid

EXAMPLE 113

4-[1-(carboxymethyl)-5,6-dichloro-1,3,4,9-tetrahydropyrano[3,4-b]indol-1-yl]benzoic acid

EXAMPLE 114

(5,7-dichloro-1-methyl-1,3,4,9-tetrahydropyrano[3,4-b]indol-1-yl)acetic acid

EXAMPLE 115

[1-methyl-8-(trifluoromethyl)-1,3,4,9-tetrahydropyrano[3,4-b]indol-1-yl]acetic acid

EXAMPLE 116

[1-ethyl-8-(trifluoromethyl)-1,3,4,9-tetrahydropyrano[3,4-b]indol-1-yl]acetic acid

EXAMPLE 117

[1-propyl-8-(trifluoromethyl)-1,3,4,9-tetrahydropyrano[3,4-b]indol-1-yl]acetic acid

EXAMPLE 118

[1-isopropyl-8-(trifluoromethyl)-1,3,4,9-tetrahydropyrano[3,4-b]indol-1-yl]acetic acid

EXAMPLE 119

[1-butyl-8-(trifluoromethyl)-1,3,4,9-tetrahydropyrano[3,4-b]indol-1-yl]acetic acid

EXAMPLE 120

[1-[(3E)-pent-3-enyl]-8-(trifluoromethyl)-1,3,4,9-tetrahydropyrano[3,4-b]indol-1-yl]acetic acid

EXAMPLE 121

[1-phenyl-8-(trifluoromethyl)-1,3,4,9-tetrahydropyrano[3,4-b]indol-1-yl]acetic acid

EXAMPLE 122

(5,8-difluoro-1-methyl-1,3,4,9-tetrahydropyrano[3,4-b]indol-1-yl)acetic acid

EXAMPLE 123

(1-ethyl-5,8-difluoro-1,3,4,9-tetrahydro-pyrano[3,4-b]indol-1-yl)acetic acid

EXAMPLE 124

(5,8-difluoro-1-propyl-1,3,4,9-tetrahydro-pyrano[3,4-b]indol-1-yl)acetic acid

EXAMPLE 125

(5,8-difluoro-1-isopropyl-1,3,4,9-tetrahydropyrano[3,4-b]indol-1-yl)acetic acid

EXAMPLE 126

(1-butyl-5,8-difluoro-1,3,4,9-tetrahydropyrano[3,4-b]indol-1-yl)acetic acid

EXAMPLE 127

{5,8-difluoro-1-[(3E)-pent-3-enyl]-1,3,4,9-tetrahydropyrano[3,4-b]indol-1-yl}acetic acid

EXAMPLE 128

4-[1-(carboxymethyl)-5,8-difluoro-1,3,4,9-tetrahydropyrano[3,4-b]indol-1-yl]benzoic acid

EXAMPLE 129

[8-chloro-1-methyl-5-(trifluoromethyl)-1,3,4,9-tetrahydropyrano[3,4-b]indol-1-yl]acetic acid

EXAMPLE 130

[8-chloro-1-ethyl-5-(trifluoromethyl)-1,3,4,9-tetrahydropyrano[3,4-b]indol-1-yl]acetic acid

EXAMPLE 131

[8-chloro-1-propyl-5-(trifluoromethyl)-1,3,4,9-tetrahydropyrano[3,4-b]indol-1-yl]acetic acid

EXAMPLE 132

[8-chloro-1-isopropyl-5-(trifluoromethyl)-1,3,4,9-tetrahydropyrano[3,4-b]indol-1-yl]acetic acid

EXAMPLE 133

[1-butyl-8-chloro-5-(trifluoromethyl)-1,3,4,9-tetrahydropyrano[3,4-b]indol-1-yl]acetic acid

EXAMPLE 134

[8-chloro-1-[(3E)-pent-3-enyl]-5-(trifluoromethyl)-1,3,4,9-tetrahydropyrano[3,4-b]indol-1-yl]acetic acid

EXAMPLE 135

[8-chloro-1-phenyl-5-(trifluoromethyl)-1,3,4,9-tetrahydropyrano[3,4-b]indol-1-yl]acetic acid

EXAMPLE 136

[8-chloro-1-(3-furyl)-5-(trifluoromethyl)-1,3,4,9-tetrahydropyrano[3,4-b]indol-1-yl]acetic acid

EXAMPLE 137

(1,5,8-trimethyl-1,3,4,9-tetrahydropyrano[3,4-b]indol-1-yl)acetic acid

EXAMPLE 138

(1-ethyl-5,8-dimethyl-1,3,4,9-tetrahydropyrano[3,4-b]indol-1-yl)acetic acid

EXAMPLE 139

(5,8-dimethyl-1-propyl-1,3,4,9-tetrahydropyrano[3,4-b]indol-1-yl)acetic acid

EXAMPLE 140

(5-fluoro-1,8-dimethyl-1,3,4,9-tetrahydropyrano[3,4-b]indol-1-yl)acetic acid

EXAMPLE 141

(5-fluoro-8-methyl-1-propyl-1,3,4,9-tetrahydropyrano[3,4-b]indol-1-yl)acetic acid

EXAMPLE 142

(1-ethyl-5-fluoro-1,3,4,9-tetrahydro-8-methyl-pyrano[3,4-b]indol-1-yl)acetic acid

EXAMPLE 143

(5-fluoro-1-isopropyl-8-methyl-1,3,4,9-tetrahydro-pyrano[3,4-b]indol-1-yl)acetic acid

EXAMPLE 144

(1-butyl-5-fluoro-8-methyl-1,3,4,9-tetrahydropyrano[3,4-b]indol-1-yl)acetic acid

EXAMPLE 145

{5-fluoro-8-methyl-1-[(3E)-pent-3-enyl]-1,3,4,9-tetrahydropyrano[3,4-b]indol-1-yl}acetic acid

EXAMPLE 146

(5-fluoro-8-methyl-1-phenyl-1,3,4,9-tetrahydropyrano[3,4-b]indol-1-yl)acetic acid

EXAMPLE 147

(8-fluoro-5-phenyl-1-propyl-1,3,4,9-tetrahydropyrano[3,4-b]indol-1-yl)acetic acid

EXAMPLE 148

[8-fluoro-5-(4-methylphenyl)-1-propyl-1,3,4,9-tetrahydropyrano[3,4-b]indol-1-yl]acetic acid

EXAMPLE 149

[8-fluoro-5-(4-methoxyphenyl)-1-propyl-1,3,4,9-tetrahydropyrano[3,4-b]indol-1-yl]acetic acid

EXAMPLE 150

{8-fluoro-1-propyl-5-[4-(trifluoromethyl)phenyl]-1,3,4,9-tetrahydropyrano[3,4-b]indol-1-yl}acetic acid

EXAMPLE 151

[5-(3-aminophenyl)-8-fluoro-1-propyl-1,3,4,9-tetrahydropyrano[3,4-b]indol-1-yl]acetic acid

EXAMPLE 152

(5-bromo-8-fluoro-1-propyl-1,3,4,9-tetrahydropyrano[3,4-b]indol-1-yl)acetic acid

EXAMPLE 153

(5-bromo-8-methyl-1-propyl-1,3,4,9-tetrahydropyrano[3,4-b]indol-1-yl)acetic acid

EXAMPLE 154

(5,6,8-trichloro-1-methyl-1,3,4,9-tetrahydropyrano[3,4-b]indol-1-yl)acetic acid

EXAMPLE 155

(5,6,8-trichloro-1-ethyl-1,3,4,9-tetrahydropyrano[3,4-b]indol-1-yl)acetic acid

EXAMPLE 156

(5,6,8-trichloro-1-propyl-1,3,4,9-tetrahydropyrano[3,4-b]indol-1-yl)acetic acid

EXAMPLE 157

(5,6,8-trichloro-1-isopropyl-1,3,4,9-tetrahydropyrano[3,4-b]indol-1-yl)acetic acid

EXAMPLE 158

(1-butyl-5,6,8-trichloro-1,3,4,9-tetrahydropyrano[3,4-b]indol-1-yl)acetic acid

EXAMPLE 159

{5,6,8-trichloro-1-[(3E)-pent-3-enyl]-1,3,4,9-tetrahydropyrano[3,4-b]indol-1-yl}acetic acid

EXAMPLE 160

(5,6,8-trichloro-1-phenyl-1,3,4,9-tetrahydropyrano[3,4-b]indol-1-yl)acetic acid

EXAMPLE 161

4-[1-(carboxymethyl)-5,6,8-trichloro-1,3,4,9-tetrahydropyrano[3,4-b]indol-1-yl]benzoic acid

EXAMPLE 162

[5,6,8-trichloro-1-(3-furyl)-1,3,4,9-tetrahydropyrano[3,4-b]indol-1-yl]acetic acid

EXAMPLE 163

(5-bromo-8-fluoro-1,6-dimethyl-1,3,4,9-tetrahydropyrano[3,4-b]indol-1-yl)acetic acid

EXAMPLE 164

(5-bromo-1-ethyl-8-fluoro-6-methyl-1,3,4,9-tetrahydropyrano[3,4-b]indol-1-yl)acetic acid

EXAMPLE 165

(5-bromo-8-fluoro-6-methyl-1-propyl-1,3,4,9-tetrahydropyrano[3,4-b]indol-1-yl)acetic acid

EXAMPLE 166

(5-bromo-8-fluoro-1-isopropyl-6-methyl-1,3,4,9-tetrahydropyrano[3,4-b]indol-1-yl)acetic acid

EXAMPLE 167

(5-bromo-1-butyl-8-fluoro-6-methyl-1,3,4,9-tetrahydropyrano[3,4-b]indol-1-yl)acetic acid

EXAMPLE 168

(5-bromo-8-fluoro-6-methyl-1-phenyl-1,3,4,9-tetrahydropyrano[3,4-b]indol-1-yl)acetic acid

EXAMPLE 169

4-[5-bromo-1-(carboxymethyl)-8-fluoro-6-methyl-1,3,4,9-tetrahydropyrano[3,4-b]indol-1-yl]benzoic acid

EXAMPLE 170

(1-butyl-5-cyano-8-fluoro-6-methyl-1,3,4,9-tetrahydropyrano[3,4-b]indol-1-yl)acetic acid

EXAMPLE 171

(5-cyano-8-fluoro-6-methyl-1-phenyl-1,3,4,9-tetrahydropyrano[3,4-b]indol-1-yl)acetic acid

EXAMPLE 172

4-[1-(carboxymethyl)-5-cyano-8-fluoro-6-methyl-1,
3,4,9-tetrahydropyrano[3,4-b]indol-1-yl]benzoic
acid

EXAMPLE 173

(5-bromo-8-chloro-1,6-dimethyl-1,3,4,9-tetrahydropyrano[3,4-b]indol-1-yl)acetic acid

EXAMPLE 174

(5-bromo-8-chloro-1-ethyl-6-methyl-1,3,4,9-tetrahydropyrano[3,4-b]indol-1-yl)acetic acid

EXAMPLE 175

(5-bromo-8-chloro-6-methyl-1-propyl-1,3,4,9-tetrahydropyrano[3,4-b]indol-1-yl)acetic acid

EXAMPLE 176

(5-bromo-8-chloro-1-isopropyl-6-methyl-1,3,4,9-tetrahydropyrano[3,4-b]indol-1-yl)acetic acid

EXAMPLE 177

(5-bromo-1-butyl-8-chloro-6-methyl-1,3,4,9-tetrahydropyrano[3,4-b]indol-1-yl)acetic acid

EXAMPLE 178

{5-bromo-8-chloro-6-methyl-1-[(3E)-pent-3-enyl]-1,
3,4,9-tetrahydropyrano[3,4-b]indol-1-yl}acetic acid

EXAMPLE 179

(5-bromo-8-chloro-6-methyl-1-phenyl-1,3,4,9-tetrahydropyrano[3,4-b]indol-1-yl)acetic acid

EXAMPLE 180

4-[5-bromo-1-(carboxymethyl)-8-chloro-6-methyl-1,
3,4,9-tetrahydropyrano[3,4-b]indol-1-yl]benzoic
acid

EXAMPLE 181

(8-chloro-5-cyano-1,6-dimethyl-1,3,4,9-tetrahydropyrano[3,4-b]indol-1-yl)acetic acid

EXAMPLE 182

(8-chloro-5-cyano-1-ethyl-6-methyl-1,3,4,9-tetrahydropyrano[3,4-b]indol-1-yl)acetic acid

EXAMPLE 183

(8-chloro-5-cyano-6-methyl-1-propyl-1,3,4,9-tetrahydropyrano[3,4-b]indol-1-yl)acetic acid

EXAMPLE 184

(8-chloro-5-cyano-1-isopropyl-6-methyl-1,3,4,9-tetrahydropyrano[3,4-b]indol-1-yl)acetic acid

EXAMPLE 185

(1-butyl-8-chloro-5-cyano-6-methyl-1,3,4,9-tetrahydropyrano[3,4-b]indol-1-yl)acetic acid

EXAMPLE 186

{8-chloro-5-cyano-6-methyl-1-[(3E)-pent-3-enyl]-1,
3,4,9-tetrahydropyrano[3,4-b]indol-1-yl}acetic acid

EXAMPLE 187

(8-chloro-5-cyano-6-methyl-1-phenyl-1,3,4,9-tetrahydropyrano[3,4-b]indol-1-yl)acetic acid

EXAMPLE 188

4-[1-(carboxymethyl)-8-chloro-5-cyano-6-methyl-1,
3,4,9-tetrahydropyrano[3,4-b]indol-1-yl]benzoic
acid

EXAMPLE 189

(5-bromo-1-ethyl-6,8-difluoro-1,3,4,9-tetrahydropyrano[3,4-b]indol-1-yl)acetic acid

EXAMPLE 190

(5-bromo-6,8-difluoro-1-propyl-1,3,4,9-tetrahydropyrano[3,4-b]indol-1-yl)acetic acid

EXAMPLE 191

(5-bromo-1-butyl-6,8-difluoro-1,3,4,9-tetrahydropyrano[3,4-b]indol-1-yl)acetic acid

EXAMPLE 192

[5-bromo-6,8-difluoro-1-(3-furyl)-1,3,4,9-tetrahydropyrano[3,4-b]indol-1-yl]acetic acid

EXAMPLE 193

(5-bromo-6,8-difluoro-1-isopropyl-1,3,4,9-tetrahydropyrano[3,4-b]indol-1-yl)acetic acid

EXAMPLE 194

(5-cyano-1-ethyl-6,8-difluoro-1,3,4,9-tetrahydropyrano[3,4-b]indol-1-yl)acetic acid

EXAMPLE 195

(5-cyano-6,8-difluoro-1-propyl-1,3,4,9-tetrahydropyrano[3,4-b]indol-1-yl)acetic acid

EXAMPLE 196

(1-butyl-5-cyano-6,8-difluoro-1,3,4,9-tetrahydropyrano[3,4-b]indol-1-yl)acetic acid

EXAMPLE 197

[5-cyano-6,8-difluoro-1-(3-furyl)-1,3,4,9-tetrahydropyrano[3,4-b]indol-1-yl]acetic acid

EXAMPLE 198

(5-cyano-6,8-difluoro-1-isopropyl-1,3,4,9-tetrahydropyrano[3,4-b]indol-1-yl)acetic acid

EXAMPLE 199

(5-bromo-6-fluoro-1,8-dimethyl-1,3,4,9-tetrahydropyrano[3,4-b]indol-1-yl)acetic acid

EXAMPLE 200

(5-bromo-1-ethyl-6-fluoro-8-methyl-1,3,4,9-tetrahydropyrano[3,4-b]indol-1-yl)acetic acid

EXAMPLE 201

(5-bromo-6-fluoro-8-methyl-1-propyl-1,3,4,9-tetrahydropyrano[3,4-b]indol-1-yl)acetic acid

EXAMPLE 202

(5-bromo-6-fluoro-1-isopropyl-8-methyl-1,3,4,9-tetrahydropyrano[3,4-b]indol-1-yl)acetic acid

EXAMPLE 203

(5-bromo-1-butyl-6-fluoro-8-methyl-1,3,4,9-tetrahydropyrano[3,4-b]indol-1-yl)acetic acid

EXAMPLE 204

4-[5-bromo-1-(carboxymethyl)-6-fluoro-8-methyl-1,3,4,9-tetrahydropyrano[3,4-b]indol-1-yl]benzoic acid

EXAMPLE 205

(5-cyano-6-fluoro-1,8-dimethyl-1,3,4,9-tetrahydropyrano[3,4-b]indol-1-yl)acetic acid

EXAMPLE 206

(5-cyano-1-ethyl-6-fluoro-8-methyl-1,3,4,9-tetrahydropyrano[3,4-b]indol-1-yl)acetic acid

EXAMPLE 207

(5-cyano-6-fluoro-1-isopropyl-8-methyl-1,3,4,9-tetrahydropyrano[3,4-b]indol-1-yl)acetic acid

EXAMPLE 208

(1-butyl-5-cyano-6-fluoro-8-methyl-1,3,4,9-tetrahydropyrano[3,4-b]indol-1-yl)acetic acid

EXAMPLE 209

4-[1-(carboxymethyl)-5-cyano-6-fluoro-8-methyl-1,3,4,9-tetrahydropyrano[3,4-b]indol-1-yl]benzoic acid

EXAMPLE 210

(5,8-dibromo-1-ethyl-1,3,4,9-tetrahydropyrano[3,4-b]indol-1-yl)acetic acid

EXAMPLE 211

(5,8-dibromo-1-propyl-1,3,4,9-tetrahydropyrano[3,4-b]indol-1-yl)acetic acid

EXAMPLE 212

(5,8-dibromo-1-isopropyl-1,3,4,9-tetrahydropyrano[3,4-b]indol-1-yl)acetic acid

EXAMPLE 213

(5,8-dibromo-1-butyl-1,3,4,9-tetrahydropyrano[3,4-b]indol-1-yl)acetic acid

EXAMPLE 214

(5-chloro-8-fluoro-1-propyl-1,3,4,9-tetrahydropyrano[3,4-b]indol-1-yl)acetic acid

EXAMPLE 215

(8-fluoro-5-iodo-1-propyl-1,3,4,9-tetrahydropyrano[3,4-b]indol-1-yl)acetic acid

EXAMPLE 216

(5,8-dichloro-6-methyl-1-propyl-1,3,4,9-tetrahydropyrano[3,4-b]indol-1-yl)acetic acid

EXAMPLE 217

(8-chloro-5-iodo-6-methyl-1-propyl-1,3,4,9-tetrahydropyrano[3,4-b]indol-1-yl)acetic acid

EXAMPLE 218

(8-fluoro-5-iodo-6-methyl-1-propyl-1,3,4,9-tetrahydropyrano[3,4-b]indol-1-yl)acetic acid

EXAMPLE 219

(5-cyano-8-fluoro-1,6-dimethyl-1,3,4,9-tetrahydropyrano[3,4-b]indol-1-yl)acetic acid

EXAMPLE 220

(5-cyano-1-ethyl-8-fluoro-6-methyl-1,3,4,9-tetrahydropyrano[3,4-b]indol-1-yl)acetic acid

EXAMPLE 221

(5-cyano-8-fluoro-6-methyl-1-propyl-1,3,4,9-tetrahydropyrano[3,4-b]indol-1-yl)acetic acid

EXAMPLE 222

(5-cyano-8-fluoro-1-isopropyl-6-methyl-1,3,4,9-tetrahydropyrano[3,4-b]indol-1-yl)aceti acid

EXAMPLE 223

{5-cyano-8-fluoro-6-methyl-1-[(3E)-pent-3-enyl]-1,3,4,9-tetrahydropyrano[3,4-b]indol-1-yl}acetic acid

EXAMPLE 224

(8-methyl-5-methylcarbamoyl-1-propyl-1,3,4,9-tetrahydropyrano[3,4-b]indol-1-yl)acetic acid

EXAMPLE 225

[8-methyl-5-(morpholine-4-carbonyl)-1-propyl-1,3,4,9-tetrahydropyrano[3,4-b]indol-1-yl]acetic acid

EXAMPLE 226

(5-carbamoyl-8-Methyl-1-propyl-1,3,4,9-tetrahydropyrano[3,4-b]indol-1-yl)acetic acid

EXAMPLE 227

(5-dimethylcarbamoyl-8-Methyl-1-propyl-1,3,4,9-tetrahydropyrano[3,4-b]indol-1-yl)acetic acid

EXAMPLE 228

(5-cyano-8-fluoro-3-methyl-1-propyl-1,3,4,9-tetrahydropyrano[3,4-b]indol-1-yl)acetic acid

EXAMPLE 229

(5,8-dichloro-4-methyl-1-propyl-1,3,4,9-tetrahydropyrano[3,4-b]indol-1-yl)acetic acid

EXAMPLE 230

(5,8-dichloro-4,4-dimethyl-1-propyl-1,3,4,9-tetrahydropyrano[3,4-b]indol-1-yl)acetic acid

EXAMPLE 231

(4-cyclobutyl-5,8-dichloro-1-propyl-1,3,4,9-tetrahydropyrano[3,4-b]indol-1-yl)acetic acid

EXAMPLE 232

(5,8-dichloro-9-methyl-1-propyl-1,3,4,9-tetrahydropyrano[3,4-b]indol-1-yl)acetic acid

EXAMPLE 233

(9-allyl-5,8-dichloro-1-propyl-1,3,4,9-tetrahydropyrano[3,4-b]indol-1-yl)acetic acid

EXAMPLE 234

(9-benzyl-5,8-dichloro-1-propyl-1,3,4,9-tetrahydropyrano[3,4-b]indol-1-yl)acetic acid

EXAMPLE 235

(5,6-dichloro-1-cyclobutyl-1,3,4,9-tetrahydropyrano[3,4-b]indol-1-yl)acetic acid

EXAMPLE 236

(5,6-dichloro-1-cyclopentyl-1,3,4,9-tetrahydropyrano[3,4-b]indol-1-yl)acetic acid

EXAMPLE 237

(5,6-Dichloro-1-methoxymethyl-1,3,4,9-tetrahydropyrano[3,4-b]indol-1-yl)acetic acid

EXAMPLE 238

[5,6-dichloro-1-(2-methoxyethyl)-1,3,4,9-tetrahydropyrano[3,4-b]indol-1-yl]acetic acid

EXAMPLE 239

[5,6-dichloro-1-(3,3,3-trifluoropropyl)-1,3,4,9-tetrahydropyrano[3,4-b]indol-1-yl]acetic acid

EXAMPLE 240

(6,7-dichloro-1-propyl-1,3,4,9-tetrahydropyrano[3,4-b]indol-1-yl)acetic acid

EXAMPLE 241

(6,7-dichloro-1-ethoxymethyl-1,3,4,9-tetrahydropyrano[3,4-b]indol-1-yl)acetic acid

EXAMPLE 242

(5,8-dichloro-1-methyl-1,3,4,9-tetrahydropyrano[3,4-b]indol-1-yl)acetic acid

EXAMPLE 243

(5,8-dichloro-1-ethyl-1,3,4,9-tetrahydropyrano[3,4-b]indol-1-yl)acetic acid

EXAMPLE 244

[5,8-dichloro-1-(3-cyanopropyl)-1,3,4,9-tetrahydropyrano[3,4-b]indol-1-yl]acetic acid

EXAMPLE 245

[5,8-dichloro-1-(3,3,3-trifluoropropyl)-1,3,4,9-tetrahydropyrano[3,4-b]indol-1-yl]acetic acid

EXAMPLE 246

(5,8-dichloro-1-methoxymethyl-1,3,4,9-tetrahydropyrano[3,4-b]indol-1-yl)acetic acid

EXAMPLE 247

[5,8-dichloro-1-(2-methoxyethyl)-1,3,4,9-tetrahydropyrano[3,4-b]indol-1-yl]acetic acid

EXAMPLE 248

(5,8-dichloro-1-ethoxymethyl-1,3,4,9-tetrahydropyrano[3,4-b]indol-1-yl)acetic acid

EXAMPLE 249

(5,8-dichloro-1-methylthiomethyl-1,3,4,9-tetrahydropyrano[3,4-b]indol-1-yl)acetic acid

EXAMPLE 250

(5,8-dichloro-1-ethylthiomethyl-1,3,4,9-tetrahydropyrano[3,4-b]indol-1-yl)acetic acid

EXAMPLE 251

[5,8-dichloro-1-(3-butenyl)-1,3,4,9-tetrahydropyrano[3,4-b]indol-1-yl]acetic acid

EXAMPLE 252

(5,8-dichloro-1-cyclopropyl-1,3,4,9-tetrahydropyrano[3,4-b]indol-1-yl)acetic acid

EXAMPLE 253

(5,8-dichloro-1-cyclobutyl-1,3,4,9-tetrahydropyrano[3,4-b]indol-1-yl)acetic acid

EXAMPLE 254

(5,8-dichloro-1-cyclopentyl-1,3,4,9-tetrahydropyrano[3,4-b]indol-1-yl)acetic acid

EXAMPLE 255

(5,8-dichloro-1-cyclohexyl-1,3,4,9-tetrahydropyrano[3,4-b]indol-1-yl)acetic acid

EXAMPLE 256

[5,8-dichloro-1-(1-methylpropyl)-1,3,4,9-tetrahydropyrano[3,4-b]indol-1-yl]acetic acid

EXAMPLE 257

(5,8-dichloro-1-cyclopropylmethyl-1,3,4,9-tetrahydropyrano[3,4-b]indol-1-yl)acetic acid

EXAMPLE 258

(5,8-dichloro-1-cyclopentylmethyl-1,3,4,9-tetrahydropyrano[3,4-b]indol-1-yl)acetic acid

EXAMPLE 259

(5-chloro-1-cyclobutyl-8-methyl-1,3,4,9-tetrahydropyrano[3,4-b]indol-1-yl)acetic acid

EXAMPLE 260

(5-chloro-8-methyl-1-propyl-1,3,4,9-tetrahydropyrano[3,4-b]indol-1-yl)acetic acid

EXAMPLE 261

(1R*,10S)-[5-chloro-8-methyl-1-(1-methylpropyl)-1,3,4,9-tetrahydropyrano[3,4-b]indol-1-yl]acetic acid

EXAMPLE 262

(8-chloro-5-methyl-1-propyl-1,3,4,9-tetrahydropyrano[3,4-b]indol-1-yl)acetic acid

EXAMPLE 263

[8-chloro-5-trifluoromethyl-1-(3,3,3-trifluoropropyl)-1,3,4,9-tetrahydropyrano[3,4-b]indol-1-yl ]acetic acid

EXAMPLE 264

(8-chloro-1-methoxymethyl-5-trifluoromethyl-1,3,4,9-tetrahydropyrano[3,4-b]indol-1-yl)acetic acid

EXAMPLE 265

[8-chloro-1-(2-methoxyethyl)-5-trifluoromethyl-1,3,4,9-tetrahydropyrano[3,4-b]indol-1-yl]acetic acid

EXAMPLE 266

(8-chloro-1-ethoxymethyl-5-trifluoromethyl-1,3,4,9-tetrahydropyrano[3,4-b]indol-1-yl)acetic acid

EXAMPLE 267

(8-chloro-1-cyclobutyl-5-trifluoromethyl-1,3,4,9-tetrahydropyrano[3,4-b]indol-1-yl)acetic acid

EXAMPLE 268

(8-fluoro-1-propyl-5-trifluoromethyl-1,3,4,9-tetrahydropyrano[3,4-b]indol-1-yl)acetic acid

EXAMPLE 269

(1-cyclobutyl-8-fluoro-5-trifluoromethyl-1,3,4,9-tetrahydropyrano[3,4-b]indol-1-yl)acetic acid

EXAMPLE 270

(1-cyclopentyl-8-fluoro-5-trifluoromethyl-1,3,4,9-tetrahydropyrano[3,4-b]indol-1-yl)acetic acid

EXAMPLE 271

[5,8-bis(trifluoromethyl)-1-propyl-1,3,4,9-tetrahydropyrano[3,4-b]indol-1-yl]acetic acid

EXAMPLE 272

(8-methyl-1-propyl-5-trifluoromethyl-1,3,4,9-tetrahydropyrano[3,4-b]indol-1-yl)acetic acid

EXAMPLE 273

(8-methyl-1-butyl-5-trifluoromethyl-1,3,4,9-tetrahydropyrano[3,4-b]indol-1-yl)acetic acid

EXAMPLE 274

(1-cyclopropyl-8-methyl-5-trifluoromethyl-1,3,4,9-tetrahydropyrano[3,4-b]indol-1-yl)acetic acid

EXAMPLE 275

(1-cyclobutyl-8-methyl-5-trifluoromethyl-1,3,4,9-tetrahydropyrano[3,4-b]indol-1-yl)acetic acid

EXAMPLE 276

(8-cyano-1-propyl-5-trifluoromethyl-1,3,4,9-tetrahydropyrano[3,4-b]indol-1-yl)acetic acid

EXAMPLE 277

(8-cyano-1-cyclobutyl-5-trifluoromethyl-1,3,4,9-tetrahydropyrano[3,4-b]indol-1-yl)acetic acid

EXAMPLE 278

(1R*,10S)-[8-aminocarbonyl-1-(1-methylpropyl)-5-trifluoromethyl-1,3,4,9-tetrahydropyrano[3,4-b]indol-1-yl]acetic acid

EXAMPLE 279

(1R*,10S)-[8-cyano-1-(1-methylpropyl)-5-trifluoromethyl-1,3,4,9-tetrahydropyrano[3,4-b]indol-1-yl]acetic acid

EXAMPLE 280

[5-cyano-8-methyl-1-(3,3,3-trifluoropropyl)-1,3,4,9-tetrahydropyrano[3,4-b]indol-1-yl]acetic acid

EXAMPLE 281

(5-cyano-1-methoxymethyl-8-methyl-1,3,4,9-tetrahydropyrano[3,4-b]indol-1-yl)acetic acid

EXAMPLE 282

(5-cyano-1-methylthiomethyl-8-methyl-1,3,4,9-tetrahydropyrano[3,4-b]indol-1-yl)acetic acid

EXAMPLE 283

(5-cyano-1-cyclopropyl-8-methyl-1,3,4,9-tetrahydropyrano[3,4-b]indol-1-yl)acetic acid

EXAMPLE 284

(5-cyano-1-cyclobutyl-8-methyl-1,3,4,9-tetrahydropyrano[3,4-b]indol-1-yl)acetic acid

EXAMPLE 285

(1R)-(5-cyano-1-cyclobutyl-8-methyl-1,3,4,9-tetrahydropyrano[3,4-b]indol-1-yl)acetic acid

EXAMPLE 286

(1S)-(5-cyano-1-cyclobutyl-8-methyl-1,3,4,9-tetrahydropyrano[3,4-b]indol-1-yl)acetic acid

EXAMPLE 287

(5-cyano-1-cyclopentyl-8-methyl-1,3,4,9-tetrahydropyrano[3,4-b]indol-1-yl)acetic acid

EXAMPLE 288

(5-cyano-1-cyclopentylmethyl-8-methyl-1,3,4,9-tetrahydropyrano[3,4-b]indol-1-yl)acetic acid

EXAMPLE 289

(1R*,10S*)-[5-cyano-8-methyl-1-(1-methylpropyl)-1,3,4,9-tetrahydropyrano[3,4-b]indol-1-yl]acetic acid

EXAMPLE 290

(1R*,10R*)-[5-cyano-8-methyl-1-(1-methylpropyl)-1,3,4,9-tetrahydropyrano[3,4-b]indol-1-yl]acetic acid

EXAMPLE 291

(1R*,10S)-[5-cyano-8-methyl-1-(1-methylpropyl)-1,3,4,9-tetrahydropyrano[3,4-b]indol-1-yl]acetic acid

EXAMPLE 292

(1R,10S)-[5-cyano-8-methyl-1-(1-methylpropyl)-1,3,4,9-tetrahydropyrano[3,4-b]indol-1-yl]acetic acid

EXAMPLE 293

(1S,10S)-[5-cyano-8-methyl-1-(1-methylpropyl)-1,3,4,9-tetrahydropyrano[3,4-b]indol-1-yl]acetic acid

EXAMPLE 294

[5-cyano-1-(1-ethylethyl)-8-methyl-1,3,4,9-tetrahydropyrano[3,4-b]indol-1-yl]acetic acid

EXAMPLE 295

(5-cyano-8-ethyl-1-propyl-1,3,4,9-tetrahydropyrano[3,4-b]indol-1-yl)acetic acid

EXAMPLE 296

(1-butyl-5-cyano-8-ethyl-1,3,4,9-tetrahydropyrano[3,4-b]indol-1-yl)acetic acid

EXAMPLE 297

[5-cyano-8-(1-methylethyl)-1-propyl-1,3,4,9-tetrahydropyrano[3,4-b]indol-1-yl]acetic acid

EXAMPLE 298

(8-methyl-5-nitro-1-propyl-1,3,4,9-tetrahydropyrano[3,4-b]indol-1-yl)acetic acid

EXAMPLE 299

(1-cyclobutyl-8-methyl-5-nitro-1,3,4,9-tetrahydropyrano[3,4-b]indol-1-yl)acetic acid

EXAMPLE 300

(1R*,10S)-[8-methyl-1-(1-methylpropyl)-5-nitro-1,3,4,9-tetrahydropyrano[3,4-b]indol-1-yl]acetic acid

EXAMPLE 301

[5-cyano-8-fluoro-1-(3,3,3-trifluoropropyl)-1,3,4,9-tetrahydropyrano[3,4-b]indol-1-yl]acetic acid

EXAMPLE 302

[1-(3-butenyl)-5-cyano-8-fluoro-1,3,4,9-tetrahydropyrano[3,4-b]indol-1-yl]acetic acid

EXAMPLE 303

(5-cyano-8-fluoro-1-methoxymethyl-1,3,4,9-tetrahydropyrano[3,4-b]indol-1-yl)acetic acid

EXAMPLE 304

[5-cyano-8-fluoro-1-(2-methoxyethyl)-1,3,4,9-tetrahydropyrano[3,4-b]indol-1-yl]acetic acid

EXAMPLE 305

(5-cyano-8-fluoro-1-methylthiomethyl-1,3,4,9-tetrahydropyrano[3,4-b]indol-1-yl)acetic acid

EXAMPLE 306

(5-cyano-1-cyclopropyl-8-fluoro-1,3,4,9-tetrahydropyrano[3,4-b]indol-1-yl)acetic acid

EXAMPLE 307

(5-cyano-1-cyclobutyl-8-fluoro-1,3,4,9-tetrahydropyrano[3,4-b]indol-1-yl)acetic acid

EXAMPLE 308

(5-cyano-1-cyclopentyl-8-fluoro-1,3,4,9-tetrahydropyrano[3,4-b]indol-1-yl)acetic acid

EXAMPLE 309

(5-cyano-1-cyclohexyl-8-fluoro-1,3,4,9-tetrahydropyrano[3,4-b]indol-1-yl)acetic acid

EXAMPLE 310

(5-cyano-1-cyclopentylmethyl-8-fluoro-1,3,4,9-tetrahydropyrano[3,4-b]indol-1-yl)acetic acid

EXAMPLE 311

[5-cyano-1-(1-ethylethyl)-8-fluoro-1,3,4,9-tetrahydropyrano[3,4-b]indol-1-yl]acetic acid

EXAMPLE 312

(1R*,10R*)-[5-cyano-8-fluoro-1-(1-methylpropyl)-1,3,4,9-tetrahydropyrano[3,4-b]indol-1-yl]acetic acid

EXAMPLE 313

(1R*,10S*)-[5-cyano-8-fluoro-1-(1-methylpropyl)-1,3,4,9-tetrahydropyrano[3,4-b]indol-1-yl]acetic acid

EXAMPLE 314

(1R*,10S)-[5-cyano-8-fluoro-1-(1-methylpropyl)-1,3,4,9-tetrahydropyrano[3,4-b]indol-1-yl]acetic acid

EXAMPLE 315

(1R,10S)-[5-cyano-8-fluoro-1-(1-methylpropyl)-1,3,4,9-tetrahydropyrano[3,4-b]indol-1-yl]acetic acid

EXAMPLE 316

(1S,10S)-[5-cyano-8-fluoro-1-(1-methylpropyl)-1,3,4,9-tetrahydropyrano[3,4-b]indol-1-yl]acetic acid

EXAMPLE 317

(5-cyano-1-cyclobutyl-6-fluoro-8-methyl-1,3,4,9-tetrahydropyrano[3,4-b]indol-1-yl)acetic acid

EXAMPLE 318

(1R*,10S)-[5-cyano-6-fluoro-8-methyl-1-(1-methylpropyl)-1,3,4,9-tetrahydropyrano[3,4-b]indol-1-yl]acetic acid

EXAMPLE 319

(1R,10S)-[5-cyano-6-fluoro-8-methyl-1-(1-methylpropyl)-1,3,4,9-tetrahydropyrano[3,4-b]indol-1-yl]acetic acid

EXAMPLE 320

(1S,10S)-[5-cyano-6-fluoro-8-methyl-1-(1-methylpropyl)-1,3,4,9tetrahydropyrano[3,4-b]indol-1-yl]acetic acid

EXAMPLE 321

(8-chloro-5-cyano-1-propyl-1,3,4,9-tetrahydropyrano[3,4-b]indol-1-yl)acetic acid

EXAMPLE 322

(1R)-(8-chloro-5-cyano-1-propyl-1,3,4,9-tetrahydropyrano[3,4-b]indol-1-yl)acetic acid

EXAMPLE 323

(1S)-(8-chloro-5-cyano-1-propyl-1,3,4,9-tetrahydropyrano[3,4-b]indol-1-yl)acetic acid

EXAMPLE 324

(1R*,10S)-[8-chloro-5-cyano-1-(1-methylethyl)-1,3,4,9-tetrahydropyrano[3,4-b]indol-1-yl]acetic acid

EXAMPLE 325

(1R,10S)-[8-chloro-5-cyano-1-(1-methylethyl)-1,3,4,9-tetrahydropyrano[3,4-b]indol-1-yl]acetic acid

EXAMPLE 326

(1S,10S)-[8-chloro-5-cyano-1-(1-methylethyl)-1,3,4,9-tetrahydropyrano[3,4-b]indol-1-yl]acetic acid

EXAMPLE 327

(8-chloro-5-cyano-1-cyclobutyl-1,3,4,9-tetrahydro-pyrano[3,4-b]indol-1-yl)acetic acid

EXAMPLE 328

(5,6-dichloro-1-propyl-1,3,4,9-tetrahydropyrano[3,4-b]indol-1-yl)carboxylic acid

EXAMPLE 329

(5,8-dichloro-1-propyl-1,3,4,9-tetrahydropyrano[3,4-b]indol-1-yl)carboxylic acid

EXAMPLE 330

(5-chloro-8-methyl-1-propyl-1,3,4,9-tetrahydropyrano[3,4-b]indol-1-yl)carboxylic acid

EXAMPLE 331

(8-chloro-5-trifluoromethyl-1-propyl-1,3,4,9-tetrahydropyrano[3,4-b]indol-1-yl)carboxylic acid

EXAMPLE 332

(8-fluoro-5-trifluoromethyl-1-propyl-1,3,4,9-tetrahydropyrano[3,4-b]indol-1-yl)carboxylic acid

EXAMPLE 333

(5-trifluoromethyl-8-methyl-1-propyl-1,3,4,9-tetrahydropyrano[3,4-b]indol-1-yl)carboxylic acid

EXAMPLE 334

(5-cyano-8-methyl-1-propyl-1,3,4,9-tetrahydropyrano[3,4-b]indol-1-yl)carboxylic acid

EXAMPLE 335

(1R*,10S*)-[5-cyano-8-methyl-(1-methylpropyl)-1,3,4,9-tetrahydropyrano[3,4-b]indol-1-yl]carboxylic acid

EXAMPLE 336

(1R*,10R*)-[5-cyano-8-methyl-1-(1-methylpropyl)-1,3,4,9-tetrahydropyrano[3,4-b]indol-1-yl]carboxylic acid

EXAMPLE 337

[5-cyano-8-methyl-1-(3-methylpropyl)-1,3,4,9-tetrahydropyrano[3,4-b]indol-1-yl]carboxylic acid

EXAMPLE 338

(5-cyano-1-cyclobutyl-8-methyl-1,3,4,9-tetrahydro-pyrano[3,4-b]indol-1-yl)carboxylic acid

EXAMPLE 339

(5-cyano-6-fluoro-8-methyl-1-propyl-1,3,4,9-tetrahydropyrano[3,4-b]indol-1-yl)carboxylic acid

EXAMPLE 340

(5-cyano-8-ethyl-1-propyl-1,3,4,9-tetrahydropyrano[3,4-b]indol-1-yl)carboxylic acid

EXAMPLE 341

(8-chloro-5-cyano-1-propyl-1,3,4,9-tetrahydropyrano[3,4-b]indol-1-yl)carboxylic acid

EXAMPLE 342

(5-cyano-8-fluoro-1-propyl-1,3,4,9-tetrahydropyrano[3,4-b]indol-1-yl)carboxylic acid

EXAMPLE 343

(1R)-(5-cyano-8-fluoro-1-propyl-1,3,4,9-tetrahydropyrano[3,4-b]-indol 1-yl)carboxylic acid

EXAMPLE 344

(1S)-(5-cyano-8-fluoro-1-propyl-1,3,4,9-tetrahydropyrano[3,4-b]indol-1-yl)carboxylic acid

EXAMPLE 345

(1-butyl-5-cyano-8-fluoro-1,3,4,9-tetrahydropyrano[3,4-b]indol-1-yl)carboxylic acid

EXAMPLE 346

[1-(3-butenyl)-5-cyano-8-fluoro-1,3,4,9-tetrahydropyrano[3,4-b]indol-1-yl]carboxylic acid

EXAMPLE 347

[5-cyano-8-fluoro-1-(3-methylpropyl)-1,3,4,9-tetrahydropyrano[3,4-b]indol 1-yl]carboxylic acid

EXAMPLE 348

(1R*,10S*)-[5-cyano-8-fluoro-1-(1-methylpropyl)-1,3,4,9-tetrahydropyrano[3,4-b]indol-1-yl]carboxylic acid

EXAMPLE 349

(1R*,10R*)-[5-cyano-8-fluoro-1-(1-methylpropyl)-1,3,4,9-tetrahydropyrano[3,4-b]indol--1-yl]carboxylic acid

EXAMPLE 350

(5-cyano-1-cyclopentyl-8-fluoro-1,3,4,9-tetrahydro-pyrano[3,4-b]indol-1-yl)carboxylic acid

EXAMPLE 351

(5-cyano-1-cyclohexyl-8-fluoro-1,3,4,9-tetrahydro-pyrano[3,4-b]indol-1-yl)carboxylic acid

EXAMPLE 352

(8-fluoro-5-nitro-1-propyl-1,3,4,9-tetrahydropyrano[3,4-b]indol-1-yl)carboxylic acid

EXAMPLE 353

1-carboxymethyl-5-cyano-8-methyl-1-propyl-1,3,4,9 tetrahydro-pyrano[3,4-b]indole-7-carboxylic acid

EXAMPLE 354

(5-cyano-8-methyl-1-propyl-7-propylcarbamoyl-1,3,4,9-tetrahydro-pyrano[3,4-b]indol-1-yl)-acetic acid

EXAMPLE 355

(5-cyano-7-isopropylcarbamoyl-8-methyl-1-propyl-1,3,4,9-tetrahydro-pyrano[3,4-b]indol-1-yl)-acetic acid

EXAMPLE 356

[5-cyano-7-(4,4-dimethyl-butylcarbamoyl)-8-methyl-1-propyl-1,3,4,9-tetrahydro-pyrano[3,4-b]indol-1yl]-acetic acid

EXAMPLE 357

(5-cyano-8-methyl-7-methylcarbamoyl-1-propyl-1,3,4,9-tetrahydro-pyrano[3,4-b]indol-1-yl)-acetic acid

EXAMPLE 358

(5-cyano-8-methyl-7-dimethylcarbamoyl-1-propyl-1,3,4,9-tetrahydro-pyrano[3,4-b]indol-1-yl)-acetic acid

EXAMPLE 359

(5-cyano-8-methyl-7-propoxy-1-propyl-1,3,4,9-tetrahydro-pyrano[3,4-b]indol-1-yl)-acetic acid

EXAMPLE 360

(1R)-(5-cyano-8-methyl-7-propoxy-1-propyl-1,3,4,9-tetrahydro-pyrano[3,4-b]indol-1-yl)-acetic acid

EXAMPLE 361

(1S)-(5-cyano-8-methyl-7-propoxy-1-propyl-1,3,4,9-tetrahydro-pyrano[3,4-b]indol-1-yl)-acetic acid

EXAMPLE 362

(5-cyano-7-ethoxy-8-methyl-1-propyl-1,3,4,9-tetrahydro-pyrano[3,4-b]indol-1-yl)-acetic acid

EXAMPLE 363

(5-cyano-7-methoxy-8-methyl-1-propyl-1,3,4,9-tetrahydro-pyrano[3,4-b]indol-1-yl)-acetic acid

EXAMPLE 364

(5-cyano-7-isopropoxy-8-methyl-1-propyl-1,3,4,9-tetrahydro-pyrano[3,4-b]indol-1-yl)-acetic acid

EXAMPLE 365

(7-butoxy-5-cyano-8-methyl-1-propyl-1,3,4,9-tetrahydro-pyrano[3,4-b]indol-1-yl)-acetic acid

EXAMPLE 366

[5-cyano-7-(3,3-dimethyl-butoxy)-8-methyl-1-propy-1,3,4,9-tetrahydro-pyrano[3,4-b]indol-1-yl]-acetic acid

EXAMPLE 367

[5-cyano-7-(3-fluoro-benzyloxy)-8-methyl-1-propyl-1,3,4,9-tetrahydro-pyrano[3,4-b]indol-1-yl]acetic acid

EXAMPLE 368

(7-benzyloxy-5-cyano-8-methyl-1-propyl-1,3,4,9-tetrahydro-pyrano[3,4-b]indol-1-yl)-acetic acid

EXAMPLE 369

[5-cyano-7-(2-fluoro-ethoxy)-8-methyl-1-propyl-1,3,4,9-tetrahydro-pyrano[3,4-b]indol-1-yl]acetic acid

EXAMPLE 370

[5-cyano-7-(3-fluoro-propoxy)-8-methyl-1-propyl-1,3,4,9-tetrahydro-pyrano[3,4-b]indol-1-yl]acetic acid

What is claimed is:

1. A method of treating a Hepatitis C viral infection in a mammal comprising providing the mammal with an effective amount of a compound of a formula:

wherein:

$R_1$ is H, a straight chain alkyl of 1 to 8 carbon atoms, a branched alkyl of 3 to 12 carbon atoms, a cycloalkyl of 3 to 12 carbon atoms, an alkenyl of 2 to 7 carbon atoms, an alkynyl of 2 to 7 carbon atoms, or an arylalkyl or an alkylaryl of 7 to 12 carbon atoms;

$R_2$ is H, a straight chain alkyl of 1 to 12 carbon atoms, a branched alkyl of 3 to 12 carbon atoms, a cycloalkyl of 3 to 12 carbon atoms, an alkenyl of 2 to 7 carbon atoms, an alkynyl of 2 to 7 carbon atoms, an alkoxyalkyl of 2 to 12 carbon atoms, an arylalkyl or alkylaryl of 7 to 12 carbon atoms, a cyanoalkyl of 1 to 8 carbon atoms, an alkylthioalkyl of 2 to 16 carbon atoms, a cycloalkylalkyl of 4 to 24 carbon atoms, a substituted or unsubstituted aryl, or a heteroaryl, or with the proviso that when Y is $CH_2$ or $CH_2CH_2$, $R^2$ and Y together form a cycloalkyl of 3 to 8 carbon atoms;

$R_3$—$R_6$ are independently H, a straight chain alkyl of 1 to 8 carbon atoms, a branched alkyl of 3 to 12 carbon atoms, a cycloalkyl of 3 to 12 carbon atoms, an alkenyl of 2 to 7 carbon atoms, a substituted or unsubstituted aryl, furanylmethyl, arylalkyl or alkylaryl of 7 to 12 carbon atoms, alkynyl of 2 to 7 carbon atoms, or $R_5$ and $R_6$ together with the ring carbon atom to which they are attached form a carbonyl group;

$R_7$—$R_{10}$ are independently H, a straight chain alkyl of 1 to 8 carbon atoms, a branched alkyl of 3 to 12 carbons atoms, a cycloalkyl of 3 to 12 carbon atoms, an alkenyl of 2 to 7 carbon atoms, a substituted or unsubstituted aryl, a substituted or unsubstituted heteroaryl, furanylmethyl, arylalkyl or alkylaryl of 7 to 12 carbon atoms, alkynyl of 2 to 7 carbon atoms, phenylalkynyl, alkoxy of 1 to 8 carbon atoms, arylalkoxy of 7 to 12 carbon atoms, fluoroalkoxy of 1 to 12 carbon atoms, alkylthio of 1 to 8 carbon atoms, trifluoromethoxy, trifluoroethoxy, trifluoromethylthio, trifluoroethylthio, acyl of 1 to 6 carbon atoms, COOH, COO-alkyl, $CONR^{11}R^{12}$, F, Cl, Br, I, CN, $CF_3$, $NO_2$, alkylsulfinyl of 1 to 8 carbon atoms, alkylsulfonyl of 1 to 6 carbon atoms, pyrrolidinyl, or thiazolidinyl;

$R_{11}$—$R_{12}$ are independently H, straight chain alkyl of 1 to 8 carbon atoms, branched alkyl of 3 to 12 carbon atoms, cycloalkyl of 3 to 12 carbon atoms, a substituted or unsubstituted aryl or heteroaryl;

Y is a bond, $CH_2$, or $CH_2CH_2$; or a crystalline form or a pharmaceutically acceptable salt thereof.

2. A method of treating a Hepatitis C viral infection in a mammal comprising providing the mammal with an effective amount of a compound of a formula:

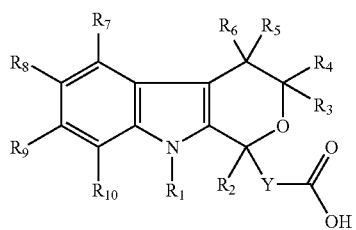

wherein:

$R_1$ is H, a straight chain alkyl of 1 to 6 carbon atoms, a branched alkyl of 3 to 10 carbon atoms, a cycloalkyl of 3 to 10 carbon atoms, an alkenyl of 2 to 7 carbon atoms, an alkynyl of 2 to 7 carbon atoms, or an arylalkyl of 7 to 12 carbon atoms;

$R_2$ is H, a straight chain alkyl of 1 to 12 carbon atoms, a branched alkyl of 3 to 10 carbon atoms, a cycloalkyl of 3 to 10 carbon atoms, an alkenyl of 2 to 7 carbon atoms, an alkynyl of 2 to 7 carbon atoms, an alkoxyalkyl of 2 to 12 carbon atoms, an arylalkyl of 7 to 12 carbon atoms, an unsubstituted aryl or an aryl substituted with one to four groups, or heteroaryl;

$R_3$—$R_6$ are independently H, a straight chain alkyl of 1 to 6 carbon atoms, a branched alkyl of 3 to 10 carbons atoms, a cycloalkyl of 3 to 10 carbon atoms, an alkenyl of 2 to 7 carbon atoms, an unsubstituted aryl or an aryl substituted with one to four groups, furanylmethyl, an arylalkyl of 7 to 12 carbon atoms, an alkynyl of 2 to 7 carbon atoms, or $R_5$ and $R_6$ together with the ring carbon atom to which they are attached form a carbonyl group;

$R_7$—$R_{10}$ are independently H, a straight chain alkyl of 1 to 6 carbon atoms, a branched alkyl of 3 to 10 carbons atoms, a cycloalkyl of 3 to 10 carbon atoms, an alkenyl of 2 to 7 carbon atoms, an unsubstituted aryl or an aryl substituted with one to four groups, an unsubstituted heteroaryl or a heteroaryl substituted with one to three groups, furanylmethyl, an arylalkyl of 7 to 12 carbon atoms, an alkynyl of 2 to 7 carbon atoms, phenylalkynyl, an alkoxy of 1 to 6 carbon atoms, an arylalkoxy of 7 to 12 carbon atoms, a fluoroalkoxy of 1 to 12 carbon atoms, an alkylthio of 1 to 6 carbon atoms, trifluoromethoxy, trifluoroethoxy, trifluoromethylthio, trifluoroethylthio, an acyl of 1 to 6 carbon atoms, a carboxy group, $CONR_{11}R_{12}$, F, Cl, Br, I, CN, $CF_3$, $NO_2$, an alkylsulfinyl of 1 to 6 carbon atoms, an alkylsulfonyl of 1 to 6 carbon atoms;

$R_{11}$—$R_{12}$ are independently H, a straight chain alkyl of 1 to 6 carbon atoms, a branched alkyl of 3 to 10 carbon atoms, a cycloalkyl of 3 to 10 carbon atoms, an aryl substituted with one to four groups, an unsubstituted heteroaryl or a heteroaryl substituted with one to three groups;

Y is $CH_2$, or $CH_2CH_2$; or a crystalline form or a pharmaceutically acceptable salt thereof.

3. The method of claim 1 wherein the compound is selected from:

(5-cyano-6-fluoro-8-methyl-1-propyl-1,3,4,9-tetrahydropyrano[3,4-b]indol-1-yl)acetic acid;

[(R)-5-cyano-6-fluoro-8-methyl-1-propyl-1,3,4,9-tetrahydropyrano[3,4-b]indol-1-yl]acetic acid; and

[(S)-5-cyano-6-fluoro-8-methyl-1-propyl-1,3,4,9-tetrahydropyrano[3,4-b]indol-1-yl]acetic acid.

4. The method of claim 1 wherein the compound is selected from:

(5-cyano-1-ethyl-6,8-difluoro-1,3,4,9-tetrahydropyrano[3,4-b]indol-1-yl)acetic acid;

(5-cyano-6,8-difluoro-1-propyl-1,3,4,9-tetrahydropyrano[3,4-b]indol-1-yl)acetic acid;

(1-butyl-5-cyano-6,8-difluoro-1,3,4,9-tetrahydropyrano[3,4-b]indol-1-yl)acetic acid;

[5-cyano-6,8-difluoro-1-(3-furyl)-1,3,4,9-tetrahydropyrano[3,4-b]indol-1-yl]acetic acid;

(5-cyano-6,8-difluoro-1-isopropyl-1,3,4,9-tetrahydropyrano[3,4-b]indol-1-yl)acetic acid;

5-bromo-6-fluoro-1,8-dimethyl-1,3,4,9-tetrahydropyrano[3,4-b]indol-1-yl)acetic acid;

(5-bromo-1-ethyl-6-fluoro-8-methyl-1,3,4,9-tetrahydropyrano[3,4-b]indol-1-yl)acetic acid;

(5-bromo-6-fluoro-8-methyl-1-propyl-1,3,4,9-tetrahydropyrano[3,4-b]indol-1-yl)acetic acid;

(5-bromo-6-fluoro-1-isopropyl-8-methyl-1,3,4,9-tetrahydropyrano[3,4-b]indol-1-yl)acetic acid;

(5-bromo-1-butyl-6-fluoro-8-methyl-1,3,4,9-tetrahydropyrano[3,4-b]indol-1-yl)acetic acid; and 4-[5-bromo-1-(carboxymethyl)-6-fluoro-8-methyl-1,3,4,9-tetrahydropyrano[3,4-b]indol-1-yl]benzoic acid.

5. The method of claim 1 wherein the compound is selected from:
- (5-cyano-8-fluoro-1,6-dimethyl-1,3,4,9-tetrahydropyrano[3,4-b]indol-1-yl)acetic acid;
- (5-cyano-1-ethyl-8-fluoro-6-methyl-1,3,4,9-tetrahydropyrano[3,4-b]indol-1-yl)acetic acid;
- (5-cyano-8-fluoro-6-methyl-1-propyl-1,3,4,9-tetrahydropyrano[3,4-b]indol-1-yl)acetic acid;
- (5-cyano-8-fluoro-1-isopropyl-6-methyl-1,3,4,9-tetrahydropyrano[3,4-b]indol-1-yl)acetic acid; and
- {5-cyano-8-fluoro-6-methyl-1-[(3E)-pent-3-enyl]-1,3,4,9-tetrahydropyrano[3,4-b]indol-1-yl}acetic acid.

6. The method of claim 1 wherein the compound is selected from:
- (8-Methyl-5-methylcarbamoyl-1-propyl-1,3,4,9-tetrahydropyrano[3,4-b]indol-1-yl)acetic acid;
- [8-Methyl-5-(morpholine-4-carbonyl)-1-propyl-1,3,4,9-tetrahydropyrano[3,4-b]indol-1-yl)acetic acid;
- (5-Carbamoyl-8-Methyl-1-propyl-1,3,4,9-tetrahydropyrano[3,4-b]indol-1-yl)acetic acid;
- (5-Dimethylcarbamoyl-8-Methyl-1-propyl-1,3,4,9-tetrahydropyrano[3,4-b]indol-1-yl)acetic acid;
- (5-cyano-8-fluoro-3-methyl-1-propyl-1,3,4,9-tetrahydropyrano[3,4-b]indol-1-yl)acetic acid;
- (5,8-Dichloro-4-methyl-1-propyl-1,3,4,9-tetrahydropyrano[3,4-b]indol-1-yl)acetic acid;
- (5,8-Dichloro-4,4-dimethyl-1-propyl-1,3,4,9-tetrahydropyrano[3,4-b]indol-1-yl)acetic acid;
- (4-Cyclobutyl-5,8-dichloro-1-propyl-1,3,4,9-tetrahydropyrano[3,4-b]indol-1-yl)acetic acid;
- (5,8-Dichloro-9-methyl-1-propyl-1,3,4,9-tetrahydropyrano[3,4-b]indol-1-yl)acetic acid;
- (9-Allyl-5,8-dichloro-1-propyl-1,3,4,9-tetrahydropyrano[3,4-b]indol-1-yl)acetic acid; and
- (9-Benzyl-5,8-dichloro-1-propyl-1,3,4,9-tetrahydropyrano[3,4-b]indol-1-yl)acetic acid.

7. The method of claim 1 wherein the compound is selected from:
- (5,8-Dichloro-4,4-dimethyl-1-propyl-1,3,4,9-tetrahydropyrano[3,4-b]indol-1-yl)acetic acid;
- (4-Cyclobutyl-5,8-dichloro-1-propyl-1,3,4,9-tetrahydropyrano[3,4-b]indol-1-yl)acetic acid;
- (5,8-Dichloro-9-methyl-1-propyl-1,3,4,9-tetrahydropyrano[3,4-b]indol-1-yl)acetic acid;
- (9-Allyl-5,8-dichloro-1-propyl-1,3,4,9-tetrahydropyrano[3,4-b]indol-1-yl)acetic acid;
- (9-Benzyl-5,8-dichloro-1-propyl-1,3,4,9-tetrahydropyrano[3,4-b]indol-1-yl)acetic acid;
- (5,6-Dichloro-1-cyclobutyl-1,3,4,9-tetrahydropyrano[3,4-b]indol-1-yl)acetic acid;
- (5,6-Dichloro-1-cyclopentyl-1,3,4,9-tetrahydropyrano[3,4-b]indol-1-yl)acetic acid;
- (5,6-Dichloro-1-methoxymethyl-1,3,4,9-tetrahydropyrano[3,4-b]indol-1-yl)acetic acid;
- [5,6-Dichloro-1-(2-methoxyethyl)-1,3,4,9-tetrahydropyrano[3,4-b]indol-1-yl]acetic acid;
- [5,6-Dichloro-1-(3,3,3-trifluoropropyl)-1,3,4,9-tetrahydropyrano[3,4-b]indol-1-yl]acetic acid;
- (6,7-Dichloro-1-propyl-1,3,4,9-tetrahydropyrano[3,4-b]indol-1-yl)acetic acid;
- (6,7-Dichloro-1-ethoxymethyl-1,3,4,9-tetrahydropyrano[3,4-b]indol-1-yl)acetic acid;
- (5,8-Dichloro-1-methyl-1,3,4,9-tetrahydropyrano[3,4-b]indol-1-yl)acetic acid;
- (5,8-Dichloro-1-ethyl-1,3,4,9-tetrahydropyrano[3,4-b]indol-1-yl)acetic acid;
- [5,8-Dichloro-1-(3-cyanopropyl)-1,3,4,9-tetrahydropyrano[3,4-b]indol-1-yl)acetic acid;
- [5,8-Dichloro-1-(3,3,3-trifluoropropyl)-1,3,4,9-tetrahydropyrano[3,4-b]indol-1-yl]acetic acid;
- (5,8-Dichloro-1-methoxymethyl-1,3,4,9-tetrahydropyrano[3,4-b]indol-1-yl)acetic acid;
- [5,8-Dichloro-1-(2-methoxyethyl)-1,3,4,9-tetrahydropyrano[3,4-b]indol-1-yl]acetic acid;
- (5,8-Dichloro-1-ethoxymethyl-1,3,4,9-tetrahydropyrano[3,4-b]indol-1-yl)acetic acid;
- (5,8-Dichloro-1-methylthiomethyl-1,3,4,9-tetrahydropyrano[3,4-b]indol-1-yl)acetic acid;
- (5,8-Dichloro-1-ethylthiomethyl-1,3,4,9-tetrahydropyrano[3,4-b]indol-1-yl)acetic acid;
- [5,8-Dichloro-1-(3-butenyl)-1,3,4,9-tetrahydropyrano[3,4-b]indol-1-yl]acetic acid;
- (5,8-Dichloro-1-cyclopropyl-1,3,4,9-tetrahydropyrano[3,4-b]indol-1-yl)acetic acid
- (5,8-Dichloro-1-cyclobutyl-1,3,4,9-tetrahydropyrano[3,4-b]indol-1-yl)acetic acid;
- (5,8-Dichloro-1-cyclopentyl-1,3,4,9-tetrahydropyrano[3,4-b]indol-1-yl)acetic acid;
- (5,8-Dichloro-1-cyclohexyl-1,3,4,9-tetrahydropyrano[3,4-b]indol-1-yl)acetic acid;
- [5,8-Dichloro-1-(1-methylpropyl)-1,3,4,9-tetrahydropyrano[3,4-b]indol-1-yl]acetic acid;
- (5,8-Dichloro-1-cyclopropylmethyl-1,3,4,9-tetrahydropyrano[3,4-b]indol-1-yl)acetic acid;
- (5,8-Dichloro-1-cyclopentylmethyl-1,3,4,9-tetrahydropyrano[3,4-b]indol-1-yl)acetic acid;
- (5-Chloro-1-cyclobutyl-8-methyl-1,3,4,9-tetrahydropyrano[3,4-b]indol-1-yl)acetic acid;
- (5-Chloro-8-methyl-1-propyl-1,3,4,9-tetrahydropyrano[3,4-b]indol-1-yl)acetic acid;
- (1R*,10S)-[5-Chloro-8-methyl-1-(1-methylpropyl)-1,3,4,9-tetrahydropyrano[3,4-b]indol-1-yl]acetic acid;
- (8-Chloro-5-methyl-1-propyl-1,3,4,9-tetrahydropyrano[3,4-b]indol-1-yl)acetic acid;
- [8-Chloro-5-trifluoromethyl-1-(3,3,3-trifluoropropyl)-1,3,4,9-tetrahydropyrano[3,4-b]indol-1-yl]acetic acid;
- (8-Chloro-1-methoxymethyl-5-trifluoromethyl-1,3,4,9-tetrahydropyrano[3,4-b]indol-1-yl)acetic acid;
- [8-Chloro-1-(2-methoxyethyl)-5-trifluoromethyl-1,3,4,9-tetrahydropyrano[3,4-b]indol-1-yl]acetic acid;
- (8-Chloro-1-ethoxymethyl-5-trifluoromethyl-1,3,4,9-tetrahydropyrano[3,4-b]indol-1-yl)acetic acid;
- (8-Chloro-1-cyclobutyl-5-trifluoromethyl-1,3,4,9-tetrahydropyrano[3,4-b]indol-1-yl)acetic acid;
- (8-Fluoro-1-propyl-5-trifluoromethyl-1,3,4,9-tetrahydropyrano[3,4-b]indol-1-yl)acetic acid
- (1-Cyclobutyl-8-fluoro-5-trifluoromethyl-1,3,4,9-tetrahydropyrano[3,4-b]indol-1-yl)acetic acid;
- (1-Cyclopentyl-8-fluoro-5-trifluoromethyl -1,3,4,9-tetrahydropyrano[3,4-b]indol-1-yl)acetic acid;
- [5,8-bis(trifluoromethyl)-1-propyl-1,3,4,9-tetrahydropyrano[3,4-b]indol-1-yl]acetic acid;
- (8-Methyl-1-propyl-5-trifluoromethyl-1,3,4,9-tetrahydropyrano[3,4-b]indol-1-yl)acetic acid;
- (8-Methyl-1-butyl-5-trifluoromethyl-1,3,4,9-tetrahydropyrano[3,4-b]indol-1-yl)acetic acid;
- (1-Cyclopropyl-8-methyl-5-trifluoromethyl-1,3,4,9-tetrahydropyrano[3,4-b]indol-1-yl)acetic acid;
- (1-Cyclobutyl-8-methyl-5-trifluoromethyl -1,3,4,9-tetrahydropyrano[3,4-b]indol-1-yl)acetic acid;
- (8-Cyano-1-propyl-5-trifluoromethyl-1,3,4,9-tetrahydropyrano[3,4-b]indol-1-yl)acetic acid;

(8-Cyano-1-cyclobutyl-5-trifluoromethyl-1,3,4,9-tetrahydropyrano[3,4-b]indol-1-yl)acetic acid;
(1R*,10S)-[8-Aminocarbonyl-1-(1-methylpropyl)-5-trifluoromethyl-1,3,4,9-tetrahydropyrano[3,4-b]indol-1-yl]acetic acid;
(1R*,10S)-[8-Cyano-1-(1-methylpropyl)-5-trifluoromethyl-1,3,4,9-tetrahydropyrano[3,4-b]indol-1-yl]acetic acid;
[5-Cyano-8-methyl-1-(3,3,3-trifluoropropyl)-1,3,4,9-tetrahydropyrano[3,4-b]indol-1-yl]acetic acid;
(5-Cyano-1-methoxymethyl-8-methyl-1,3,4,9-tetrahydropyrano[3,4-b]indol-1-yl)acetic acid;
(5-Cyano-1-methylthiomethyl-8-methyl-1,3,4,9-tetrahydropyrano[3,4-b]indol-1-yl)acetic acid;
(5-Cyano-1-cyclopropyl-8-methyl-1,3,4,9-tetrahydropyrano[3,4-b]indol-1-yl)acetic acid;
(5-Cyano-1-cyclobutyl-8-methyl-1,3,4,9-tetrahydropyrano[3,4-b]indol-1-yl)acetic acid;
(1R)-(5-Cyano-1-cyclobutyl-8-methyl-1,3,4,9-tetrahydropyrano[3,4-b]indol-1-yl)acetic acid;
(1S)-(5-Cyano-1-cyclobutyl-8-methyl-1,3,4,9-tetrahydropyrano[3,4-b]indol-1-yl)acetic acid;
(5-Cyano-1-cyclopentyl-8-methyl-1,3,4,9-tetrahydropyrano[3,4-b]indol-1-yl)acetic acid;
(5-Cyano-1-cyclopentylmethyl-8-methyl-1,3,4,9-tetrahydropyrano[3,4-b]indol-1-yl)acetic acid;
(1R*,10S*)-[5-Cyano-8-methyl-1-(1-methylpropyl)-1,3,4,9-tetrahydropyrano[3,4-b]indol-1-yl]acetic acid;
(1R*,10S*)-[5-Cyano-8-methyl-1-(1-methylpropyl)-1,3,4,9-tetrahydropyrano[3,4-b]indol-1-yl]acetic acid;
(1R*,10S)-[5-Cyano-8-methyl-1-(1-methylpropyl)-1,3,4,9-tetrahydropyrano[3,4-b]indol-1-y1]acetic acid;
(1R,10S)-[5-Cyano-8-methyl-1-(1-methylpropyl)-1,3,4,9-tetrahydropyrano[3,4-b]indol-1-yl]acetic acid;
(1S,10S)-[5-Cyano-8-methyl-1-(1-methylpropyl)-1,3,4,9-tetrahydropyrano[3,4-b]indol-1-yl]acetic acid;
[5-Cyano-1-(1-ethylethyl)-8-methyl-1,3,4,9-tetrahydropyrano[3,4-b]indol-1-yl]acetic acid;
(5-Cyano-8-ethyl-1-propyl-1,3,4,9-tetrahydropyrano[3,4-b]indol-1-yl)acetic acid;
(1-Butyl-5-cyano-8-ethyl-1,3,4,9-tetrahydropyrano[3,4-b]indol-1-yl)acetic acid;
[5-Cyano-8-(1-methylethyl)-1-propyl-1,3,4,9-tetrahydropyrano[3,4-b]indol-1-yl]acetic acid;
(8-Methyl-5-nitro-1-propyl-1,3,4,9-tetrahydropyrano[3,4-b]indol-1-yl)acetic acid;
(1-Cyclobutyl-8-methyl-5-nitro-1,3,4,9-tetrahydropyrano[3,4-b]indol-1-yl]acetic acid;
(1R*,10S)-[8-Methyl-1-(1-methylpropyl)-5-nitro-1,3,4,9-tetrahydropyrano[3,4-b]indol-1-yl]acetic acid;
[5-Cyano-8-fluoro-1-(3,3,3-trifluoropropyl)-1,3,4,9-tetrahydropyrano[3,4-b]indol-1-yl]acetic acid;
[1-(3-butenyl)-5-cyano-8-fluoro-1,3,4,9-tetrahydropyrano[3,4-b]indol-1-yl]acetic acid;
(5-Cyano-8-fluoro-1-methoxymethyl-1,3,4,9-tetrahydropyrano[3,4-b]indol-1-yl)acetic acid;
[5-Cyano-8-fluoro-1-(2-methoxyethyl)-1,3,4,9-tetrahydropyrano[3,4-b]indol-1-yl]acetic acid;
(5-Cyano-8-fluoro-1-methylthiomethyl-1,3,4,9-tetrahydropyrano[3,4-b]indol-1-yl)acetic acid;
(5-Cyano-1-cyclopropyl-8-fluoro-1,3,4,9-tetrahydropyrano[3,4-b]indol-1-yl)acetic acid;
(5-Cyano-1-cyclobutyl-8-fluoro-1,3,4,9-tetrahydropyrano[3,4-b]indol-1-yl)acetic acid;
(5-Cyano-1-cyclopentyl-8-fluoro-1,3,4,9-tetrahydropyrano[3,4-b]indol-1-yl)acetic acid;
(5-Cyano-1-cyclohexyl-8-fluoro-1,3,4,9-tetrahydropyrano[3,4-b]indol-1-yl)acetic acid;
(5-Cyano-1-cyclopentylmethyl-8-fluoro-1,3,4,9-tetrahydropyrano[3,4-b]indol-1-yl)acetic acid;
[5-Cyano-1-(1-ethylethyl)-8-fluoro-1,3,4,9-tetrahydropyrano[3,4-b]indol-1-yl]acetic acid;
(1R*,10R*)-[5-Cyano-8-fluoro-1-(1-methylpropyl)-1,3,4,9-tetrahydropyrano[3,4-b]indol-1-yl]acetic acid;
(1R*,10S*)-[5-Cyano-8-fluoro-1-(1-methylpropyl)-1,3,4,9-tetrahydropyrano[3,4-b]indol-1-yl]acetic acid;
(1R*,10S)-[5-Cyano-8-fluoro-1-(1-methylpropyl)-1,3,4,9-tetrahydropyrano[3,4-b]indol-1-yl]acetic acid;
(1R,10S)-[5-Cyano-8-fluoro-1-(1-methylpropyl)-1,3,4,9-tetrahydropyrano[3,4-b]indol-1-yl]acetic acid;
(1S,10S)-[5-Cyano-8-fluoro-1-(1-methylpropyl)-1,3,4,9-tetrahydropyrano[3,4-b]indol-1-yl]acetic acid;
(5-Cyano-1-cyclobutyl-6-fluoro-8-methyl-1,3,4,9-tetrahydropyrano[3,4-b]indol-1-yl)acetic acid;
(1R*,10S)-[5-Cyano-6-fluoro-8-methyl-1-(1-methylpropyl)-1,3,4,9-tetrahydropyrano[3,4-b]indol-1-yl]acetic acid;
(1R,10S)-[5-Cyano-6-fluoro-8-methyl-1-(1-methylpropyl)-1,3,4,9-tetrahydropyrano[3,4-b]indol-1-yl]acetic acid;
(1S,10S)-[5-Cyano-6-fluoro-8-methyl-1-(1-methylpropyl)-1,3,4,9-tetrahydropyrano[3,4-b]indol-1-yl]acetic acid;
(8-Chloro-5-cyano-1-propyl-1,3,4,9-tetrahydropyrano[3,4-b]indol-1-yl)acetic acid;
(1R)-(8-Chloro-5-cyano-1-propyl-1,3,4,9-tetrahydropyrano[3,4-b]indol-1-yl)acetic acid;
(1S)-(8-Chloro-5-cyano-1-propyl-1,3,4,9-tetrahydropyrano[3,4-b]indol-1-yl)acetic acid;
(1R*,10S)-[8-Chloro-5-cyano-1-(1-methylethyl)-1,3,4,9-tetrahydropyrano[3,4-b]indol-1-yl]acetic acid;
(1R,10S)-[8-Chloro-5-cyano-1-(1-methylethyl)-1,3,4,9-tetrahydropyrano[3,4-b]indol-1-yl]acetic acid;
(1S,10S)-[8-Chloro-5-cyano-1-(1-methylethyl)-1,3,4,9-tetrahydropyrano[3,4-b]indol-1-yl]acetic acid;
(8-Chloro-5-cyano-1-cyclobutyl-1,3,4,9-tetrahydropyrano[3,4-b]indol-1-yl)acetic acid;
(5,6-Dichloro-1-propyl-1,3,4,9-tetrahydropyrano[3,4-b]indol-1-yl)carboxylic acid; and
(5,8-Dichloro-1-propyl-1,3,4,9-tetrahydropyrano[3,4-b]indol-1-yl)carboxylic acid.

8. The method of claim 1 wherein the compound is selected from:
(5,6-Dichloro-1-propyl-1,3,4,9-tetrahydropyrano[3,4-b]indol-1-yl)carboxylic acid;
(5,8-Dichloro-1-propyl-1,3,4,9-tetrahydropyrano[3,4-b]indol-1-yl)carboxylic acid;
(5-Chloro-8-methyl-1-propyl-1,3,4,9-tetrahydropyrano[3,4-b]indol-1-yl)carboxylic acid;
8-Chloro-5-trifluoromethyl-1-propyl-1,3,4,9-tetrahydropyrano[3,4-b]indol-1-yl)carboxylic acid;
(8-Fluoro-5-trifluoromethyl-1-propyl-1,3,4,9-tetrahydropyrano[3,4-b]indol-1-yl)carboxylic acid;
(5-Trifluoromethyl-8-methyl-1-propyl-1,3,4,9-tetrahydropyrano[3,4-b]indol-1-yl)carboxylic acid;
(5-Cyano-8-methyl-1-propyl-1,3,4,9-tetrahydropyrano[3,4-b]indol-1-yl)carboxylic acid;
(1R*,10S*)-[5-Cyano-8-methyl-1-(1-methylpropyl)-1,3,4,9-tetrahydropyrano[3,4-b]indol-1-yl]carboxylic acid;
(1R*,10S*)-[5-Cyano-8-methyl-1-(1-methylpropyl)-1,3,4,9-tetrahydropyrano[3,4-b]indol-1-yl]carboxylic acid;
[5-Cyano-8-methyl-1-(3-methylpropyl)-1,3,4,9-tetrahydropyrano[3,4-b]indol-1-yl]carboxylic acid;

(5-Cyano-1-cyclobutyl-8-methyl-1,3,4,9-tetrahydropyrano[3,4-b]indol-1-yl)carboxylic acid;
(5-Cyano-6-fluoro-8-methyl-1-propyl-1,3,4,9-tetrahydropyrano[3,4-b]indol-1-yl)carboxylic acid;
(5-Cyano-8-ethyl-1-propyl-1,3,4,9-tetrahydropyrano[3,4-b]indol-1-yl)carboxylic acid;
(8-Chloro-5-cyano-1-propyl-1,3,4,9-tetrahydropyrano[3,4-b]indol-1-yl)carboxylic acid;
(5-Cyano-8-fluoro-1-propyl-1,3,4,9-tetrahydropyrano[3,4-b]indol-1-yl)carboxylic acid;
(1R)-(5-Cyano-8-fluoro-1-propyl-1,3,4,9-tetrahydropyrano[3,4-b]indol-1-yl)carboxylic acid;
(1S)-(5-Cyano-8-fluoro-1-propyl-1,3,4,9-tetrahydropyrano[3,4-b]indol-1-yl)carboxylic acid;
(1-Butyl-5-cyano-8-fluoro-1,3,4,9-tetrahydropyrano[3,4-b]indol-1-yl)carboxylic acid;
[1-(3-Butenyl)-5-cyano-8-fluoro-1,3,4,9-tetrahydropyrano[3,4-b]indol-1-yl]carboxylic acid;
[5-Cyano-8-fluoro-1-(3-methylpropyl)-1,3,4,9-tetrahydropyrano[3,4-b]indol-1-yl]carboxylic acid;
(1R*,10S*)-[5-Cyano-8-methyl-1-(1-methylpropyl)-1,3,4,9-tetrahydropyrano[3,4-b]indol-1-yl]carboxylic acid;
(1R*,10S*)-[5-Cyano-8-methyl-1-(1-methylpropyl)-1,3,4,9-tetrahydropyrano[3,4-b]indol-1-yl]carboxylic acid;
(5-Cyano-1-cyclopentyl-8-fluoro-1,3,4,9-tetrahydropyrano[3,4-b]indol-1-yl)carboxylic acid;
(5-Cyano-1-cyclohexyl-8-fluoro-1,3,4,9-tetrahydropyrano[3,4-b]indol-1-yl)carboxylic acid;
(8-Fluoro-5-nitro-1-propyl-1,3,4,9-tetrahydropyrano[3,4-b]indol-1-yl)carboxylic acid;
1-carboxymethyl-5-cyano-8-methyl-1-propyl-1,3,4,9 tetrahydro-pyrano[3,4-b]indole-7-carboxylic acid;
(5-cyano-8-methyl-1-propyl-7-propylcarbamoyl-1,3,4,9-tetrahydro-pyrano[3,4-b]indol-1-yl)-acetic acid;
(5-cyano-7-isopropylcarbamoyl-8-methyl-1-propyl-1,3,4,9-tetrahydro-pyrano[3,4-b]indol-1-yl)-acetic acid;
[5-cyano-7-(4,4-dimethyl-butylcarbamoyl)-8-methyl-1-propyl-1,3,4,9-tetrahydro-pyrano[3,4-b]indol-1-yl]-acetic acid;
(5-cyano-8-methyl-7-methylcarbamoyl-1-propyl-1,3,4,9-tetrahydro-pyrano[3,4-b]indol-1-yl)-acetic acid;
(5-cyano-8-methyl-7-dimethylcarbamoyl-1-propyl-1,3,4,9-tetrahydro-pyrano[3,4-b]indol-1-yl)-acetic acid;
(5-cyano-8-methyl-7-propoxy-1-propyl-1,3,4,9-tetrahydro-pyrano[3,4-b]indol-1-yl)-acetic acid;
(1R)-(5-cyano-8-methyl-7-propoxy-1-propyl-1,3,4,9-tetrahydro-pyrano[3,4-b]indol-1-yl)-acetic acid;
(1S)-(5-cyano-8-methyl-7-propoxy-1-propyl-1,3,4,9-tetrahydro-pyrano[3,4-b]indol-1-yl)-acetic acid;
(5-cyano-7-ethoxy-8-methyl-1-propyl-1,3,4,9-tetrahydro-pyrano[3,4-b]indol-1-yl)-acetic acid;
(5-cyano-7-methoxy-8-methyl-1-propyl-1,3,4,9-tetrahydro-pyrano[3,4-b]indol-1-yl)-acetic acid;
(5-cyano-7-isopropoxy-8-methyl-1-propyl-1,3,4,9-tetrahydro-pyrano[3,4-b]indol-1-yl)-acetic acid;
(7-butoxy-5-cyano-8-methyl-1-propyl-1,3,4,9-tetrahydro-pyrano[3,4-b]indol-1-yl)-acetic acid;
[5-cyano-7-(3,3-dimethyl-butoxy)-8-methyl-1-propyl-1,3,4,9-tetrahydro-pyrano[3,4-b)indol-1-yl]-acetic acid;
[5-cyano-7-(3-fluoro-benzyloxy)-8-methyl-1-propyl-1,3,4,9-tetrahydro-pyrano[3,4-b]indol-1-yl]-acetic acid;
(7-benzyloxy-5-cyano-8-methyl-1-propyl-1,3,4,9-tetrahydro-pyrano[3,4-b]indol-1-yl)-acetic acid;
[5-cyano-7-(2-fluoro-ethoxy)-8-methyl-1-propyl-1,3,4,9-tetrahydro-pyrano[3,4-b]indol-1-yl]-acetic acid; and
[5-cyano-7-(3-fluoro-propoxy)-8-methyl-1-propyl-1,3,4,9-tetrahydro-pyrano[3,4-b]indol-1-yl]-acetic acid.

9. The method of claim 1 wherein $R_2^1$ is n-propyl, (S)-sec-butyl, or cyclobutyl.

10. The method of claim 1 wherein the compound of the formula has a ratio of Isomer A to Isomer B of greater than 1:1.

11. The method of claim 1 wherein the compound of the formula is 100% Isomer A.

12. The method of claim 1 wherein the compound of the formula has a ratio of Isomer A to Isomer B of at least 9:1.

13. The method of claim 1 wherein the compound of the formula has a ratio of Isomer A to Isomer B of at least 8:1.

14. The method of claim 1 wherein the compound of the formula has a ratio of Isomer A to Isomer B of at least 7:1.

15. The method of claim 1 comprising a compound of a formula:

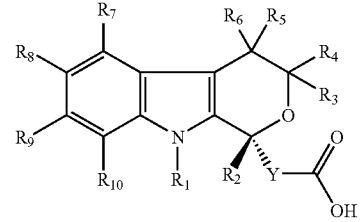

wherein:
$R_1$ is H;
$R^2$ is H, or a straight chain alkyl of 1 to 4 carbon atoms;
$R_3$—$R_6$ are H;
$R_7$—$R_{10}$ are independently H, a straight chain alkyl of 1 to 3 carbon, F, Cl, or CN;
Y is $CH_2$; or
a crystalline form or a pharmaceutically acceptable salt thereof.

16. The method of claim 15 wherein the compound is selected from:
[(R)-5-cyano-8-methyl-1-propyl-1,3,4,9-tetrahydropyrano[3,4-b]indol-1-yl]acetic acid;
[(R)-5-cyano-8-fluoro-1-propyl-1,3,4,9-tetrahydropyrano[3,4-b]indol-1-yl]acetic acid;
[(R)-5,8-dichloro-1-propyl-1,3,4,9-tetrahydropyrano[3,4-b]indol-1-yl]acetic acid; and
[(R)-5-cyano-6-fluoro-8-methyl-1-propyl-1,3,4,9-tetrahydropyrano[3,4-b]indol-1-yl]acetic acid.

17. A method of inhibiting replication of a Hepatitis C virus comprising contacting the Hepatitis C virus with a compound of a formula:

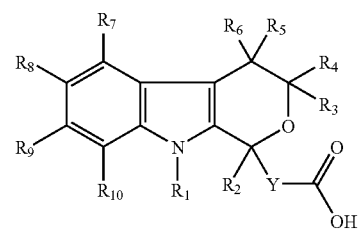

wherein:
$R_1$ is H, a straight chain alkyl of 1 to 8 carbon atoms, a branched alkyl of 3 to 12 carbon atoms, a cycloalkyl of 3 to 12 carbon atoms, an alkenyl of 2 to 7 carbon atoms, an alkynyl of 2 to 7 carbon atoms, or an arylalkyl or an alkylaryl of 7 to 12 carbon atoms;

R₂ is H, a straight chain alkyl of 1 to 12 carbon atoms, a branched alkyl of 3 to 12 carbon atoms, a cycloalkyl of 3 to 12 carbon atoms, an alkenyl of 2 to 7 carbon atoms, an alkynyl of 2 to 7 carbon atoms, an alkoxyalkyl of 2 to 12 carbon atoms, an arylalkyl or alkylaryl of 7 to 12 carbon atoms, a cyanoalkyl of 1 to 8 carbon atoms, an alkylthioalkyl of 2 to 16 carbon atoms, a cycloalkylalkyl of 4 to 24 carbon atoms, a substituted or unsubstituted aryl, or a heteroaryl, or with the proviso that when Y is CH₂ or CH₂CH₂, R² and Y together form a cycloalkyl of 3 to 8 carbon atoms;

R₃—R₆ are independently H, a straight chain alkyl of 1 to 8 carbon atoms, a branched alkyl of 3 to 12 carbon atoms, a cycloalkyl of 3 to 12 carbon atoms, an alkenyl of 2 to 7 carbon atoms, a substituted or unsubstituted aryl, furanylmethyl, arylalkyl or alkylaryl of 7 to 12 carbon atoms, alkynyl of 2 to 7 carbon atoms, or R₅ and R₆ together with the ring carbon atom to which they are attached form a carbonyl group;

R₇—R₁₀ are independently H, a straight chain alkyl of 1 to 8 carbon atoms, a branched alkyl of 3 to 12 carbons atoms, a cycloalkyl of 3 to 12 carbon atoms, an alkenyl of 2 to 7 carbon atoms, a substituted or unsubstituted aryl, a substituted or unsubstituted heteroaryl, furanylmethyl, arylalkyl or alkylaryl of 7 to 12 carbon atoms, alkynyl of 2 to 7 carbon atoms, phenylalkynyl, alkoxy of 1 to 8 carbon atoms, arylalkoxy of 7 to 12 carbon atoms, fluoroalkoxy of 1 to 12 carbon atoms, alkylthio of 1 to 8 carbon atoms, trifluoromethoxy, trifluoroethoxy, trifluoromethylthio, trifluoroethylthio, acyl of 1 to 7 carbon atoms, COOH, COO-alkyl, CONR₁₁R₁₂, F, Cl, Br, I, CN, CF₃, NO₂, alkylsulfinyl of 1 to 8 carbon atoms, alkylsulfonyl of 1 to 6 carbon atoms, pyrrolidinyl, or thiazolidinyl;

R₁₁—R₁₂ are independently H, straight chain alkyl of 1 to 8 carbon atoms, branched alkyl of 3 to 12 carbon atoms, cycloalkyl of 3 to 12 carbon atoms, a substituted or unsubstituted aryl or heteroaryl;

Y is a bond, CH₂, or CH₂CH₂; or a crystalline form or a pharmaceutically acceptable salt thereof.

18. A method of inhibiting replication of a Hepatitis C virus comprising contacting the Hepatitis C virus with a compound of a formula:

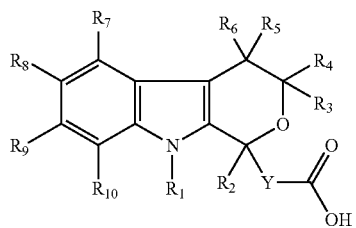

wherein:

R₁ is H, a straight chain alkyl of 1 to 6 carbon atoms, a branched alkyl of 3 to 10 carbon atoms, a cycloalkyl of 3 to 10 carbon atoms, an alkenyl of 2 to 7 carbon atoms, an alkynyl of 2 to 7 carbon atoms, or an arylalkyl of 7 to 12 carbon atoms;

R₂ is H, a straight chain alkyl of 1 to 12 carbon atoms, a branched alkyl of 3 to 10 carbon atoms, a cycloalkyl of 3 to 10 carbon atoms, an alkenyl of 2 to 7 carbon atoms, an alkynyl of 2 to 7 carbon atoms, an alkoxyalkyl of 2 to 12 carbon atoms, an arylalkyl of 7 to 12 carbon atoms, an unsubstituted aryl or an aryl substituted with one to four groups, or heteroaryl;

R₃—R₆ are independently H, a straight chain alkyl of 1 to 6 carbon atoms, a branched alkyl of 3 to 10 carbons atoms, a cycloalkyl of 3 to 10 carbon atoms, an alkenyl of 2 to 7 carbon atoms, an unsubstituted aryl or an aryl substituted with one to four groups, furanylmethyl, an arylalkyl of 7 to 12 carbon atoms, an alkynyl of 2 to 7 carbon atoms, or R₅ and R₆ together with the ring carbon atom to which they are attached form a carbonyl group;

R₇—R₁₀ are independently H, a straight chain alkyl of 1 to 6 carbon atoms, a branched alkyl of 3 to 10 carbons atoms, a cycloalkyl of 3 to 10 carbon atoms, an alkenyl of 2 to 7 carbon atoms, an unsubstituted aryl or an aryl substituted with one to four groups, an unsubstituted heteroaryl or a heteroaryl substituted with one to three groups, furanylmethyl, an arylalkyl of 7 to 12 carbon atoms, an alkynyl of 2 to 7 carbon atoms, phenylalkynyl, an alkoxy of 1 to 6 carbon atoms, an arylalkoxy of 7 to 12 carbon atoms, a fluoroalkoxy of 1 to 12 carbon atoms, an alkylthio of 1 to 6 carbon atoms, trifluoromethoxy, trifluoroethoxy, trifluoromethylthio, trifluoroethylthio, an acyl of 1 to 6 carbon atoms, a carboxy group, CONR₁₁R₁₂, F, Cl, Br, I, CN, CF₃, NO₂, an alkylsulfinyl of 1 to 6 carbon atoms, an alkylsulfonyl of 1 to 6 carbon atoms;

R₁₁—R₁₂ are independently H, a straight chain alkyl of 1 to 6 carbon atoms, a branched alkyl of 3 to 10 carbon atoms, a cycloalkyl of 3 to 10 carbon atoms, an aryl substituted with one to four groups, an unsubstituted heteroaryl or a heteroaryl substituted with one to three groups;

Y is CH₂, or CH₂CH₂; or a crystalline form or a pharmaceutically acceptable salt thereof.

19. The method of claim 17 wherein the compound is selected from:
(5-cyano-6-fluoro-8-methyl-1-propyl-1,3,4,9-tetrahydropyrano[3,4-b]indol-1-yl)acetic acid;
[(R)-5-cyano-6-fluoro-8-methyl-1-propyl-1,3,4,9-tetrahydropyrano[3,4-b]indol-1-yl]acetic acid; and
[(S)-5-cyano-6-fluoro-8-methyl-1-propyl-1,3,4,9-tetrahydropyrano[3,4-b]indol-1-yl]acetic acid.

20. The method of claim 17 wherein R₁ is n-propyl, (S)-sec-butyl, or cyclobutyl.

21. The method of claim 17 wherein the compound of the formula has a ratio of R-enantiomer to S-enantiomer of greater than 1:1.

22. The method of claim 17 wherein the compound of the formula is 100% R-enantiomer.

23. The method of claim 17 wherein the compound of the formula has a ratio of R-enantiomer to S-enantiomer of at least 9:1.

24. The method of claim 17 wherein the compound of the formula has a ratio of R-enantiomer to S-enantiomer of at least 8:1.

25. The method of claim 17 wherein the compound of the formula has a ratio of R-enantiomer to S-enantiomer of at least 7:1.

26. The method of claim 17 comprising a compound of the formula:

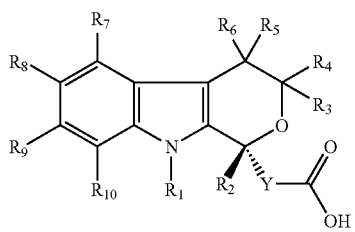

wherein
R₁ is H;
R₂ is H, a straight chain alkyl of 1 to 4 carbon atoms, or a sec-butyl;
R₃—R₆ are H;
R₇—R₁₀ are independently H, a straight chain alkyl of 1 to 3 carbon, F, Cl, or CN;
Y is CH₂; or
a crystalline form or a pharmaceutically acceptable salt thereof.

27. The method of claim 26 wherein the compound is selected from:
[(R)-5-cyano-8-methyl-1-propyl-1,3,4,9-tetrahydropyrano[3,4-b]indol-1-yl]acetic acid;
[(R)-5-cyano-8-fluoro-1-propyl-1,3,4,9-tetrahydropyrano[3,4-b]indol-1-yl]acetic acid;
[(R)-5,8-dichloro-1-propyl-1,3,4,9-tetrahydropyrano[3,4-b]indol-1-yl]acetic acid; and
[(R)-5-cyano-6-fluoro-8-methyl-1-propyl-1,3,4,9-tetrahydropyrano[3,4-b]indol-1-yl]acetic acid.

28. A method of treating a Hepatitis C viral infection in a mammal comprising providing the mammal with an effective amount of at least one pharmaceutical composition, wherein the at least one pharmaceutical composition includes a compound of a formula:

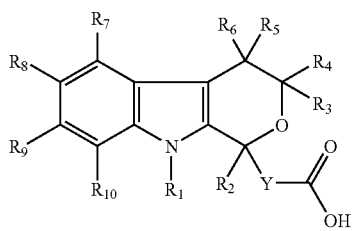

wherein:
R₁ is H, a straight chain alkyl of 1 to 8 carbon atoms, a branched alkyl of 3 to 12 carbon atoms, a cycloalkyl of 3 to 12 carbon atoms, an alkenyl of 2 to 7 carbon atoms, an alkynyl of 2 to 7 carbon atoms, or an arylalkyl or an alkylaryl of 7 to 12 carbon atoms;
R₂ is H, a straight chain alkyl of 1 to 12 carbon atoms, a branched alkyl of 3 to 12 carbon atoms, a cycloalkyl of 3 to 12 carbon atoms, an alkenyl of 2 to 7 carbon atoms, an alkynyl of 2 to 7 carbon atoms, an alkoxyalkyl of 2 to 12 carbon atoms, an arylalkyl or alkylaryl of 7 to 12 carbon atoms, a cyanoalkyl of 1 to 8 carbon atoms, an alkylthioalkyl of 2 to 16 carbon atoms, a cycloalkylalkyl of 4 to 24 carbon atoms, a substituted or unsubstituted aryl, or a heteroaryl;
R₃—R₆ are independently H, a straight chain alkyl of 1 to 8 carbon atoms, a branched alkyl of 3 to 12 carbon atoms, a cycloalkyl of 3 to 12 carbon atoms, an alkenyl of 2 to 7 carbon atoms, a substituted or unsubstituted aryl, furanylmethyl, arylalkyl or alkylaryl of 7 to 12 carbon atoms, alkynyl of 2 to 7 carbon atoms, or R₅ and R₆ together with the ring carbon atom to which they are attached form a carbonyl group;
R₇—R₁₀ are independently H, a straight chain alkyl of 1 to 8 carbon atoms, a branched alkyl of 3 to 12 carbons atoms, a cycloalkyl of 3 to 12 carbon atoms, an alkenyl of 2 to 7 carbon atoms, a substituted or unsubstituted aryl, a substituted or unsubstituted heteroaryl, furanylmethyl, arylalkyl or alkylaryl of 7 to 12 carbon atoms, alkynyl of 2 to 7 carbon atoms, phenylalkynyl, alkoxy of 1 to 8 carbon atoms, arylalkoxy of 7 to 12 carbon atoms, fluoroalkoxy of 1 to 12 carbon atoms, alkylthio of 1 to 8 carbon atoms, trifluoromethoxy, trifluoroethoxy, trifluoromethylthio, trifluoroethylthio, acyl of 1 to 7 carbon atoms, COOH, COO-alkyl, CONR₁₁R₁₂, F, Cl, Br, I, CN, CF₃, NO₂, alkylsulfinyl of 1 to 8 carbon atoms, alkylsulfonyl of 1 to 6 carbon atoms, pyrrolidinyl, or thiazolidinyl;
R₁₁—R₁₂ are independently H, straight chain alkyl of 1 to 8 carbon atoms, branched alkyl of 3 to 12 carbon atoms, cycloalkyl of 3 to 12 carbon atoms, a substituted or unsubstituted aryl or heteroaryl;
Y is a bond, CH₂, or CH₂CH₂; and
a pharmaceutically acceptable carrier.

29. The method of claim 28, further comprising providing the mammal with an effective amount of at least one biologically active agent.

30. The method of claim 29, wherein the at least one biologically active agent is provided prior to the at least one pharmaceutical composition, concurrently with the at least one pharmaceutical composition or after the at least one pharmaceutical composition.

31. The method of claim 28, 29 or 30, wherein the compound is a crystalline form or a pharmaceutically acceptable salt thereof.

32. The method of claim 29, wherein the at least one biologically active agent is selected from the group consisting of interferon, a pegylated interferon, ribavirin, protease inhibitors, polymerase inhibitors, small interfering RNA compounds, anti-sense compounds, nucleotide analogs, nucleoside analogs, immunoglobulins, immunomodulators, hepatoprotectants, anti-inflammatory agents, antibiotics, antivirals, and anti-infective compounds.

33. The method of claim 32, wherein the at least one biologically active agent is a pegylated interferon.

34. The method of claim 33, wherein the pegylated interferon is a pegylated interferon-alpha and the compound is [(R)-5-cyano-6-fluoro-8-methyl-1-propyl-1,3,4,9-tetrahydropyrano[3,4-b]indol-1-yl]acetic acid.

35. A method of treating a Hepatitis C viral infection in a mammal comprising providing the mammal with an effective amount of at least one pharmaceutical composition, wherein the at least one pharmaceutical composition includes a compound of a formula:

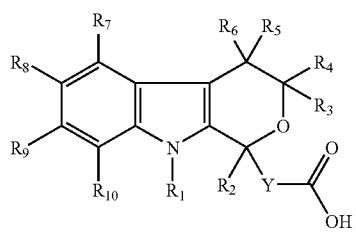

wherein:
R₁ is H, a straight chain alkyl of 1 to 6 carbon atoms, a branched alkyl of 3 to 10 carbon atoms, a cycloalkyl of 3 to 10 carbon atoms, an alkenyl of 2 to 7 carbon atoms, an alkynyl of 2 to 7 carbon atoms, or an arylalkyl of 7 to 12 carbon atoms;

R₂ is H, a straight chain alkyl of 1 to 12 carbon atoms, a branched alkyl of 3 to 10 carbon atoms, a cycloalkyl of 3 to 10 carbon atoms, an alkenyl of 2 to 7 carbon atoms, an alkynyl of 2 to 7 carbon atoms, an alkoxyalkyl of 2 to 12 carbon atoms, an arylalkyl of 7 to 12 carbon atoms, an unsubstituted aryl or an aryl substituted with one to four groups, or heteroaryl;

R₃—R₆ are independently H, a straight chain alkyl of 1 to 6 carbon atoms, a branched alkyl of 3 to 10 carbons atoms, a cycloalkyl of 3 to 10 carbon atoms, an alkenyl of 2 to 7 carbon atoms, an unsubstituted aryl or an aryl substituted with one to four groups, furanylmethyl, an arylalkyl of 7 to 12 carbon atoms, an alkynyl of 2 to 7 carbon atoms, or R₅ and R₆ together with the ring carbon atom to which they are attached form a carbonyl group;

R₇—R₁₀ are independently H, a straight chain alkyl of 1 to 6 carbon atoms, a branched alkyl of 3 to 10 carbons atoms, a cycloalkyl of 3 to 10 carbon atoms, an alkenyl of 2 to 7 carbon atoms, an unsubstituted aryl or an aryl substituted with one to four groups, an unsubstituted heteroaryl or a heteroaryl substituted with one to three groups, furanylmethyl, an arylalkyl of 7 to 12 carbon atoms, an alkenyl of 2 to 7 carbon atoms, phenylalkynyl, an alkoxy of 1 to 6 carbon atoms, an arylalkoxy of 7 to 12 carbon atoms, a fluoroalkoxy of 1 to 12 carbon atoms, an alkylthio of 1 to 6 carbon atoms, trifluoromethoxy, trifluoroethoxy, trifluoromethylthio, trifluoroethylthio, an acyl of 1 to 7 carbon atoms, a carboxy group, CONR₁₁R₁₂, F, Cl, Br, I, CN, CF₃, NO₂, an alkylsulfinyl of 1 to 6 carbon atoms, an alkylsulfonyl of 1 to 6 carbon atoms;

R₁₁—R₁₂ are independently H, a straight chain alkyl of 1 to 6 carbon atoms, a branched alkyl of 3 to 10 carbon atoms, a cycloalkyl of 3 to 10 carbon atoms, an aryl substituted with one to four groups, an unsubstituted heteroaryl or a heteroaryl substituted with one to three groups;

Y is CH₂, or CH₂CH₂; and a pharmaceutically acceptable carrier.

36. The method of claim 35, further comprising providing the mammal with an effective amount of at least one biologically active agent.

37. The method of claim 36, wherein the at least one biologically active agent is provided prior to the at least one pharmaceutical composition, concurrently with the at least one pharmaceutical composition or after the at least one pharmaceutical composition.

38. The method of claim 35, 36 or 37, wherein the compound is a crystalline form or a pharmaceutically acceptable salt thereof.

39. The method of claim 36, wherein the at least one biologically active agent is selected from the group consisting of interferon, a pegylated interferon, ribavirin, protease inhibitors, polymerase inhibitors, small interfering RNA compounds, anti-sense compounds, nucleotide analogs, nucleoside analogs, immunoglobulins, immunomodulators, hepatoprotectants, anti-inflammatory agents, antibiotics, antivirals, and anti-infective compounds.

40. The method of claim 39, wherein the at least one biologically active agent is a pegylated interferon.

41. The method of claim 40, wherein the pegylated interferon is a pegylated interferon-alpha and the compound is

[(R)-5-cyano-6-fluoro-8-methyl-1-propyl-1,3,4,9-tetrahydropyrano[3,4-b]indol-1-yl]acetic acid.

42. A method of treating a Hepatitis C viral infection in a mammal comprising providing the mammal with an effective amount of at least one pharmaceutical composition, wherein the at least one pharmaceutical composition includes a compound of a formula

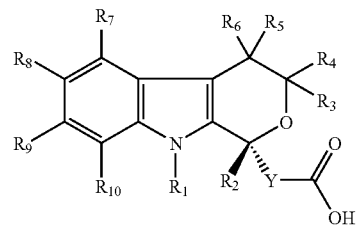

wherein:
R₁ is H;
R₂ is H, or a straight chain alkyl of 1 to 4 carbon atoms;
R₃—R₆ are H;
R₇—R₁₀ are independently H, a straight chain alkyl of 1 to 3 carbon, F, Cl, or CN;
Y is CH₂; and
a pharmaceutically acceptable carrier.

43. The method of claim 42, further comprising providing the mammal with an affective amount of at least one biologically active agent.

44. The method of claim 43, wherein the at least one biologically active agent is provided prior to the at least one pharmaceutical composition, concurrently with the at least one pharmaceutical composition or after the at least one pharmaceutical composition.

45. The method of claims 42, 43 or 44, wherein the compound is a crystalline form or a pharmaceutically acceptable salt thereof.

46. The method of claim 43, wherein the at least one biologically active agent is selected from the group consisting of interferon, a pegylated interferon, ribavirin, protease inhibitors, polymerase inhibitors, small interfering RNA compounds, anti-sense compounds, nucleotide analogs, nucleoside analogs, immunoglobulin, immunomodulators, hepatoprotectants, anti-inflammatory agents, antibiotics, antivirals, and anti-infective compounds.

47. The method of claim 46, wherein the at least one biologically active agent is a pegylated interferon.

48. The method of claim 47, wherein the pegylated interferon is a pegylated interferon-alpha and the compound is [(R)-5-cyano-6-fluoro-8-methyl-1-propyl-1,3,4,9-tetrahydropyrano[3,4-b]indol-1-yl]acetic acid.

49. A method of inhibiting replication of a Hepatitis C virus comprising contacting the Hepatitis C virus with an effective amount of at least one pharmaceutical composition, wherein the at least one pharmaceutical composition includes a compound of a formula:

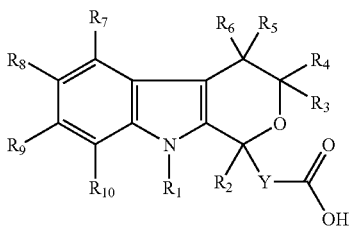

wherein:

$R_1$ is H, a straight chain alkyl of 1 to 8 carbon atoms, a branched alkyl of 3 to 12 carbon atoms, a cycloalkyl of 3 to 12 carbon atoms, an alkenyl of 2 to 7 carbon atoms, an alkynyl of 2 to 7 carbon atoms, or an arylalkyl or an alkylaryl of 7 to 12 carbon atoms;

$R_2$ is H, a straight chain alkyl of 1 to 12 carbon atoms, a branched alkyl of 3 to 12 carbon atoms, a cycloalkyl of 3 to 12 carbon atoms, an alkenyl of 2 to 7 carbon atoms, an alkynyl of 2 to 7 carbon atoms, an alkoxyalkyl of 2 to 12 carbon atoms, an arylalkyl or alkylaryl of 7 to 12 carbon atoms, a cyanoalkyl of 1 to 8 carbon atoms, an alkylthioalkyl of 2 to 16 carbon atoms, a cycloalkylalkyl of 4 to 24 carbon atoms, a substituted or unsubstituted aryl, or a heteroaryl;

$R_3$—$R_6$ are independently H, a straight chain alkyl of 1 to 8 carbon atoms, a branched alkyl of 3 to 12 carbon atoms, a cycloalkyl of 3 to 12 carbon atoms, an alkenyl of 2 to 7 carbon atoms, a substituted or unsubstituted aryl, furanylmethyl, arylalkyl or alkylaryl of 7 to 12 carbon atoms, alkynyl of 2 to 7 carbon atoms, or $R_5$ and $R_6$ together with the ring carbon atom to which they are attached form a carbonyl group;

$R_7$—$R_{10}$ are independently H, a straight chain alkyl of 1 to 8 carbon atoms, a branched alkyl of 3 to 12 carbons atoms, a cycloalkyl of 3 to 12 carbon atoms, an alkenyl of 2 to 7 carbon atoms, a substituted or unsubstituted aryl, a substituted or unsubstituted heteroaryl, furanylmethyl, arylalkyl or alkylaryl of 7 to 12 carbon atoms, alkynyl of 2 to 7 carbon atoms, phenylalkynyl, alkoxy of 1 to 8 carbon atoms, arylalkoxy of 7 to 12 carbon atoms, fluoroalkoxy of 1 to 12 carbon atoms, alkylthio of 1 to 8 carbon atoms, trifluoromethoxy, trifluoroethoxy, trifluoromethylthio, trifluoroethylthio, acyl of 1 to 7 carbon atoms, COOH, COO-alkyl, $CONR_{11}R_{12}$, F, Cl, Br, I, CN, $CF_3$, $NO_2$, alkylsulfinyl of 1 to 8 carbon atoms, alkylsulfonyl of 1 to 6 carbon atoms, pyrrolidinyl, or thiazolidinyl;

$R_{11}$—$R_{12}$ are independently H, straight chain alkyl of 1 to 8 carbon atoms, branched alkyl of 3 to 12 carbon atoms, cycloalkyl of 3 to 12 carbon atoms, a substituted or unsubstituted aryl or heteroaryl;

Y is a bond, $CH_2$, or $CH_2CH_2$; and a pharmaceutically acceptable carrier.

50. The method of claim 49, further comprising contacting the Hepatitis C virus with an affective amount of at least one biologically active agent.

51. The method of claim 50, wherein the at least one biologically active agent is provided prior to the at least one pharmaceutical composition, concurrently with the at least one pharmaceutical composition or after the at least one pharmaceutical composition.

52. The method of claims 49, 50 or 51, wherein the compound is a crystalline form or a pharmaceutically acceptable salt thereof.

53. The method of claim 50, wherein the at least one biologically active agent is selected from the group consisting of interferon, a pegylated interferon, ribavirin, protease inhibitors, polymerase inhibitors, small interfering RNA compounds, anti-sense compounds, nucleotide analogs, nucleoside analogs, immunoglobulin, immunomodulators, hepatoprotectants, anti-inflammatory agents, antibiotics, antivirals, and anti-infective compounds.

54. The method of claim 53, wherein the at least one biologically active agent is a pegylated interferon.

55. The method of claim 54, wherein the pegylated interferon is a pegylated interferon-alpha and the compound is [(R)-5-cyano-6-fluoro-8-methyl-1-propyl-1,3,4,9-tetrahydropyrano[3,4-b]indol-1-yl]acetic acid.

56. A method of inhibiting replication of a Hepatitis C virus comprising contacting the Hepatitis C virus with an effective amount of at least one pharmaceutical composition, wherein the at least one pharmaceutical composition includes a compound of a formula:

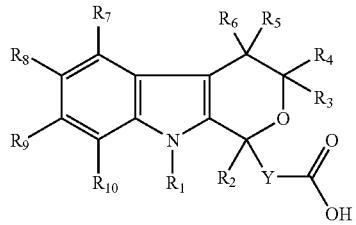

wherein:

$R_1$ is H, a straight chain alkyl of 1 to 6 carbon atoms, a branched alkyl of 3 to 10 carbon atoms, a cycloalkyl of 3 to 10 carbon atoms, an alkenyl of 2 to 7 carbon atoms, an alkynyl of 2 to 7 carbon atoms, or an arylalkyl of 7 to 12 carbon atoms;

$R_2$ is H, a straight chain alkyl of 1 to 12 carbon atoms, a branched alkyl of 3 to 10 carbon atoms, a cycloalkyl of 3 to 10 carbon atoms, an alkenyl of 2 to 7 carbon atoms, an alkynyl of 2 to 7 carbon atoms, an alkoxyalkyl of 2 to 12 carbon atoms, an arylalkyl of 7 to 12 carbon atoms, an unsubstituted aryl or an aryl substituted with one to four groups, or heteroaryl;

$R_3$—$R_6$ are independently H, a straight chain alkyl of 1 to 6 carbon atoms, a branched alkyl of 3 to 10 carbons atoms, a cycloalkyl of 3 to 10 carbon atoms, an alkenyl of 2 to 7 carbon atoms, an unsubstituted aryl or an aryl substituted with one to four groups, furanylmethyl, an arylalkyl of 7 to 12 carbon atoms, an alkynyl of 2 to 7 carbon atoms, or $R_5$ and $R_6$ together with the ring carbon atom to which they are attached form a carbonyl group;

$R_7$—$R_{10}$ are independently H, a straight chain alkyl of 1 to 6 carbon atoms, a branched alkyl of 3 to 10 carbons atoms, a cycloalkyl of 3 to 10 carbon atoms, an alkenyl of 2 to 7 carbon atoms, an unsubstituted aryl or an aryl substituted with one to four groups, an unsubstituted heteroaryl or a heteroaryl substituted with one to three groups, furanylmethyl, an arylalkyl of 7 to 12 carbon atoms, an alkynyl of 2 to 7 carbon atoms, phenylalkynyl, an alkoxy of 1 to 6 carbon atoms, an arylalkoxy of 7 to 12 carbon atoms, a fluoroalkoxy of 1 to 12 carbon atoms, an alkylthio of 1 to 6 carbon atoms, trifluoromethoxy, trifluoroethoxy, trifluoromethylthio, trifluoroethylthio, an acyl of 1 to 7 carbon atoms, a carboxy group, $CONR_{11}R_{12}$, F, Cl, Br, I, CN, $CF_3$, $NO_2$, an alkylsulfinyl of 1 to 6 carbon atoms, an alkylsulfonyl of 1 to 6 carbon atoms;

$R_{11}$—$R_{12}$ are independently H, a straight chain alkyl of 1 to 6 carbon atoms, a branched alkyl of 3 to 10 carbon atoms, a cycloalkyl of 3 to 10 carbon atoms, an aryl substituted with one to four groups, an unsubstituted heteroaryl or a heteroaryl substituted with one to three groups;

Y is $CH_2$, or $CH_2CH_2$; and a pharmaceutically acceptable carrier.

57. The method of claim 56, further comprising contacting the Hepatitis C virus with an affective amount of at least one biologically active agent.

58. The method of claim 57, wherein the at least one biologically active agent is provided prior to the at leat one pharmaceutical composition, concurrently with the at least one pharmaceutical composition or after the at least one pharmaceutical composition.

59. The method of claims 56, 57 or 58, wherein the compound is a crystalline form or a pharmaceutically acceptable salt thereof.

60. The method of claim 57, wherein the at least one biologically active agent is selected from the group consisting of interferon, a pegylated interferon, ribavirin, protease inhibitors, polymerase inhibitors, small interfering RNA compounds, anti-sense compounds, nucleotide analogs, nucleoside analogs, immunoglobulins, immunomodulators, hepatoprotectants, anti-inflammatory agents, antibiotics, antivirals, and anti-infective compounds.

61. The method of claim 60, wherein the at least one biologically active agent is a pegylated interferon.

62. The method of claim 61, wherein the pegylated interferon is a pegylated interferon-alpha and the compound is [(R)-5-cyano-6-fluoro-8-methyl-1-propyl-1,3,4,9-tetrahydropyrano[3,4-b]indol-1-yl]acetic acid.

* * * * *